United States Patent
Waters et al.

(10) Patent No.: US 12,155,103 B2
(45) Date of Patent: Nov. 26, 2024

(54) ELECTROCHEMICAL STORAGE DEVICES COMPRISING CHELATED METALS

(71) Applicant: The Regents of the University of Colorado, a body corporate, Denver, CO (US)

(72) Inventors: Scott Waters, Denver, CO (US); Michael Marshak, Denver, CO (US); Brian Hallett Robb, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 201 days.

(21) Appl. No.: 17/440,596

(22) PCT Filed: Mar. 20, 2020

(86) PCT No.: PCT/US2020/023953
§ 371 (c)(1),
(2) Date: Sep. 17, 2021

(87) PCT Pub. No.: WO2020/191330
PCT Pub. Date: Sep. 24, 2020

(65) Prior Publication Data
US 2022/0181666 A1    Jun. 9, 2022

Related U.S. Application Data

(60) Provisional application No. 62/821,227, filed on Mar. 20, 2019.

(51) Int. Cl.
*H01M 8/1016* (2016.01)
*H01M 8/18* (2006.01)

(52) U.S. Cl.
CPC ......... *H01M 8/1016* (2013.01); *H01M 8/188* (2013.01)

(58) Field of Classification Search
CPC ............................ H01M 8/1016; H01M 8/188
See application file for complete search history.

(56) References Cited

U.S. PATENT DOCUMENTS

| 4,362,791 | A | 12/1982 | Kaneko et al. | |
| 2014/0028260 | A1* | 1/2014 | Goeltz | H01M 8/08 429/500 |
| 2014/0030572 | A1* | 1/2014 | Esswein | H01M 10/4242 429/105 |
| 2014/0138576 | A1* | 5/2014 | Esswein | C07F 7/28 556/54 |
| 2016/0211539 | A1* | 7/2016 | Goeltz | H01M 8/188 |

FOREIGN PATENT DOCUMENTS

WO    WO_2015019972    *    2/2015

OTHER PUBLICATIONS

Chemist Companion, John Wiley and Sons, 1972, p. 72-79. (Year: 1972).*
Bae et. al., Electrochimica Acta 48 (2002) 279_287 (Year: 2002).*
Nakabayashi et al., Analyst, 1989, 114, 1109-11012 (Year: 1989).*
Motekaitis et al, 'The Iron(III) and Iron(II) Complexes of Nitrilotriacetic Acid', vol. 31, issue 1, 1994 (1994), p. 67-78.
Karadakov et al, 'Spectrophotometric Study of the Reaction of Titanium(IV) and Ethylenediaminetetraacetic Acid (EDTA)', Journal of Inorganic and Nuclear Chemistry, vol. 33, Aug. 1971 (Aug. 1971 ), p. 2541-2545.
Murthy et al, 'Fe(III)/Fe(II)—Ligand Systems for Use as Negative Half-Cells in Redox-Flow Cells', Journal of Power Sources, vol. 27, Aug. 1989 (Aug. 1989), p. 119-126.

* cited by examiner

*Primary Examiner* — Alexander Usyatinsky
(74) *Attorney, Agent, or Firm* — Holzer Patel Drennan

(57) ABSTRACT

Metal chelates, methods of making the metal chelate, electrolyte formulations comprising metal chelates, and electrochemical devices for energy storage using or including at least one metal chelate are disclosed. The disclosure also relates to a method to provide a metal to an electrolyte in a flow battery to plate an electrode while the electrode is in the battery.

24 Claims, 72 Drawing Sheets

ELECTROCHEMICAL STORAGE DEVICES COMPRISING CHELATED METALS

CROSS-REFERENCE TO RELATED APPLICATION

This application claims the priority and benefit of U.S. Provisional Patent Application 62/821,227, filed Mar. 20, 2019, the entirety of which is incorporated herein by reference.

TECHNICAL FIELD

This disclosure relates to methods of making the metal chelate, electrolyte formulations comprising at least one metal chelate, and electrochemical devices for energy storage using or including at least one metal chelate. The disclosure also relates to a method to provide a metal to an electrolyte in a flow battery.

BACKGROUND

Electrochemical devices such as redox flow batteries (RFB) offer compelling engineering framework for grid-scale energy storage systems by allowing the energy storage component to be in liquid form and separate from the power conversion device. By decoupling power and energy, a flow battery can provide long duration energy storage, where the marginal cost of energy storage is primarily based on the cost of the electrolyte and storage tanks. Despite these advantages, current electrolyte formulations require expensive materials such as vanadium in a vanadium redox flow battery, and thus are cost prohibitive for wide scale adoption.

Ethylene diamine tetraacetate (EDTA) has been complexed with metal ions in prior art methods. However, the metal-EDTA complexes can result in low voltage efficiency, low current efficiency, and low energy efficiency (in some embodiments around 7%).

Table 1 provides previous examples of flow battery electrolytes containing metal chelate complexes with various metals, ligands (chelates), at various pHs. Also provided in Table 1 is the solubility for a particular metal-chelate at a given pH. Notably, the highest solubility noted in Table 1 is 0.8 mol/L (M), but the pH of that material is unknown. The pH is also unknown for the second highest solubility of Table 1, of 0.5 M.

TABLE 1

| Metal | Ligand | pH (if given) | RFB Electrolyte solubility (M) | Literature (each of which is incorporated by reference in their entirety) |
|---|---|---|---|---|
| Fe | EDTA | 6 | 0.1 | Wen et al 2006 |
| Fe | EDTA | 4.5 | 0.4 | Patent WO2012117594A1 (Comparative 2, 3) |
| Fe | DTPA | 5.7 | 0.1 | Patent WO2012117594A1 (Example 14, Cathode electrolyte c) |
| Fe | (IDA)$_2$ | 5.7 | 0.1 | Patent WO2012117594A1 (Example 12, Cathode electrolyte d) |
| Ce | DTPA | 0 | 0.1 | Modiba et al 2011 |
| Ce | EDTA | 0 | 0.1 | Modiba et al 2011 |
| Mn | EDTA |  | 0.5 | Patent WO2012117594A1 (Example 1) |
| Mn | EDTA | 6.6 | 0.4 | Patent WO2012117594A1 (Example 2) |
| Mn | EDTA |  | 0.4 | Patent WO2012117594A1 (Example 3) |
| Mn | EDTA |  | 0.8 | Patent WO2012117594A1 (Example 4) |
| Mn | EDTA | 3.0 | 0.4 | Patent WO2012117594A1 (Example 5) |
| Mn | EDTA | 4.5 | 0.4 | Patent WO2012117594A1 (Example 6) |
| Mn | EDTA | 6.0 | 0.4 | Patent WO2012117594A1 (Example 7) |
| Mn | EDTA | 8.0 | 0.4 | Patent WO2012117594A1 (Example 8) |
| Mn | DTPA | 5.7 | 0.1 | Patent WO2012117594A1 (Example 13, Catholyte electrolyte d) |
| Mn | EDTA | 5.7 | 0.1 | Patent WO2012117594A1 (Example 9, Catholyte electrolyte, g) |
| Mn | EDTA | 5.7 | 0.4 | Patent WO2012117594A1 (Example 17-24, Catholyte electrolyte, g') |
| Mn | EDTA-OH | 5.7 | 0.1 | Patent WO2012117594A1 (Example 15, 16 Catholyte electrolyte, e,f) |
| Mn | EDTA-OH | 3 | 0.5 | Patent US4362791A (Example 7) |
| Cr | DTPA | 5.7 | 0.1 | Patent WO2012117594A1 (Example 20-22, Negative Electrolyte D,D',D") |
| Cr | NTA | 3-8 | N/A | Patent WO2012117594A1 |
| Cr | EDTA-OH | 5.7 | 0.1 | Patent WO2012117594A1 (Example 23, 24, Negative Elecrolyte B,B") |
| Ti | EDTA | 3 | 0.5 | Patent US4362791A (Example 2) |
| Ti | EDTA | 4 | 0.5 (or more, higher value is given) | Patent US4362791A (Example 10) |

SUMMARY

The present invention includes a flow battery comprising a metal chelate, a method of making the metal chelate, and the metal chelate. Notably, the present invention includes benefits compared to prior art.

Bae, C.; Roberts, E. P. L.; Chakrabarti, M. H.; Saleem, M. All-Chromium Redox Flow Battery for Renewable Energy Storage. Int. J. Green Energy 2011, 8 (2), 248-264 ("Bae 2011"), which is incorporated by reference in its entirety, discloses 0.2 M CrEDTA solutions utilized in an all CrEDTA RFB at pH 5.5 in 1 M sodium acetate. At low current density (30 mA cm$^{-2}$), the cell was able to achieve 99% current efficiency and 1.89 mW cm$^{-2}$ mW power output, but had poor posolyte (i.e. positive electrolyte or catholyte) kinetics leading to <5% energy efficiency. Table 2 from Bae 2011 provides the results for the charge and discharge of the undivided redox flow battery system employing 0.2 M Cr(III)-EDTA. To summarize, Table 2 of Bae 2011 states that if the constant charging current density is about 15 mA cm$^{-2}$, then the conversion of Cr(III)-EDTA to Cr(II)-EDTA is about 16.63%, the overall current efficiency is about 67.57% and the energy efficiency is about 4.23%. When the constant charging current density is about 30 mA cm$^{-2}$, then the conversion of Cr(III)-EDTA is about 47.99%, the overall current efficiency is about 99.69% and the energy efficiency is about 3.56%. Table 3 of Bae 2011 provides the average power output of a Cr(III)-EDTA undivided RFB at a discharge current density of 2.5 mA cm$^{-2}$ for different concentrations of Cr(III)-EDTA/1 M sodium acetate. When the concentration of the Cr(III)-EDTA electrolyte is 0.2 M and it is charged at 30 mA cm$^{-2}$ so that the Cr(II)-EDTA concentration is 0.095 M, this results in open circuit potential (OCP) of 2.12 V, an overall energy efficiency of 3.56%, and a power output of 1.89 mW cm$^{-2}$. When the concentration of the Cr(III)-EDTA electrolyte is 0.1 M and is charged at 30 mA cm$^{-2}$ so that the Cr(II)-EDTA concentration is 0.066 M, this results in an OCP of 2.17 V, an overall energy efficiency of 3.16%, and a power output of 1.79 mW cm$^{-2}$. When the concentration of the Cr(III)-EDTA is 0.1 M electrolyte at 15 mA cm$^{-2}$ has a concentration of 0.04 M, an OCP of 2.13 V, an overall energy efficiency of 6.94%, and a power output of 1.58 mW cm$^{-2}$. When the concentration of the Cr(III)-EDTA electrolyte is 0.2 M and charged at 15 mA cm$^{-2}$ so that the Cr(II)-EDTA concentration is 0.033 M, this results in an OCP of 2.02 V, an overall energy efficiency of 4.23%, and a power output of 0.92 mW cm$^{-2}$. The Bae 2011 CrEDTA paper uses a maximum CrEDTA concentration of 0.2 M at a pH of 5.5 in a sodium acetate buffer. The discharge current density is 2.5 mA cm$^{-2}$. The charging current densities is 15 mA cm$^{-2}$ or 30 mA cm$^{-2}$. The state of charge (SOC) reached, also known as Cr(III)-EDTA conversion, is below 48%, a maximum current efficiency of 99.69%, and a maximum energy efficiency of 6.94%. In comparison, the CrEDTA flow battery (as described in example 25) used CrEDTA at a concentration of 0.5 M. The pH of the present invention in that example is 9.0 in a sodium tetraborate buffer. A charge/discharge current of the example was 100 mA/cm$^2$. Further, the batteries of the present invention using the electrolyte of example 25 allows cycles to an SOC of 80% while exhibiting a coulombic efficiency of 99.9% and an energy efficiency of 78.3%.

WO2012117594, entitled "POWER STORAGE BATTERY," which is incorporated by reference in its entirety, describes CrEDTA paired with various positive electrolytes. The highest concentration of CrEDTA used was 0.4 M. The pH range studied were pH 3.0-8.0. Charge and discharge current densities were either 5 or 10 mA cm$^{-2}$. At a pH of 3.0, the best coulombic efficiency was 68%, voltage efficiency was 64%, overall energy efficiency was 42%, and the cell was cycled to 29% state of charge. At a pH of 5.7, the best cell performance had a coulombic efficiency of 80%, voltage efficiency of 80%, overall energy efficiency of 64%, and the cell was cycled to 75% of available capacity. At a pH of 8.0, the best cell performance had a coulombic efficiency of 70%, voltage efficiency of 68%, overall energy efficiency of 48%, and the cell was cycled to 43% of available capacity. Table 2 summarizes the results described in WO2012117594. Table 2 includes examples from WO2012117594, with varying concentrations of CrEDTA, the pH, the buffer, the current density (CD) (mA/cm$^2$), the coulombic efficiency (CE) (%), the voltage efficiency (VE) (%), the energy efficiency (EE) (%) and the available capacity used (ACU) (%).

TABLE 2

| Ex. # | CrEDTA (M) | pH Buffer | CD (mA/cm$^2$) | CE (%) | VE (%) | EE (%) | ACU (%) |
|---|---|---|---|---|---|---|---|
| 1 | 0.2 | 5.7 NaOAc | 10 | 80 | 80 | 64 | 75 |
| 2 | 0.4 | 5.7 NaOAc | 5 | 75 | 85 | 64 | 55 |
| Comp. 1 | 0.1 | 5.5 NaOAc | 5 | 50 | 60 | 30 | 10 |
| Comp. 2 | 0.4 | 5.7 NaOAc | 5 | 65 | 95 | 59 | 25 |
| Comp. 3 | 0.4 | 5.7 NaOAc | 5 | NA | NA | NA | NA |
| Comp. 4 | 0.4 | 5.7 NaOAc | 5 | NA | NA | NA | NA |
| Comp. 5 | 0.4 | 5.7 NaOAc | 5 | 55 | 70 | 39 | 15 |
| Comp. 6 | 0.4 | 5.7 NaOAc | 5 | 40 | 80 | 32 | 10 |
| Comp. 7 | 0.4 | 5.7 NaBr | 5 | 45 | 90 | 41 | 15 |
| 3 | 0.32 | 5.7 None | 10 | 68 | 72 | 49 | 59 |
| 4 | 0.24 | 5.7 None | 10 | 76 | 70 | 53 | 82 |
| 5 | 0.4 | 3.0 None | 10 | 66 | 64 | 42 | 29 |
| 6 | 0.4 | 4.5 None | 10 | 74 | 70 | 52 | 39 |
| 7 | 0.32 | 6.0 None | 10 | 74 | 74 | 55 | 60 |
| 8 | 0.32 | 8.0 None | 10 | 70 | 68 | 48 | 43 |

In comparison, the present invention allows for the cycling of CrEDTA in an RFB at concentrations of 0.5 M, at a pH of 9.0. The cell has a coulombic efficiency of 99.9%, voltage efficiency of 79.0%, overall energy efficiency of 78.3%, and the cell was cycled to 80% of the available capacity. The cell was also able to be charged and discharged at an increased current density of 100 mA/cm$^2$. Notably, the present invention provides for a higher current density, the ability to obtain a higher concentration, and the ability to utilize a larger percentage of available capacity. The efficiencies of the present invention are also better than those reported, with a specific emphasis near 100% coulombic efficiency as set forth in example 25 below. Table 3 provides a summary to allow for a comparison of WO2012117594 to example 25.

TABLE 3

| Ex. # | CrEDTA (M) | pH Buffer | CD (mA/cm$^2$) | CE (%) | VE (%) | EE (%) | ACU (%) |
|---|---|---|---|---|---|---|---|
| 25 | 0.5 | 9.0 Sodium tetraborate | 100 | 99.9 | 79.0 | 78.3 | 80 |

U.S. Pat. No. 4,362,791 entitled "Redox Battery," which is incorporated by reference in its entirety, describes a CrEDTA used as a negative electrolyte at 0.5 M at pH 3. No further information is given in regard to how the cell was run or the resultant efficiencies. The disclosure of U.S. Pat. No. 4,362,791 is different from the present invention as U.S. Pat. No. 4,362,791 recites CrEDTA at a pH of 3, compared to a pH of 9 as used in the present invention. Notably, the CD, CE, VE, EE, or ACU is not disclosed.

Modiba, P.; Matoetoe, M.; Crouch, A. M. Kinetics Study of Transition Metal Complexes (Ce-DTPA, Cr-DTPA and V-DTPA) for Redox Flow Battery Applications. *Electrochimica Acta* 2013, 94, 336-343, which is incorporated by reference in its entirety, discloses electrochemical properties of Ce, Mn, Cr, Fe, V with various ligands at 1 M $H_2SO_4$ (pH 0). The present invention can operate at a higher pH (in some embodiments a pH of about 9), for various buffer systems, which results in increased performance.

Ogino, H.; Nagata, T.; Ogino, K. Redox Potentials and Related Thermodynamic Parameters of (Diaminopolycarboxylato)Metal(III/II) Redox Couples. *Inorg. Chem.* 1989, 28 (19), 3656-3659, which is incorporated by reference in its entirety, discloses the reduction potential of various Cr, Fe, V, Ru couples with various EDTA and PDTA type ligands. Notably, none of the materials disclosed in Ogino are used in a battery setting.

Ogino, Hiroshi; Watanabe, Toshiyuki; Tanaka, Nobuyuki. Equilibrium and Kinetic Studies of the Reactions of N-Substituted Ethylenediamine-N,N',N'-Triacetatoaquachromium (III) with Acetate Ions. *Inorg. Chem.* 1975, 14 (9), 2093-2097, which is incorporated by reference in its entirety, discusses the mechanism of acetate replacing water on CrEDTA. Such a substitution is not advantageous for the present invention.

Tanaka, N.; Ito, T. The Polarographic Investigation on the Reaction between Chromium(II)-Ethylenediaminetetraacetate and Nitrate Ions. *Bull. Chem. Soc. Jpn.* 1966, 39 (5), 1043-1048, which is incorporated by reference in its entirety, discloses the reduction of nitrates by Cr(II) species, which is again disadvantageous in the final product of the invention.

Ibanez, J. G.; Choi, C.-S.; Becker, R. S. Aqueous Redox Transition Metal Complexes for Electrochemical Applications as a Function of PH. *J. Electrochem. Soc.* 1987, 134 (12), 3083-3089, which is incorporated by reference in its entirety, describes various chelated complexes including Fe-polyaminoacetate complexes and Cr(EDTA) in acidic to mildly acidic conditions. 0.15 M CrEDTA (low concentration) at a maximum pH of 5. 0.1 M Fe(II)DTPA (low concentration) is also reported to have electrochemical activity at pH 8 in ammonium fluoride. In contrast, the present invention operates in a flow battery at a higher pH of 9, in some embodiments, higher concentration (greater than 0.5M, up to about 1.3 M in some embodiments), and under different buffer conditions.

Iron-chromium (FeCr) RFBs are low cost because of the large abundance of chromite ore. Although the FeCr electrolyte cost is low, challenges associated with FeCr flow batteries include low cell voltage (1.2 V), low current densities (21.5 mA cm') due to sluggish $Cr^{3+/2+}$ redox kinetics, required operation in corrosive HCl solution for metal ion solubility, issues with membrane cross-over of metal ions, and hydrogen gas evolution. The use of metal chelates, including those employing chromium and iron, has been investigated for RFB electrolytes, enabling the manipulation of redox potential, solubility, and solution electrolyte pH. In particular, chelating chromium with the ubiquitous chelate EDTA has been shown to shift the $Cr^{3+/2+}$ reduction potential to −0.99 V vs. SHE near neutral pH and to enhance the chromium redox kinetics by more than $10^5$. A symmetric flow battery using CrEDTA for both negative and positive redox couples was reported in Bae 2011; however, the overall energy efficiency was less than 7% when the chelate was EDTA.

Since coordination of water to CrEDTA could be facilitating a catalytic pathway for water splitting, 1,3-propylenediaminetetraacetate (PDTA) was utilized as a potential chelate. PDTA complexes Cr' ions in a nearly octahedral geometry (hexadentate) and excludes water from the primary coordination sphere. The $Cr^{3+/2+}$ reduction potential of CrPDTA (−1.10 V vs. SHE) is also more negative than CrEDTA, further increasing the battery voltage when used as a negative electrolyte. The electrochemical behavior of CrPDTA as an electrolyte paired with $K_4Fe(CN)_6$, which is an inexpensive and robust positive electrolyte used in other flow battery systems, was also utilized. Similar results can be obtained by using 1,4-butylenediaminetetraacetate (BDTA) as the chelate with the metal ion.

This disclosure describes electrolyte formulations that include a class of metal chelates that address and solve many of the deficiencies in alternative systems. Unexpectedly, these electrolyte formulations provide greater solubility, redox kinetics, and stability than what has been reported previously using a metal-EDTA complex. These electrolyte formulations enable the production of highly efficient, high voltage and high-performance flow batteries.

The electrolyte described in the disclosure includes a transition metal, for example chromium, complexed with a chelating agent, for example PDTA, BDTA, diethylenetriaminepentaacetic acid (DTPA), nitrilotriacetate (NTA), N-(2-Hydroxyethyl)ethylenediaminetriacetic acid (HEDTA), or 1,2-diaminocyclohexane-N,N'-tetraacetic acid (CyDTA), that generates high-voltage aqueous flow batteries between a pH of 6-11, in some embodiments a near neutral pH. The use of this electrolyte provides greater cell potential compared to RFBs that do not include this electrolyte. An example electrolyte of the disclosure, CrPDTA electrolyte, was tested with a $Fe(CN)_6^{4-/3-}$ couple to generate a flow battery with a cell potential of 1.62 V. The iron-chromium chelate RFB was cycled at 0.1 A $cm^{-2}$ with 100% current efficiency, 80% round-trip energy efficiency, no capacity loss over 75 cycles, and a peak power density above 0.5 W $cm^{-2}$.

FIG. 1 illustrates differences in the voltage and current efficiency of a single charge-discharge cycle for flow batteries containing of a prior art electrolyte, specifically CrEDTA, compared to an electrolyte of the present invention which utilizes a metal-PDTA, specifically CrPDTA. The CrPDTA provides a higher discharge voltage and 100% current efficiency.

A second RFB was demonstrated pairing CrPDTA with the $Br_2/Br^−$ redox couple, which provided a cell potential of 2.13 V—the highest ever recorded for an all-aqueous flow battery. The CrBr battery displayed 76% round-trip energy efficiency upon cycling at 0.1 A $cm^{-2}$, as well as a peak power density of nearly 0.7 W $cm^{-2}$. These results demonstrate the ability of chelated metal complexes to enhance redox potential, solubility, stability, and electron transfer kinetics. Moreover, the complete exclusion of water coordinated directly to metal ions is a valuable approach in enabling stable high-voltage aqueous battery systems and establishes a general method for inhibiting water splitting reactions. Other advantages can be present in a RFB when both the catholyte (i.e. a cathode electrolyte) and the anolyte (i.e. an anode electrolyte) include a metal chelate, where the chelate is PDTA or BDTA.

An aspect of the disclosure relates to metal chelate. The metal chelate comprises a PDTA CyDTA, NTA, DTPA, HEDTA, EDTA or BDTA chelating material, and the metal can be chromium, manganese, titanium, vanadium, cerium, or iron. The metal of the metal chelate can affect the voltage. Advantageously, the metal coordinates with the chelating material such that it reduces (less than 5%) or eliminates water splitting reactions.

An aspect of the disclosure is a method of making the metal chelate. Advantageously, the method of the invention results in a greater than about 85% of the metal ions being complexed with the chelate, in some embodiments between about 90% and about 100%. Previous methods as described in Weyh, J. A.; Hamm, R. E. Iminodiacetato, Methyliminodiacetato, and 1,3-Propanediaminetetraacetato Complexes of Chromium(III). *Inorg. Chem.* 1968, 7 (11), 2431-2435 (incorporated by references in its entirety) for CrPDTA, and Ogino, H.; Chung, J.-J.; Tanaka, N. On the Utilization of Chromium(II) Ions for the Syntheses of Alkylenediaminetetraacetatochromate(III) Complexes. *Inorganic and Nuclear Chemistry Letters* 1971, 7 (2), 125-129 (incorporated by reference in its entirety) for CrBDTA, results in yields (i.e. the amount of complexed materials that became solids) of 60 and 85%, respectively.

An aspect of the disclosure is a flow battery comprising the metal chelate. The battery can include more than one metal chelate, wherein the metal chelate is negatively charged. The membrane of the flow battery can be a cation exchange membrane or an anion exchange membrane, or other suitable separator. The electrolyte of the flow battery can include aqueous solutions of metal chelate. The electrodes of the flow battery can be porous carbon electrodes, or a metal plated carbon electrode.

An aspect of the disclosure is directed to a method to provide a metal to an electrode in a flow battery. Advantageously, the flow battery does not need to be disassembled to coat or plate the electrode with the metal. The metal can be bismuth or lead, for example, and can be present in the electrolyte in an amount between about 0.1 mM to about 10 mM.

An aspect of comprises a flow battery, comprising an anolyte comprising a metal chelate, wherein the metal of the metal chelate is a transition metal, and wherein the chelate is selected from the group consisting of PDTA, BDTA, DTPA, NTA, CyDTA, EDTA, or HEDTA, and a catholyte comprising $Fe(CN)_6$.

Various embodiments can be combined with various aspects of the invention. The transition metal of the flow battery can be a chromium, a titanium, a manganese, a vanadium, a cerium, or an iron. A charge of the metal chelate can be negative, which can be −1, −2, or −3. The metal chelate can include at least one counter ion, which can be potassium, sodium, lithium, ammonium, tetraethylammonium, tetrabutylammonium, or other tetraalkylammonium salts. The solubility of the metal chelate with the counter ion can be between about 0.1 M and about 2.0 M. The chelate can coordinate with between about 90% and about 100% of the metal. When the chelate is NTA, two NTA molecules can be bound to a single metal. A pH of the metal chelate can be between about 6 and about 11. In some embodiments, the pH can be greater than about 8. In some embodiments, the anolyte can comprises K[Cr(PDTA)] and the catholyte comprises $K_4[Fe(CN)_6]$; the anolyte comprises Na[Cr(EDTA)] and the catholyte comprises $Na_4[Fe(CN)_6]$; or K[Cr(PDTA)] as the anolyte, and wherein the catholyte is one of a $K_2[Mn(BDTA)]$, a K[Cr(EDTA)], or a $Br_2/Br^-$. The anolyte can include a second metal, which can be bismuth, lead, bismuth chelate, lead chelate, or a combination therein.

An aspect of the invention is a method to form a metal chelate, comprising mixing a metal salt and a chelate in a solvent, where the chelate is in stoichiometric excess to the metal salt to form a mixture, and adjusting the temperature of the mixture to between about 0° C. and about 150° C. for a time between about 10 minutes and about 7 days to form the metal chelate. A yield of the metal chelate is greater than 85%.

Various embodiments can be combined with aspects of the invention. For example, the metal salt does not need to be purified prior to the mixing. The time of mixing can be about 3 days, and the temperature can be about 100° C. Greater than about 99% of a metal of the metal salt can be complexed in the metal chelate. No water molecules can be coordinating to a metal center of the metal chelate. A metal of the metal salt can be a transition metal. The chelate of the metal chelate can be selected from the group consisting of PDTA, BDTA, DTPA, NTA, CyDTA, EDTA, or HEDTA.

An electrolyte, comprising a solvent, a metal chelate, wherein the metal chelate dissolves in the solvent to form the electrolyte, wherein a metal of the metal chelate is a transition metal, and wherein the chelate of the metal chelate is PDTA, CyDTA, NTA, DTPA, HEDTA, EDTA, BDTA, and combinations thereof, and a second metal comprising at least one of bismuth, lead, bismuth chelate, lead chelate, or a combination therein.

The second metal can be soluble in the solvent. The metal chelate can be CrPDTA, CrBDTA, FePDTA, FeBDTA, V(PDTA), V(BDTA), Mn(PDTA), or Mn(BDTA). The solvent can be water. The electrolyte can be an anolyte or a catholyte.

An aspect of the invention is a flow battery, comprising an anolyte comprising a metal chelate, wherein a metal of the metal chelate is a transition metal, and wherein a chelate of the metal chelate is PDTA, CyDTA, NTA, DTPA, HEDTA, or BDTA, a catholyte, at least two electrodes, and a membrane, wherein the membrane separates the anolyte and the catholyte, wherein a state of charge of the flow batter is between about 83% and about 100%.

Various embodiments can be combined with various aspects of the invention. The metal chelate of the anolyte can include a counter ion. The catholyte can include a second metal chelate, wherein a second method of the second metal chelate is a transition metal, and wherein a chelate is selected from the group consisting of selected from the group consisting of PDTA, BDTA, DTPA, NTA, CyDTA, EDTA, or HEDTA. The metal chelate of the anolyte further comprises a counter ion, and wherein the catholyte comprises a second metal chelate, wherein a second method of the second metal chelate is a transition metal, and wherein a chelate is selected from the group consisting of selected from the group consisting of PDTA, BDTA, DTPA, NTA, CyDTA, EDTA, or HEDTA, and a second counter ion, wherein the counter ion and the second counter ion are the same. The pH of the catholyte and the pH of the anolyte are between 6 and 11. A current density of the flow battery can be between 50 $mA/cm^2$ and 200 $mA/cm^2$, between about 100 $mA/cm^2$ and about 200 $mA/cm^2$, or between about 50 $mA/cm^2$ and about 100 $mA/cm^2$. A voltage efficiency of the flow battery can be between about 75-95%. An overall efficiency can be between about 70-95%. A current efficiency can be between about 50% and about 100%. The battery capacity can be reduced by less than about 5% per week. The hydrogen evolution of the battery can be less than about 5% per day. A state-of-charge of the battery can decrease by less than 10% after one week of storage at 20° C. and atmospheric pressure. The membrane can be a cation exchange membrane, which can be a sulfonated tetrafluoroethylene based fluoropolymer-copolymer (Nafion®). The electrolytes of the flow battery can be coated with at least 0.01 μg/cm$^2$ of the second metal. The second metal is bismuth, lead, bismuth chelate, lead chelate, or a combination therein.

An aspect of the invention is a method to plate an electrode, comprising dissolving a plating material in a solution, wherein the solution is an electrolyte. The flow battery is not disassembled to plate the electrode.

An aspect of the invention is a metal chelate, comprising a metal coordinated to a chelate, wherein the metal comprises a transition metal and wherein the chelate is EDTA, wherein a concentration of the metal chelate is between 0.8 M and about 2 M at a pH between about 6 and about 11.

An aspect of the invention is a metal chelate, comprising a metal coordinated to a chelate, wherein the metal comprises a transition metal selected from the group consisting of chromium, vanadium, cerium, titanium, or combination thereof, and wherein the chelate is at least one of a PDTA, CyDTA, NTA, DTPA, HEDTA, or BDTA, wherein a concentration of the metal chelate is greater than 0.4M and less than or equal to about 2 M.

DETAILED DESCRIPTION

Figure 1:
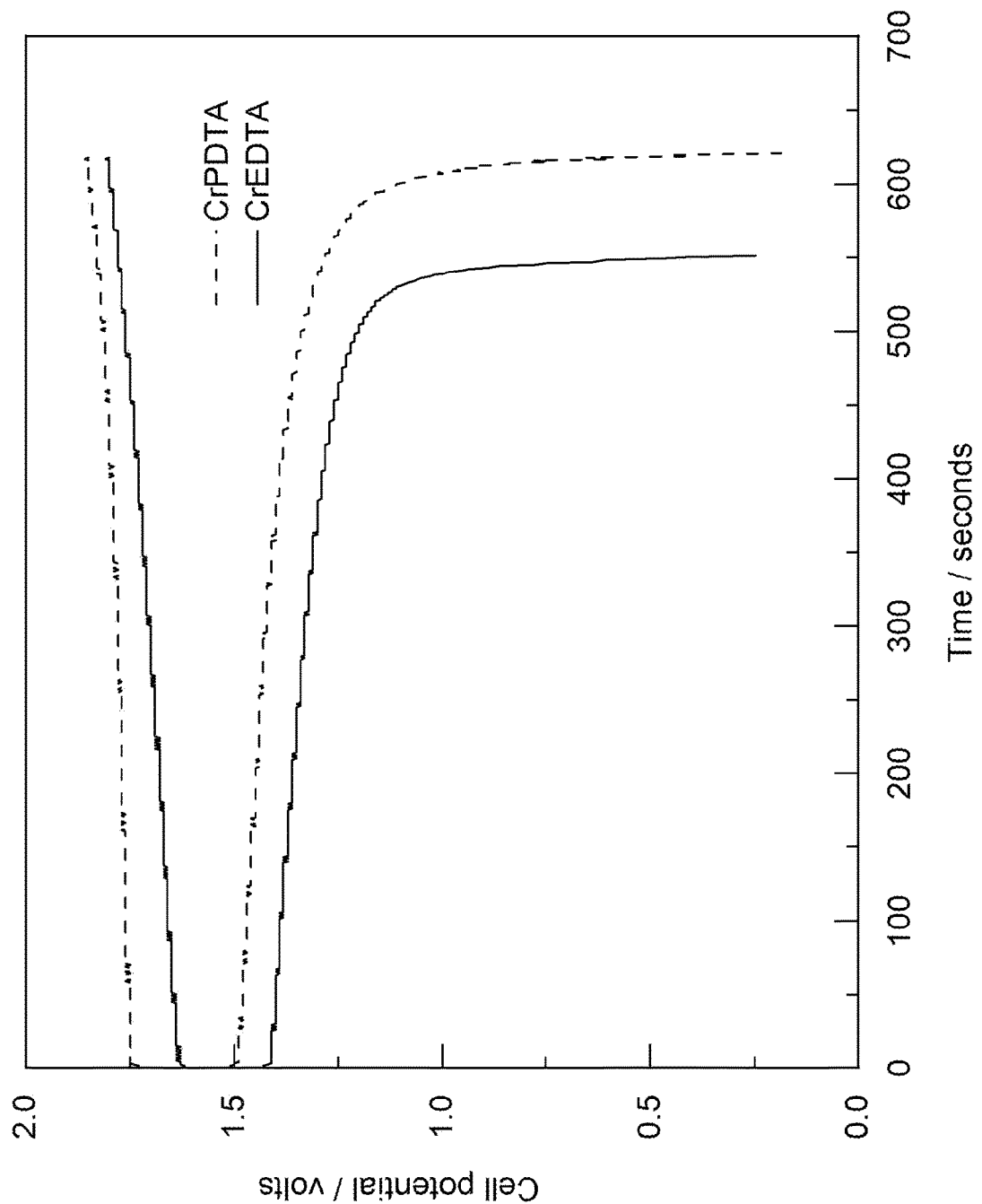
FIG. 1 illustrates a single charge-discharge cycle for a flow battery containing either CrEDTA and CrPDTA electrolyte (0.4 M) as the negative electrolyte and a mixture of 0.3 M K$_4$Fe(CN)$_6$, 0.45 M K$_3$Fe(CN)$_6$ as the positive electrolyte. The CrPDTA provides a higher discharge voltage and 100% current efficiency, while the CrEDTA provides a lower discharge voltage.

This disclosure provides electrolyte formulations for use in a flow battery that include at least one chelated metals. The chelated metals comprise a single metal, and are negatively charged. In some embodiments, a metal chelate can be in the anolyte, the catholyte, or both. The metal chelate need not be the same in the anolyte and/or the catholyte. Furthermore, because the chelating material effectively and preferably coordinates with the metal, depending on the metal being used, water cannot coordinate with the metal. Long chain aminopolycarboxylates (APC), such as 1,6-diaminohexanetetraacetate, are not preferred as they can result in more than one chromium complexing with the APC, which decreases the efficiency of the metal chelates. While in some embodiments, the chelate is not EDTA, in other embodiments, the chelate can be EDTA. Other suitable chelate materials, such as PDTA, BDTA, DTPA, CyDTA, HEDTA, or NTA, can improve the energy efficiency of the battery to between about 8 and 95%. In some embodiments, the energy efficiency can be about 8%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, or a range within two of the stated values, or any value or range within the range of 8% and 95%. Energy efficiency in this context means round-trip DC to DC energy in (in Wh) versus energy out (in Wh) of the cell, not including loses from pumping or other required power systems for operation. The current efficiency when a metal-chelate wherein the chelate is PDTA, BDTA, DTPA, HEDTA, EDTA, CyDTA, or NTA can be between about 50 and about 100%. In some embodiments, the current efficiency can be about 50%, about 60%, about 70%, about 80%, about 90%, or about 100%, or a range within two of the stated values, or any value or range within the range of 50% and 100%. Current efficiency means the number of coulombs of charge outputted by the cell divided by the number of coulombs of charge inputted to the cell, not taking into consideration system performance like AC-DC power conversion efficiency. In contrast, when EDTA coordinates to chromium, water can bind to metal ion leading to cell inefficiency. As illustrated in FIG. 1, the energy efficiency and the discharge voltage of the metal chelate of the present invention is improved compared to batteries using CrEDTA in the electrolyte.

Notably, the use of a metal chelate comprising EDTA is also an aspect of the invention. Unlike prior art methods which may use a metal chelate comprising EDTA at low concentrations and low pH, the present invention utilizes a metal chelate comprising EDTA at a concentration between about 0.4 M and about 2.0 M, and a pH between about 6 and about 11.

An aspect of the invention is a metal chelate, wherein the metal is a transition metal, and wherein the chelate is PDTA, BDTA, DTPA, CyDTA, HEDTA, EDTA, or NTA. Other suitable APC materials that result in a single metal bonded to the chelate can also be used as the chelate. While in some embodiments, the chelate cannot be EDTA, in other embodiments, the chelate can be EDTA. The transition metal can be chromium, titanium, manganese, vanadium, cerium, or iron. The metal chelate can be neutral, negatively or positively charged, which can depend on the metal ion. In some embodiments, for example when the metal is cerium, then the cerium can be used as a positive electrolyte. In some embodiments, the charge of the metal chelate can be −1, −2, or −3.

In some embodiments, the solubility of the metal chelate can be altered by the nature of the counter cation(s). Altering the solubility can improve the energy density of the battery comprising the metal chelate. Suitable counter ions can include lithium, sodium, potassium, ammonium, TEA, TBA, mixed cations, or combinations thereof. The solubility of the metal chelate with the counter ion can be between about 0.4 M and about 2.0 M, in some embodiments about 0.4 M, about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, or about 2 M, or a range between two of these values, or any value or subrange between the range of 0.4 M and 2 M. Suitable combinations of counter ions and metal chelates are discussed below in Table 4.

In some embodiments, the coordination of the metal and the chelate of the metal chelate can vary depending on chelate, metal, and metal oxidation state. In some embodiments the metal can coordinate to the chelate such that the equilibrium constant between the metal chelate complex and the free metal ion and free chelate exceeds $10^{25}$. In other words, a virtually undetectable amount of unchelated metal ions exist in solution. In some embodiments, the chelate of the metal chelate can coordinate to the metal ion in amount between about 90% and about 100%, in some embodiments about 90%, about 91%, about 92%, about 93%, about 94%, about 95%, about 96%, about 97%, about 98%, about 99%, about 100%, or a range between two of these values, or any value or subrange between the range of 90% and 100%. By coordinating preferentially with the chelate, water ligand(s) are unable or can be less able to coordinate with the metal of the metal chelate. Water coordinating with the metal in the metal chelate can reduce the efficiency of the of the resulting battery. Further, excess chromium can form a precipitate, which can also reduce the efficiency of the resulting battery. Thus, an advantage aspect of the disclosure is that the chelate of the metal chelate preferentially coordinates with the metal ion. Metal chelates of the invention include, by way of example only, CrPDTA, CrBDTA, CrDTPA, CrNTA, CrCyDTA, CrHEDTA, CrEDTA, FePDTA, FeBDTA, FeDTPA, FeNTA, FeCyDTA, FeHEDTA, FeEDTA, V(PDTA), V(BDTA), V(DTPA), V(NTA), V(CyDTA), V(HEDTA), V(EDTA), Mn(PDTA), Mn(BDTA), MnDTPA, MnNTA, MnCyDTA, MnHEDTA, MnEDTA, CePDTA, CeBDTA, CeDTPA, CeNTA, CeCyDTA, CeHEDTA, CeEDTA, TiPDTA, TiBDTA, TiDTPA, TiNTA, TiCyDTA, TiEDTA, or TiHEDTA. The concentration of the metal chelate can be between about 0.1 M and about 2 M. In some embodiments, the concentration of the metal chelate can be about 0.1 M, about 0.5 M, about 1.0 M, about 1.5 M, about 2 M, or a range between two of these values, or any value or subrange between the range of about 0.1 M and about 2 M.

An aspect of the invention is a method to form a metal chelate. The method includes mixing a metal complex and a chelate in a solvent, wherein the chelate is in stoichiometric excess to the metal complex to form a mixture. The temperature of the mixture is adjusted to between about 20° C. and about 150° C., for between about 10 minutes and about 7 days to form the metal chelate. The metal chelate has a concentration between about 0.1 M and about 2 M. The conversion rate of the metal complex and the chelate to the metal chelate is between 90% and about 100%.

In some embodiments, the metal salt precursor does not need to be purified prior to mixing the metal complex with the chelate in the solvent. Metal salts can be selected to produce a metal chelate, where the metal is a transition metal. The transition metal can be titanium, vanadium, chromium, manganese, cerium, or iron. Suitable metal salts include, but are not limited to, $KCr(SO_4)_2 \cdot 12H_2O$, $TiCl_4$, $TiOSO_4$, $V_2O_5$, $V_2(SO_4)_3$, $KV(SO_4)_2$, $FeSO_4$, $MnSO_4$, $MnCl_2$, $FeCl_3$, $Fe(NO_3)_3 \cdot 12H_2O$, $Ce_2(SO_4)_3$ and $CeCl_3$ or $CrCl_3 \cdot 6H_2O$. The solvent of the mixture can be an aqueous solution, for example water (tap, deionized, or distilled, or combinations thereof). In some embodiments, the solvent interaction with the metal chelate complex can alter the reduction potential. Suitable solvents can include acetonitrile, tetrahydrofuran, 1,2-difluorobenzene, dimethylformamide, and combinations thereof. By way of example, when the material is CrPDTA, the approximate $E_{1/2}$ [V vs Fc/Fc$^+$] is −2.3 V for acetonitrile, −2.6 V for tetrahydrofuran, and −2.3 V for 1,2-difluorobenzene.

The mixture of the metal salt and the chelate in the solvent can be purged initially, periodically (every about 5 to about 30 minutes of the mixture time) or continuously. Suitable purging gases include nitrogen, argon, helium, or combinations thereof. The temperature of the mixture is between about 0° C. and about 150° C., in some embodiments, about 100° C. As the boiling point of water is 100° C., temperatures exceeding 100° C. can be under pressure. In some embodiments about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., or any range within two of these values, or any value or subrange between the range of about 0° C. and about 150° C. In some embodiments, the total mixing time can be between about 10 minutes and about 168 hours, in some embodiments about 72 hours. In some embodiments about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 24 hours, about 36 hours, about 48 hours, about 60 hours, about 72 hours, about 84 hours, about 96 hours, about 108 hours, about 120 hours, about 132 hours, about 144 hours, about 156 hours, or about 168 hours, or any range within two of these values, or any value or subrange between the range of 10 minutes and 7 days. After between about 5 and about 120 minutes of initial heating of the mixture to the mixing temperature, a pH adjuster can be added to the mixture. The pH adjuster can be added after about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, or about 120 minutes or any range within two of these values, or any value or subrange between about 5 minutes and about 120 minutes.

During the mixing of the metal salt and the chelate, the pH of the mixture can be monitored to reduce unwanted side reactions including cross-linking or polymerization. The pH adjuster can be a solid or a liquid, or combination thereof. In some embodiments, the pH adjuster can be KOH, NaOH, $K_2CO_3$, $KHCO_3$, $Na_2CO_3$, $NaHCO_3$, $NH_4OH$, LiOH or combinations thereof. The counter ion can be provided to the chelate based on the pH adjuster. For example, if the desired counter ion of the metal chelate is potassium, then KOH, $K_2CO_3$, or $KHCO_3$, can be used as the pH adjuster. For CrPDTA, an advantage of the potassium base is that higher concentrations of the metal chelate can be obtained, where the concentration can be greater than 1.0 M. In some embodiments, the concentration can be between 0.5 M and about 1.1 M. In some embodiments, the pH can be water with a buffer. The pH adjuster can be used to adjust the pH of the mixture to a pH between about 6 and about 11. In some embodiments, the pH can be adjusted to about 6, about 7, about 8, about 9, about 10, about 11, or any range within two of these values, or any value or subrange between the range of pH 6 and pH 11.

The temperature of the mixture can be adjusted to between about 0° C. and about 50° C., in some embodiments about 25° C. In some embodiments, the mixture can be cooled to about 0° C., about 10° C., about 15° C., about 20° C., about 25° C., about 30° C., about 35° C., about 40° C., about 45° C., about 50° C., or any range within two of these values, or any value or subrange between the range of 0° C. and about 50° C. In some embodiments, the synthesis can be cooled to about room temperature (about 25° C.) before a second solvent is added. A second solvent can be added to the mixture at about an equal volume ratio of the mixture to the second solvent (about 1:0.75 to about 1:1.25, in some embodiments about 1:0.75, about 1:1, about, about 1:1.1, about 1:1.2, about 1:1.25) to precipitate a solid. In some embodiments, the second solvent can be an alcohol, for example ethanol, isopropanol, methanol, etc., or a ketone, for example acetone, ethyl acetate, methylethylketone, etc., or a combination of an alcohol and a ketone. The precipitate will depend upon the initial constituents of the mixture, which can be determined by one skilled in the art. Advantageously, the method of the invention can be used to remove sulfates from the mixture, if present. In some embodiments, the precipitate can be $K_2SO_4$. Removing the sulfates and/or acetone when present increases purity of the metal chelate. However, in some embodiments, impurities that would affect performance, such as sulfates or acetone, can be avoided by not using these materials in the synthesis of the material. Rather, other materials containing the metal of the metal chelate can be used in the synthesis. Using chromium as an example of the metal, the chromium can be provided using $CrCl_3 \cdot 6H_2O$, $Cr_2O_3$ or $Cr(OH)_3$ in the reaction. Avoiding sulfate and/or acetone in the final product increases the purity of the material with respect to the performance impacting impurities, such that the current efficiency of the resulting battery comprising the material is increased to between about 50% and about 100%. In some embodiments, while $NO_3^-$ is able to be reduced by Cr(II) chelate materials, such as CrPDTA, $Cr(NO_3)_3 \cdot 9H_2O$ should be avoided due to hard to remove $NO_3^-$ impurities.

The filtrate can be concentrated, which can remove unwanted acetone or concentrate the water-based solution, under a pressure of less than atmospheric pressure (e.g. less than 1 atm at sea level or equivalent at different altitudes as would be understood by one skilled in the art, in some embodiments between about 0 psi and about 14.7 psi) for between about 5 minutes and about 24 hours (which can be repeated or extended as necessary). The pressure can be about 0 psi, about 1 psi, about 2 psi, about 3 psi, about 4 psi, about 5 psi, about 6 psi, about 7 psi, about 8 psi, about 9 psi, about 10 psi, about 11 psi, about 12 psi, about 13 psi, about 14 psi, or about 14.7 psi, or any range within two of these values, or any value or subrange between the range of 0 psi and about 14.7 psi. The time period can be between about 5 minutes and about 24 hours, in some embodiments about 5 minutes, about 30 minutes, about 60 minutes, about 90 minutes, about 8 hours, about 10 hours, about 12 hours, about 16 hours, or about 24 hours, or any range within two of these values, or any value or subrange between the range of 5 minutes and 24 hours. The concentration of the metal chelate, which is in the filtrate, can be between about 0.2 M and about 2 M, in some embodiments between about 0.4 M and about 1.0 M. In some embodiments, the concentration of the filtrate can be about 0.2M, about 0.3 M, about 0.4 M, about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M or about 2M, or any range within two of these values, or any value or subrange between the range of 0.2M and 2.0M. The UV-Vis (ultraviolet-visible) spectroscopy absorption wavelength of the filtrate comprising the metal chelate can be between about 280 nm and about 800 nm, in some embodiments about 506 nm. In some embodiments, the absorption of the filtrate comprising the metal chelate can be about 280 nm, about 300 nm, about 320 nm, about 340 nm, about 360 nm, about 380 nm, about 400 nm, about 410 nm, about 420 nm, about 430 nm, about 440 nm, about 450 nm, about 460 nm, about 470 nm, about 480 nm, about 490 nm, about 500 nm, about 510 nm, about 520 nm, about 530 nm, about 540 nm, about 550 nm, about 560 nm, about 570 nm, about 580 nm, about 590 nm, about 600 nm, about 610 nm, about 620 nm, about 630 nm, about 640 nm, about 650 nm, about 660 nm, about 670 nm, about 680 nm, about 690 nm, about 700 nm, about 710 nm, about 720 nm, about 730 nm, about 740 nm, about 750 nm, about 760 nm, about 770 nm, about 780 nm, about 790 nm, or about 800 nm, or any range within two of these values, or any value or subrange between the range of about 280 nm and about 800 nm.

An electrolyte solution can be made following the formation of the metal chelate. In some embodiments, the electrolyte solution can be formed from the filtrate by adjusting the concentration of the filtrate with a second solvent, which can be water (distilled, tap, or deionized, or combinations thereof).

The concentration of the electrolyte solution can be between about 0.4 M and about 2.0 M. In some embodiments, the electrolyte solution concentration can be about 0.4 M, about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 or about 2.0 M, or any range within two of these values, or any value or subrange between the range of about 0.4 M and about 2.0 M.

The solubility of the metal chelate can be altered with the inclusion of a solubility adjuster. In some embodiments, the solubility adjuster can include an aqueous fluid, for example water, with a surfactant. The surfactant can be dodecyl sulfate, ethylene glycol, alkylammonium salts (e.g. stearylammonium chloride), or combinations thereof. The amount of the solubility adjuster that can be added to the metal chelate (or electrolyte containing the metal chelate, or battery containing the metal chelate) can be adjusted as required to result in a solubility of between about 0.4 M and about 2.0 M, in some embodiments about 0.4 M, about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, about 2.0 M, or any range within two of these values, or any value or subrange between the range of about 0.4 M and about 2 M. Additionally, changing the cation or utilizing a mixture of cation counter ions can adjust the solubility of the metal chelate. Suitable counterions include K, Na, $NH_4$, Li, tetraethylammonium (TEA), tetrabutylammonium (TBA), or other tetraalkylammonium salts.

An aspect of the invention is an electrolyte. The electrolyte includes a solvent, at least one metal chelate, wherein the metal chelate dissolves in the solvent to form the electrolyte. The metal of the metal chelate is a transition metal, and the chelate of the metal chelate is PDTA, BDTA, DTPA, CyDTA, NTA, HEDTA, or EDTA.

In some embodiments, the solubility of the metal chelate can be altered by the nature of the counter cation(s). Altering the solubility can improve the energy density of the battery comprising the metal chelate. Suitable counter ions can include lithium, sodium, potassium, ammonium, TEA, TBA, mixed cations, or combinations thereof. The solubility of the metal chelate with the counter ion can be between about 0.4 M and about 2.0 M, in some embodiments about 0.4 M, about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, or about 2 M, or a range between two of these values, or any value or subrange between the range of 0.4 M and 2 M. Suitable combinations of counter ions and metal chelates are discussed below in Table 4.

In some embodiments, the coordination of the metal and the chelate of the metal chelate can vary depending on chelate, metal, and metal oxidation state. In some embodiments the metal can coordinate to the chelate such that the equilibrium constant between the metal chelate complex and the free metal ion and free chelate exceeds $10^{25}$. In other words, a virtually undetectable amount of unchelated metal ions exist in solution. In some embodiments, the chelate of the metal chelate can coordinate to the metal ion in amount between about 90% and about 100%, in some embodiments about 90%, about 91%, about 92%, about 93%, about 94%, about 95%, about 96%, about 97%, about 98%, about 99%, about 100%, or a range between two of these values, or any value or subrange between the range of 90% and 100%. By coordinating preferentially with the chelate, water ligand(s) are unable or can be less able to coordinate with the metal of the metal chelate. Water coordinating with the metal in the metal chelate can reduce the efficiency of the of the resulting battery. Further, excess chromium can form a precipitate, which can also reduce the efficiency of the resulting battery. Thus, an advantage aspect of the disclosure is that the chelate of the metal chelate preferentially coordinates with the metal ion. Metal chelates of the invention include, by way of example only, CrPDTA, CrBDTA, CrDTPA, CrNTA, CrCyDTA, CrHEDTA, CrEDTA, FePDTA, FeBDTA, FeDTPA, FeNTA, FeCyDTA, FeHEDTA, FeEDTA, V(PDTA), V(BDTA), V(DTPA), V(NTA), V(CyDTA), V(HEDTA), V(EDTA), Mn(PDTA), Mn(BDTA), MnDTPA, MnNTA, MnCyDTA, MnHEDTA, MnEDTA, CePDTA, CeBDTA, CeDTPA, CeNTA, CeCyDTA, CeHEDTA, CeEDTA, TiPDTA, TiBDTA, TiDTPA, TiNTA, TiCyDTA, TiEDTA, or TiHEDTA. The concentration of the metal chelate can be between about 0.1 M and about 2 M. In some embodiments, the concentration of the metal chelate can be about 0.1 M, about 0.5 M, about 1.0 M, about 1.5 M, about 2 M, or a range between two of these values, or any value or subrange between the range of about 0.1 M and about 2 M.

In some embodiments, the electrolyte can include a second metal. The second metal can be bismuth, lead, chelated lead, chelated bismuth, or a combination therein. The second metal can be soluble in the solvent. The solvent can be an aqueous fluid, for example water (distilled, tap, or deionized, or combinations thereof). Other solvents can include acetonitrile, tetrahydrofuran, 1,2-difluorobenzene, dimethylformamide, and combinations thereof. Second metals can be soluble when combined with the metal chelate until the material is contacted with the electrode in a flow battery. The second metal can then electrochemically deposit on the carbon electrode, which can enhance the electron transfer kinetics and thus improve battery performance. Other suitable solvents include acetonitrile, tetrahydrofuran, ortho-difluorobenzene, dimethylformamide, or combinations thereof.

In some embodiments, the electrolyte can include a second metal chelate, wherein the second metal chelate is different from the first metal chelate. In some embodiments, the metal of the first metal chelate and the metal of the second metal chelate can be the same or different. Second metal chelates can include PDTA, BDTA, DTPA, CyDTA, HEDTA, EDTA, or NTA. A counterion can be included with the second metal chelate. Suitable counterions include K, Na, NH$_4$, Li, tetraethylammonium (TEA), tetrabutylammonium (TBA), or other tetraalkylammonium salts.

The solubility of the second metal chelate with the second counter ion can be between about 0.4 M and about 2.0 M, in some embodiments about 0.4 M, about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, about 2.0 M, or any range within two of these values, or any value or subrange between the range of about 0.4 M and about 2 M. Additionally, changing the cation or utilizing a mixture of cation counter ions can adjust the solubility of the metal chelate.

An aspect of the invention is a flow battery. The anolyte of the flow battery includes at least one metal chelate. A metal of the metal chelate is a transition metal, and the chelate of the metal chelate is PDTA, BDTA, DTPA, CyDTA, HEDTA, EDTA, or NTA. The concentration of the metal chelate is greater than 0.8 M and less than or equal to 2.0 M. The flow battery also includes a catholyte. The flow battery also includes at least one electrode and at least one membrane that separates the anolyte and the catholyte.

An aspect of the invention is a flow battery. The anolyte of the flow battery includes a metal chelate. The metal of the metal chelate is a transition metal, and wherein the chelate is selected from the group consisting of PDTA, BDTA, DTPA, NTA, CyDTA, EDTA, or HEDTA. The catholyte includes Fe(CN)$_6$.

In some embodiments, the coordination of the metal and the chelate of the metal chelate can vary depending on chelate, metal, and metal oxidation state. In some embodiments the metal can coordinate to the chelate such that the equilibrium constant between the metal chelate complex and the free metal ion and free chelate exceeds $10^{25}$. In other words, a virtually undetectable amount of unchelated metal ions exist in solution. In some embodiments, the chelate of the metal chelate can coordinate to the metal ion in amount between about 90% and about 100%, in some embodiments about 90%, about 91%, about 92%, about 93%, about 94%, about 95%, about 96%, about 97%, about 98%, about 99%, about 100%, or a range between two of these values, or any value or subrange between the range of 90% and 100%. By coordinating preferentially with the chelate, water ligand(s) are unable or can be less able to coordinate with the metal of the metal chelate. Water coordinating with the metal in the metal chelate can reduce the efficiency of the of the resulting battery. Further, excess chromium can form a precipitate, which can also reduce the efficiency of the resulting battery. Thus, an advantage aspect of the disclosure is that the chelate of the metal chelate preferentially coordinates with the metal ion. Metal chelates of the invention include, by way of example only, CrPDTA, CrBDTA, CrDTPA, CrNTA, CrCyDTA, CrHEDTA, CrEDTA, FePDTA, FeBDTA, FeDTPA, FeNTA, FeCyDTA, FeHEDTA, FeEDTA, V(PDTA), V(BDTA), V(DTPA), V(NTA), V(CyDTA), V(HEDTA), V(EDTA), Mn(PDTA), Mn(BDTA), MnDTPA, MnNTA, MnCyDTA, MnHEDTA, MnEDTA, CePDTA, CeBDTA, CeDTPA, CeNTA, CeCyDTA, CeHEDTA, CeEDTA, TiPDTA, TiBDTA, TiDTPA, TiNTA, TiCyDTA, TiEDTA, or TiHEDTA. The concentration of the metal chelate can be between about 0.1 M and about 2 M. In some embodiments, the concentration of the metal chelate can be about 0.1 M, about 0.5 M, about 1.0 M, about 1.5 M, about 2 M, or a range between two of these values, or any value or subrange between the range of about 0.1 M and about 2 M.

In some embodiments, the metal chelate of the anolyte further comprises a counter ion. The counter ion can be lithium, sodium, potassium, ammonium, TEA, TBA, other tetraalkylammonium salts, mixed cations, or combinations thereof. Table 4 provides a number of counter ions, metal ions which complex with the chelate, and chelates. Each material listed in Table 4 can be combined unless otherwise noted.

TABLE 4

| Counter ions | Metal Ions | Chelate |
| --- | --- | --- |
| Na | Cr | PDTA |
| K | Fe | BDTA |
| Li | V | DTPA |
| NH$_4$ | Mn | NTA |

TABLE 4-continued

| Counter ions | Metal Ions | Chelate |
| --- | --- | --- |
| TEA | Ce | CyDTA |
| TBA | Ti | EDTA |
|  |  | HEDTA |

Non-limiting examples of the metal chelate with a counter ion include, by way of example only, NaCrPDTA, NaFePDTA, NaV(PDTA), NaMnPDTA, NaCePDTA, NaTiPDTA, KCrPDTA, KFePDTA, KV(PDTA), KMnPDTA, KCePDTA, KTiPDTA, LiCrPDTA, LiFePDTA, LiV(PDTA), LiMnPDTA, LiCePDTA, LiTiPDTA, NH$_4$CrPDTA, NH$_4$FePDTA, NH$_4$V(PDTA), NH$_4$MnPDTA, NH$_4$CePDTA, NH$_4$TiPDTA, (TEA)CrPDTA, (TEA)FePDTA, (TEA)V(PDTA), (TEA)MnPDTA, (TEA)CePDTA, (TEA)TiPDTA, (TBA)CrPDTA, (TBA)FePDTA, (TBA)V(PDTA), (TBA)MnPDTA, (TBA)CePDTA, (TBA)TiPDTA, NaCrBDTA, NaFeBDTA, NaV(BDTA), NaMnBDTA, NaCeBDTA, NaTiBDTA, KCrBDTA, KFeBDTA, KV(BDTA), KMnBDTA, KCeBDTA, KTiBDTA, LiCrBDTA, LiFeBDTA, LiV(BDTA), LiMnBDTA, LiCeBDTA, LiTiBDTA, NH$_4$CrBDTA, NH$_4$FeBDTA, NH$_4$V(BDTA), NH$_4$MnBDTA, NH$_4$CeBDTA, NH$_4$TiBDTA, (TEA)CrBDTA, (TEA)FeBDTA, (TEA)V(BDTA), (TEA)MnBDTA, (TEA)CeBDTA, (TEA)TiBDTA, (TBA)CrBDTA, (TBA)FeBDTA, (TBA)V(BDTA), (TBA)MnBDTA, (TBA)CeBDTA, (TBA)TiBDTA, NaCrDTPA, NaFeDTPA, NaV(DTPA), NaMnDTPA, NaCeDTPA, NaTiDTPA, KCrDTPA, KFeDTPA, KV(DTPA), KMnDTPA, KCeDTPA, KTiDTPA, LiCrDTPA, LiFeDTPA, LiV(DTPA), LiMnDTPA, LiCeDTPA, LiTiDTPA, NH$_4$CrDTPA, NH$_4$FeDTPA, NH$_4$V(DTPA), NH$_4$MnDTPA, NH$_4$CeDTPA, NH$_4$TiDTPA, (TEA)CrDTPA, (TEA)FeDTPA, (TEA)V(DTPA), (TEA)MnDTPA, (TEA)CeDTPA, (TEA)TiDTPA, (TBA)CrDTPA, (TBA)FeDTPA, (TBA)V(DTPA), (TBA)MnDTPA, (TBA)CeDTPA, (TBA)TiDTPA, NaCrNTA, NaFeNTA, NaV(NTA), NaMnNTA, NaCeNTA, NaTiNTA, KCrNTA, KFeNTA, KV(NTA), KMnNTA, KCeNTA, KTiNTA, LiCrNTA, LiFeNTA, LiV(NTA), LiMnNTA, LiCeNTA, LiTiNTA, NH$_4$CrNTA, NH$_4$FeNTA, NH$_4$V(NTA), NH$_4$MnNTA, NH$_4$CeNTA, NH$_4$TiNTA, (TEA)CrNTA, (TEA)FeNTA, (TEA)V(NTA), (TEA)MnNTA, (TEA)CeNTA, (TEA)TiNTA, (TBA)CrNTA, (TBA)FeNTA, (TBA)V(NTA), (TBA)MnNTA, (TBA)CeNTA, (TBA)TiNTA, NaCr(CYDTA), NaFe(CYDTA), NaV(CYDTA), NaMn(CYDTA), NaCe(CYDTA), NaTi(CYDTA), KCr(CYDTA), KFe(CYDTA), KV(CYDTA), KMn(CYDTA), KCe(CYDTA), KTi(CYDTA), LiCr(CYDTA), LiFe(CYDTA), LiV(CYDTA), LiMn(CYDTA), LiCe(CYDTA), LiTi(CYDTA), NH$_4$Cr(CYDTA), NH$_4$Fe(CYDTA), NH$_4$V(CYDTA), NH$_4$Mn(CYDTA), NH$_4$Ce(CYDTA), NH$_4$Ti(CYDTA), (TEA)Cr(CYDTA), (TEA)Fe(CYDTA), (TEA)V(CYDTA), (TEA)Mn(CYDTA), (TEA)Ce(CYDTA), (TEA)Ti(CYDTA), (TBA)Cr(CYDTA), (TBA)Fe(CYDTA), (TBA)V(CYDTA), (TBA)Mn(CYDTA), (TBA)Ce(CYDTA), (TBA)Ti(CYDTA), NaCrEDTA, NaFeEDTA, NaV(EDTA), NaMnEDTA, NaCeEDTA, NaTiEDTA, KCrEDTA, KFeEDTA, KV(EDTA), KMnEDTA, KCeEDTA, KTiEDTA, LiCrEDTA, LiFeEDTA, LiV(EDTA), LiMnEDTA, LiCeEDTA, LiTiEDTA, NH$_4$CrEDTA, NH$_4$FeEDTA, NH$_4$V(EDTA), NH$_4$MnEDTA, NH$_4$CeEDTA, NH$_4$TiEDTA, (TEA)CrEDTA, (TEA)FeEDTA, (TEA)V(EDTA), (TEA)MnEDTA, (TEA)CeEDTA, (TEA)TiEDTA, (TBA)CrEDTA, (TBA)FeEDTA, (TBA)V(EDTA), (TBA)MnEDTA, (TBA)CeEDTA, (TBA)TiEDTA, NaCrHEDTA, NaFeHEDTA, NaV(HEDTA), NaMnHEDTA, NaCeHEDTA, NaTiHEDTA, KCrHEDTA, KFeHEDTA, KV(HEDTA), KMnHEDTA, KCeHEDTA, KTiHEDTA, LiCrHEDTA, LiFeHEDTA, LiV(HEDTA), LiMnHEDTA, LiCeHEDTA, LiTiHEDTA, NH$_4$CrHEDTA, NH$_4$FeHEDTA, NH$_4$V(HEDTA), NH$_4$MnHEDTA, NH$_4$CeHEDTA, NH$_4$TiHEDTA, (TEA)CrHEDTA, (TEA)FeHEDTA, (TEA)V(HEDTA), (TEA)MnHEDTA, (TEA)CeHEDTA, (TEA)TiHEDTA, (TBA)CrHEDTA, (TBA)FeHEDTA, (TBA)V(HEDTA), (TBA)MnHEDTA, (TBA)CeHEDTA, or (TBA)TiHEDTA.

In some embodiments, the catholyte can include a second metal chelate. The metal of the second metal chelate can be a transition metal and the chelate of the second metal chelate can be PDTA, BDTA, DTPA, EDTA, CyDTA, HEDTA, or NTA. The second chelate can be the same or different from the first chelate. The second metal chelate can include a second metal which is different from the metal of the metal chelate of the anolyte. The ratio of the first metal chelate to the second metal chelate in the catholyte can be between about 100:1 and about 1:1, about 100:1, about 90:1, about 80:1, about 70:1, about 60:1, about 50:1, about 40:1, about 30:1, about 20:1, about 10:1, about 5:1, about 2:1 or about 1:1, or any range within two of these values, or any value or subrange between the range of about 100:1 and about 1:1. Like the first metal chelate, the second metal chelate can include a counter ion.

In some embodiments, the catholyte can include a counter ion. The counter ion of the catholyte can be the same as the counter ion of the anolyte in the flow battery. The pH of the catholyte and the pH of the anolyte can be between about 6 and about 11. In some embodiments, the pH can be about 6, about 7, about 8, about 9, about 10, about 11, or any range within two of these values, or any value or subrange between the range of about 6 and about 11 pH. In some embodiments, the catholyte can be $K_4[Fe(CN)_6]$, a metal chelate include BDTA or PDTA as the chelate, for example $K_2[Mn(BDTA)]$, a metal chelate include EDTA as the chelate, for example $K[Cr(EDTA)]$, or $Br_2/Br^-$.

The battery can include a buffer. Suitable buffers include borate, NaOAc, NaHCO$_3$, K$_2$B$_4$O$_7$, K$_2$HPO$_4$, Na$_2$B$_4$O$_7$, uncomplexed BDTA, uncomplexed CyDTA, uncomplexed EDTA, uncomplexed NTA, uncomplexed PDTA, a phosphate ion, a borate ion, and combinations thereof. The buffer can be maintained in the electrolyte of the battery. The buffer can be at a pH between about 6 and about 11. The concentration of the buffer can be between about 1 mM and about 1.0 M.

In some embodiments, the catholyte of the battery can include Fe(CN)$_6$ or Br$_2$/Br$^-$. The concentration of the catholyte when it is Fe(CN)$_6$ can be between about 0.01 M and about 1.5 M. The concentration of the cathode when it is Br$_2$/Br$^-$ is between about 0.01 M and about 5.7 M. The pH of the catholyte can be between about 3 and about 14. In some embodiments, metal chelates can be used for the anolyte and Fe(CN)$_6$ is used at the catholyte.

Unlike prior art batteries which are unstable, the disclosure provides a high voltage and unprecedented stability. A voltage efficiency of the flow battery can be between about 80% and about 95%. In some embodiments, the voltage efficiency of the flow battery can be about 80%, about 85%, about 90%, about 95%, or any range within two of these values, or any value or subrange between the range of about 80% and about 95%. In some embodiments, the overall efficiency of the flow battery can be between about 75% and about 95%. In some embodiments, the efficiency of the flow battery can be about 75%, about 80%, about 85%, about 90% or about 95%, or any range within two of these values, or any value or subrange between the range of about 75% and about 95%. In some embodiments, less than about 5% of state of charge of the battery is lost per day in the flow battery. In some embodiments, the hydrogen evolution of the battery can be less than about 5% after 24 hours. In some embodiments, the hydrogen evolution of the battery can be about 5%, about 4%, about 3%, about 2%, about 1% or about 0%, or any range within two of these values, or any value or subrange between the range of about 0% and about 5%, after between about 0 minutes (no hydrogen generation) and about 24 hours, in some embodiments about 0 minutes, about 10 minutes, about 30 minutes, about 1 hour, about 1.5 hours, about 2 hours, about 2.5 hours, about 3 hours, about 3.5 hours, about 4 hours, about 4.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours, or any range within two of these values, or any value or subrange between the range of about 0 minutes and about 24 hours. Furthermore, in some embodiments, the state-of-charge of the battery decreases by less than 10% (in some embodiments between about 0% and about 10%, about 0%, about 1%, about 2%, about 3%, about 4%, about 5%, about 6%, about 7%, about 8%, about 9%, or about 10%, or any range within two of these values, or any value or subrange between the range of about 0% and about 10%) after one week (in some embodiments between about 1 hour and about 7 days, or about 1 hour, about 2 hours, about 8 hours, about 12 hours, about 24 hours, about 1.5 days, about 2 days, about 2.5 days, about 3 days, about 3.5 days, about 4 days, about 4.5 days, about 5 days, about 5.5 days, about 6 days, about 6.5 days, or about 7 days, or any range within two of these values, or any value or subrange between the range of about 1 hour and about 7 days) of storage at 20° C. (in some embodiments, about −20° C. and about 20° C., about −20° C., about −15° C., about −10° C., about −5° C., about 0° C., about 5° C., about 10° C., about 15° C., or about 20° C., or any range within two of these values, or any value or subrange between the range of about −20° C. and about 20° C.) and atmospheric pressure (about 1 atm at sea level, or equivalent at different altitudes as would be understood by one skilled in the art).

The membrane of the flow battery can be a cation exchange membrane. The cation exchange membrane can be beneficial in the system as the metal chelate in the anolyte and the catholyte of the disclosure can both be negatively charged, even when dissolved in water or acid. As a result of the negative charge and/or the large size of the metal chelates, transfer of the metal chelates through the membrane can be reduced compared to systems where the active metal materials are positively charged. In some embodiments, the cation exchange membrane can be a sulfonated tetrafluoroethylene based fluoropolymer-copolymer (e.g. Nafion®), sulfonated PEEK, or other similar material. Other suitable membranes can include Fumapem F-930 RFS, Nafion® 211, or Nafion® 212. It should be appreciated by those skilled in the art that this electrolyte chemistry is compatible with many different cation and anion exchange membranes as well as size exclusion membranes, porous separators, etc.

Suitable electrodes include carbon paper, carbon felt, carbon cloth, carbon fiber, and combinations thereof.

The anolyte or the catholyte can further include a second metal. The second metal can be added the electrolyte to plate at least a portion of the electrode. In some embodiments, at least about 1 µg/cm$^2$ of the electrode can be plated with the second metal. In some embodiments, between about 0.1 µg/cm$^2$ and about 100 µg/cm$^2$ of the electrode can be plated with the second metal. The second metal can be bismuth, lead, chelated lead, chelated bismuth, or a combination therein. The second metal can be soluble in the solvent. The solvent can be an aqueous fluid, for example water (distilled, tap, or deionized, or combinations thereof). Other solvents can include acetonitrile, tetrahydrofuran, 1,2-difluorobenzene, dimethylformamide, and combinations thereof. Second metals can be soluble when combined with the metal chelate until the material is contacted with the electrode in a flow battery. The second metal can then electrochemically deposit on the carbon electrode, which can enhance the electron transfer kinetics and thus improve battery performance. Other suitable solvents include acetonitrile, tetrahydrofuran, ortho-difluorobenzene, dimethylformamide, or combinations thereof. The second metal can be soluble in the anolyte and/or catholyte.

The concentration of the metal chelate is between about 0.1 M and about 2 M. In some embodiments, the concentration of the metal chelate can be about 0.1 M, about 0.5M, about 1.0 M, about 1.1 M, about 1.2 M, about 1.3 M, about 1.4 M, about 1.5 M, about 1.6 M, about 1.7 M, about 1.8 M, about 1.9 M, or about 2 M, or any range within two of these values, or any value or subrange between the range of about 1.0 M and about 2 M. As a result, the size of the battery can be reduced by up to about 5 times the size of prior art batteries. In comparison, the concentration of NaCrEDTA as shown in WO2012117594 can be run at a maximum of about 0.4 M, resulting in an increased size of the battery.

In some embodiments, the current efficiency of the battery can be between 10% and about 100%. In some embodiments, the efficiency can be about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, or any range within two of these values, or any value or subrange between the range of about 10% and about 100%.

The maximum state of charge of the battery can be between about 80% and about 100%. In some embodiments, the maximum state of charge of the battery can be about 80%, about 83%, about 84%, about 85%, about 90%, about 95%, or about 100%, or any range within two of these values, or any value or subrange between the range of about 0% and about 100%, The voltage of the battery can be between about 1 V and about 2.2 V. In some embodiments, the voltage of the battery can be between about 1 V, about 1.1 V, about 1.2 V, about 1.3 V, about 1.4 V, about 1.5 V, about 1.6 V, about 1.7 V, about 1.8 V, about 1.9 V, about 2.0 V, about 2.1 V, or about 2.2V, or any range within two of these values, or any value or subrange between the range of about 1 V and about 2.2 V.

Membranes in the flow battery can include Fumapem F-930 RFS, Nafion 211, Nafion 212, sulfonated PEEK, and combinations thereof.

An aspect of the invention is a flow battery. The flow battery includes two electrolytes, comprising an anolyte and a catholyte. The electrolyte includes a buffer at a pH between about 6 and about 11. The buffer can be a phosphate ion, borate ion, NTA, an uncomplexed organic material, or combinations thereof. The uncomplexed organic material can be EDTA, BDTA, PDTA, CyDTA, DTPA, HEDTA, or NTA. The buffer is maintained in the battery. The anolyte includes a metal chelate. A metal of the metal chelate is a transition metal, and the chelate of the metal chelate is EDTA. In some embodiments, the flow battery can also include an electrode and a membrane that separates the anolyte and the catholyte. The current efficiency of the battery (electrons in compared to the electrons out) can be greater than 60%.

In some embodiments, the coordination of the metal and the chelate of the metal chelate can vary depending on chelate, metal, and metal oxidation state. In some embodiments the metal can coordinate to the chelate such that the equilibrium constant between the metal chelate complex and the free metal ion and free chelate exceeds $10^{25}$. In other words, a virtually undetectable amount of unchelated metal ions exist in solution. In some embodiments, the chelate of the metal chelate can coordinate to the metal ion in amount between about 90% and about 100%, in some embodiments about 90%, about 91%, about 92%, about 93%, about 94%, about 95%, about 96%, about 97%, about 98%, about 99%, about 100%, or a range between two of these values, or any value or subrange between the range of 90% and 100%. By coordinating preferentially with the chelate, water ligand(s) are unable or can be less able to coordinate with the metal of the metal chelate. Water coordinating with the metal in the metal chelate can reduce the efficiency of the of the resulting battery. Further, excess chromium can form a precipitate, which can also reduce the efficiency of the resulting battery. Thus, an advantage aspect of the disclosure is that the chelate of the metal chelate preferentially coordinates with the metal ion. Metal chelates of the invention include, by way of example only, CrPDTA, CrBDTA, CrDTPA, CrNTA, CrCyDTA, CrHEDTA, CrEDTA, FePDTA, FeBDTA, FeDTPA, FeNTA, FeCyDTA, FeHEDTA, FeEDTA, V(PDTA), V(BDTA), V(DTPA), V(NTA), V(CyDTA), V(HEDTA), V(EDTA), Mn(PDTA), Mn(BDTA), MnDTPA, MnNTA, MnCyDTA, MnHEDTA, MnEDTA, CePDTA, CeBDTA, CeDTPA, CeNTA, CeCyDTA, CeHEDTA, CeEDTA, TiPDTA, TiBDTA, TiDTPA, TiNTA, TiCyDTA, TiEDTA, or TiHEDTA. The concentration of the metal chelate can be between about 0.1 M and about 2 M. In some embodiments, the concentration of the metal chelate can be about 0.1 M, about 0.5 M, about 1.0 M, about 1.5 M, about 2 M, or a range between two of these values, or any value or subrange between the range of about 0.1 M and about 2 M.

In some embodiments, the metal chelate of the anolyte further comprises a counter ion. The counter ion can be lithium, sodium, potassium, ammonium, TEA, TBA, other tetraalkylammonium salts, mixed cations, or combinations thereof. Table 4 provides a number of counter ions, metal ions which complex with the chelate, and chelates.

In some embodiments, the catholyte can include a second metal chelate. The metal of the second metal chelate can be a transition metal and the chelate of the second metal chelate can be PDTA, BDTA, DTPA, EDTA, CyDTA, HEDTA, or NTA. The second chelate can be the same or different from the first chelate. The second metal chelate can include a second metal which is different from the metal of the metal chelate of the anolyte. The ratio of the first metal chelate to the second metal chelate in the catholyte can be between about 100:1 and about 1:1, about 100:1, about 90:1, about 80:1, about 70:1, about 60:1, about 50:1, about 40:1, about 30:1, about 20:1, about 10:1, about 5:1, about 2:1 or about 1:1, or any range within two of these values, or any value or subrange between the range of about 100:1 and about 1:1. Like the first metal chelate, the second metal chelate can include a counter ion.

In some embodiments, the catholyte can include a counter ion. The counter ion of the catholyte can be the same as the counter ion of the anolyte in the flow battery. The pH of the catholyte and the pH of the anolyte can be between about 6 and about 11. In some embodiments, the pH can be about 6, about 7, about 8, about 9, about 10, about 11, or any range within two of these values, or any value or subrange between the range of about 6 and about 11 pH. In some embodiments, the catholyte can be $K_4[Fe(CN)_6]$, a metal chelate include BDTA or PDTA as the chelate, for example $K_2[Mn(BDTA)]$, a metal chelate include EDTA as the chelate, for example $K[Cr(EDTA)]$, or $Br_2/Br^-$.

The battery can include a buffer. Suitable buffers include borate, NaOAc, $NaHCO_3$, $K_2B_4O_7$, $K_2HPO_4$, $Na_2B_4O_7$, uncomplexed BDTA, uncomplexed CyDTA, uncomplexed EDTA, uncomplexed NTA, uncomplexed PDTA, a phosphate ion, a borate ion, and combinations thereof. The buffer can be maintained in the electrolyte of the battery. The buffer can be at a pH between about 6 and about 11. The concentration of the buffer can be between about 1 mM and about 1.0 M.

In some embodiments, the catholyte of the battery can include $Fe(CN)_6$ or $Br_2/Br^-$. The concentration of the catholyte when it is $Fe(CN)_6$ can be between about 0.01 M and about 1.5 M. The concentration of the cathode when it is $Br_2/Br^-$ is between about 0.01 M and about 5.7 M. The pH of the catholyte can be between about 3 and about 14. In some embodiments, metal chelates can be used for the anolyte and $Fe(CN)_6$ is used at the catholyte.

Unlike prior art batteries which are unstable, the disclosure provides a high voltage and unprecedented stability. A voltage efficiency of the flow battery can be between about 80% and about 95%. In some embodiments, the voltage efficiency of the flow battery can be about 80%, about 85%, about 90%, about 95%, or any range within two of these values, or any value or subrange between the range of about 80% and about 95%. In some embodiments, the overall efficiency of the flow battery can be between about 75% and about 95%. In some embodiments, the efficiency of the flow battery can be about 75%, about 80%, about 85%, about 90% or about 95%, or any range within two of these values, or any value or subrange between the range of about 75% and about 95%. In some embodiments, less than about 5% of state of charge of the battery is lost per day in the flow battery. In some embodiments, the hydrogen evolution of the battery can be less than about 5% after 24 hours. In some embodiments, the hydrogen evolution of the battery can be about 5%, about 4%, about 3%, about 2%, about 1% or about 0%, or any range within two of these values, or any value or subrange between the range of about 0% and about 5%, after between about 0 minutes (no hydrogen generation) and about 24 hours, in some embodiments about 0 minutes, about 10 minutes, about 30 minutes, about 1 hour, about 1.5 hours, about 2 hours, about 2.5 hours, about 3 hours, about 3.5 hours, about 4 hours, about 4.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours, or any range within two of these values, or any value or subrange between the range of about 0 minutes and about 24 hours. Furthermore, in some embodiments, the state-of-charge of the battery decreases by less than 10% (in some embodiments between about 0% and about 10%, about 0%, about 1%, about 2%, about 3%, about 4%, about 5%, about 6%, about 7%, about 8%, about 9%, or about 10%, or any range within two of these values, or any value or subrange between the range of about 0% and about 10%) after one week (in some embodiments between about 1 hour and about 7 days, or about 1 hour, about 2 hours, about 8 hours, about 12 hours, about 24 hours, about 1.5 days, about 2 days, about 2.5 days, about 3 days, about 3.5 days, about 4 days, about 4.5 days, about 5 days, about 5.5 days, about 6 days, about 6.5 days, or about 7 days, or any range within two of these values, or any value or subrange between the range of about 1 hour and about 7 days) of storage at 20° C. (in some embodiments, about −20° C. and about 20° C., about −20° C., about −15° C., about −10° C., about −5° C., about 0° C., about 5° C., about 10° C., about 15° C., or about 20° C., or any range within two of these values, or any value or subrange between the range of about −20° C. and about 20° C.) and atmospheric pressure (about 1 atm at sea level, or equivalent at different altitudes as would be understood by one skilled in the art).

The membrane of the flow battery can be a cation exchange membrane. The cation exchange membrane can be beneficial in the system as the metal chelate in the anolyte and the catholyte of the disclosure can both be negatively charged, even when dissolved in water or acid. As a result of the negative charge and/or the large size of the metal chelates, transfer of the metal chelates through the membrane can be reduced compared to systems where the active metal materials are positively charged. In some embodiments, the cation exchange membrane can be a sulfonated tetrafluoroethylene based fluoropolymer-copolymer (e.g. Nafion®), sulfonated PEEK, or other similar material. Other suitable membranes can include Fumapem F-930 RFS, Nafion® 211, or Nafion® 212. It should be appreciated by those skilled in the art that this electrolyte chemistry is compatible with many different cation and anion exchange membranes as well as size exclusion membranes, porous separators, etc.

Suitable electrodes include carbon paper, carbon felt, carbon cloth, carbon fiber, and combinations thereof.

The anolyte or the catholyte can further include a second metal. The second metal can be added the electrolyte to plate at least a portion of the electrode. In some embodiments, at least about 1 µg/cm$^2$ of the electrode can be plated with the second metal. In some embodiments, between about 0.1 µg/cm$^2$ and about 100 µg/cm$^2$ of the electrode can be plated with the second metal. The second metal can be bismuth, lead, chelated lead, chelated bismuth, or a combination therein. The second metal can be soluble in the solvent. The solvent can be an aqueous fluid, for example water (distilled, tap, or deionized, or combinations thereof). Other solvents can include acetonitrile, tetrahydrofuran, 1,2-difluorobenzene, dimethylformamide, and combinations thereof. Second metals can be soluble when combined with the metal chelate until the material is contacted with the electrode in a flow battery. The second metal can then electrochemically deposit on the carbon electrode, which can enhance the electron transfer kinetics and thus improve battery performance. Other suitable solvents include acetonitrile, tetrahydrofuran, ortho-difluorobenzene, dimethylformamide, or combinations thereof. The second metal can be soluble in the anolyte and/or catholyte.

The concentration of the metal chelate is between about 0.1 M and about 2 M. In some embodiments, the concentration of the metal chelate can be about 0.1 M, about 0.5M, about 1.0 M, about 1.1 M, about 1.2 M, about 1.3 M, about 1.4 M, about 1.5 M, about 1.6 M, about 1.7 M, about 1.8 M, about 1.9 M, or about 2 M, or any range within two of these values, or any value or subrange between the range of about 1.0 M and about 2 M. As a result, the size of the battery can be reduced by up to about 5 times the size of prior art batteries. In comparison, the concentration of NaCrEDTA as shown in WO2012117594 can be run at a maximum of about 0.4 M, resulting in an increased size of the battery.

In some embodiments, the current efficiency of the battery can be between 10% and about 100%. In some embodiments, the efficiency can be about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, or any range within two of these values, or any value or subrange between the range of about 10% and about 100%.

The maximum state of charge of the battery can be between about 80% and about 100%. In some embodiments, the maximum state of charge of the battery can be about 80%, about 83%, about 84%, about 85%, about 90%, about 95%, or about 100%, or any range within two of these values, or any value or subrange between the range of about 0% and about 100%, The voltage of the battery can be between about 1 V and about 2.2 V. In some embodiments, the voltage of the battery can be between about 1 V, about 1.1 V, about 1.2 V, about 1.3 V, about 1.4 V, about 1.5 V, about 1.6 V, about 1.7 V, about 1.8 V, about 1.9 V, about 2.0 V, about 2.1 V, or about 2.2V, or any range within two of these values, or any value or subrange between the range of about 1 V and about 2.2 V.

In some embodiments, the catholyte can include a metal chelate. The metal of the metal chelate can be a transition metal, and the chelate can be selected from the group consisting of EDTA, BDTA, PDTA, CyDTA, DTPA, HEDTA, or NTA.

Membranes in the flow battery can include Fumapem F-930 RFS, Nafion 211, Nafion 212, sulfonated PEEK, and combinations thereof.

An aspect of the disclosure is a method to plate an electrode. The method includes dissolving a plating material in a solution. The solution is an electrolyte. Advantageously, the plating material can be plated on an electrode in a flow battery without disassembling to the flow battery. In other words, the electrode can be plated while present in the flow battery. The electrode can be a carbon paper, carbon cloth, carbon felt, carbon fiber, or combinations thereof. The plating material can be bismuth, lead, chelated bismuth, or chelated lead, and combinations thereof. The plating material can be soluble in an electrolyte of the flow battery.

In some embodiments, at least about 1 µg/cm$^2$ of the electrode can be plated with the plating material. In some embodiments, between about 0.1 µg/cm$^2$ and about 100 µg/cm$^2$ of the electrode can be plated with the plating material. The plating material can be bismuth, lead, chelated lead, chelated bismuth, or a combination therein. The plating material metal can be soluble in the solvent. The solvent can be an aqueous fluid, for example water (distilled, tap, or deionized, or combinations thereof). Other solvents can include acetonitrile, tetrahydrofuran, 1,2-difluorobenzene, dimethylformamide, and combinations thereof. Furthermore, the plating material can be soluble when combined with the metal chelate until the material is contacted with the electrode in a flow battery. The plating material can then electrochemically deposit on the carbon electrode, which can enhance the electron transfer kinetics and thus improve battery performance. Suitable solvents can include, but are not limited to, acetonitrile, tetrahydrofuran, ortho-difluorobenzene, dimethylformamide, or combinations thereof.

Suitable electrolytes are discussed throughout the Specification and can be used in the method to plate an electrode.

EXAMPLES

Example 1

Method of Forming the Metal Chelate

Complexes can be synthesized via several different methods. The following examples are provided to illustrate procedures that could be used to synthesize the described materials. Other methods, including the use of $Cr_2O_3$ or $Cr(OH)_3$, can be used to synthesize the same complexes.

K[Cr(PDTA)] was prepared via the following procedure by dissolving $KCr(SO_4)_2 \cdot 12H_2O$ (40 g, 80 mmol, Acros, 98+%) and 1,3-diaminopropane-N,N,N',N'-tetraacetic acid (27.5 g, 90 mmol, Sigma Aldrich, 99%) in 30 mL of deionized water and heating the mixture to 110° C. After 1 hour of heating, solid KOH (10 g) was added in 0.5 g increments every 15 seconds. After 24 hours, 16 mL of 5 M KOH was added slowly in 1 mL increments. Another 16 mL of 5 M KOH was added after an additional 24 hours of heating. The pH of the solution was monitored during the addition of KOH and kept under 2.5 until after 48 hours of heating. After 72 hours of total reaction time, the final solution pH was between 5 and 6. The solution was cooled to room temperature, and 95 mL of acetone was added, precipitating solid $K_2SO_4$, which was removed by filtration. The filtrate was concentrated under reduced pressure to produce a stock solution. The concentration of K[Cr(PDTA)] was assessed by absorption spectroscopy using the absorbance at 506 nm ($\varepsilon$=116 $M^{-1}$ $cm^{-1}$).

Method to Form the Electrolyte

The flow cell was run at concentrations of 0.4 M and 1.0 M K[Cr(PDTA)]. 0.4 M K[Cr(PDTA)] solutions were created by diluting the stock solution with DI water to 10 mL and adding $K_2B_4O_7 \cdot 4H_2O$ (0.6 g, 2 mmol) to yield an electrolyte containing 0.4 M K[Cr(PDTA)] and 0.2 M $K_2B_4O_7$ at pH 9.5. 1.0 M K[Cr(PDTA)] solutions were created by diluting saturated K[Cr(PDTA)] at 40° C. with DI water to 10 mL and adding $K_2B_4O_7 \cdot 4H_2O$ (0.3 g, 1 mmol) to yield an electrolyte containing 1.0 M K[Cr(PDTA)] and 0.1 M $K_2B_4O_7$ at pH 9.0.

Analysis

Half-Cell Measurements

Cyclic voltammetry was conducted using a Gamry Interface 1000 potentiostat, an Ag/AgCl aqueous reference electrode (3 M NaCl filling solution), a Pt wire counter electrode, and a 3-mm-diameter glassy carbon electrode. Half-cell experiments were conducted on a solution containing 5 mM K[Cr(PDTA)], 5 mM $K_4Fe(CN)_6$, and 0.125 M $K_2B_4O_7$ at pH 9.

Kinetics Calculations

For an irreversible reaction, the peak current, $i_p$, is given by equation (1).

$$i_p = 0.4958 nFAC_O^0 D_O^{1/2} v^{1/2} \left[ \frac{\alpha n_a F}{RT} \right]^{1/2} \qquad (1)$$

where $i_p$ is in amperes, A is the electrode area ($cm^2$), $C_O^0$ is the bulk concentration of oxidant (moles $cm^{-3}$), v is the potential sweep rate (V $s^{-1}$), $D_O$ is the diffusion coefficient of the oxidant, $\alpha$ is the charge transfer coefficient, and $n_a$ is the number of electrodes involved in the rate-determining step. This equation reduces, at 25° C. to equation (2).

$$i_p = 2.99 \ast 10^5 n(\alpha n_a)^{1/2} AC_O^0 D_O^{1/2} v^{1/2} \qquad (2)$$

$i_p$ vs. $v^{1/2}$ was plotted, giving a straight line, with the slope being proportional to $D_O$. Assuming an $\alpha n_a$ value of ½ allowed for the solving of $D_O$. For a totally irreversible peak, the peak potential, Ep, is a function of scan rate, the difference between Ep and the formal potential, $E^{0'}$, being related to the standard heterogeneous rate constant, $k^\circ$. The peak current can be expressed as show in equation (3).

$$i_p = 0.227 nFAC_O^0 \exp\left[-\frac{(\alpha n_a F)}{(RT)}(E_p - E^{0'})\right] \qquad (3)$$

$Ln(i_p)$ vs. ($E_p - E^{0'}$), at different scan rates was plotting, with the intercept being proportional to and allowing solving for $k^\circ$. $E^{0'}$ was found in literature to be −1.31 V vs Ag/AgCl. The bulk concentration was 0.005 M, and $n_a$ was 1 as there is only 1 electron being transferred. The area of the electrode is 0.0707 $cm^2$ from a 3 mm diameter glassy carbon electrode. Scan rates were done at 25, 50, 100, 200, and 500 mV $s^{-1}$. The slope of $i_p$ vs. $v^{1/2}$ was 0.0747, and the intercept of $ln(i_p)$ vs. ($E_p - E^{0'}$) was −13.527.

From these equations, equations (4) and (5) were determined.

$$k_o = 1.7 \times 10^{-4} \text{ cm s}^{-1} \qquad (4)$$

$$D_o = 6.2 \times 10^{-6} \text{ cm}^2 \text{ s}^{-1} \qquad (5)$$

Flow Cell Apparatus

A 5 $cm^2$ single-cell flow battery was purchased from Fuel Cell Technologies Inc. with the acid cell configuration, so that the tubing carrying the electrolyte feeds directly into the graphite flow plate without contacting the aluminum or stainless-steel cell components. The flow plates comprised Poco graphite blocks with 5 $cm^2$ single serpentine flow fields. The $K_4Fe(CN)_6$ electrolyte was placed in a 100 mL round bottom flask fitted with a rubber septum with holes drilled for ⅛" OD perfluroacetoxy (PFA) inlet/outlet tubing and pumped into and out of the flow cell with a gear pump (Cole-Parmer) and using ⅛" OD, 1/16" ID PFA tubing and PFA fittings.

Due to the sensitivity of the K[Cr(PDTA)] and $Br_a$ solutions to stainless steel, a PTFE diaphragm pump (Cole-Parmer) was used for these electrolytes. Due to the pulsing flow of the diaphragm pump, polarization data (current-voltage) generated a sinusoidal response to the pulsed fluid flow and mass transport limitations within the cell. Polarization plots and power density plots in FIGS. 2B, 2C, 3A, 3B were fitted to selected points on the graph associated with the peak current, as this reflects the cell performance in the absence of mass transport limitations imposed by the pulsed flow. The complete data with fits are shown in FIGS. 9C, 9D, 10C, and 10D, which illustrates chromium-ion cycling plots.

A Nafion 212 membrane (50 µm thick) was soaked in DI water for 12 hours and gasketed with a 0.002" PTFE sheet. Five stacked sheets (280 µm thick and 5 cm$^2$ each) of GDL 39 AA carbon paper (SGL) were heated to 150° C. for 12 hours and used on each side with a 0.04" PTFE gasket providing 38% compression. The cell was bolted together and tightened with a torque wrench to 10 Nm. Flow cell experiments were conducing using a Gamry Interface 5000E potentiostat/galvanostat. The K[Cr(PDTA)] and KBr solutions were pumped at a flow rate of 42 mL/min using the PTFE-diaphragm pumps and the Fe(CN)$_6$ solution was pumped at a flow rate of 50 mL/min using the gear pump.

Flow Battery Experiments 0.4 M CrPDTA flow cell experiments on the negative side of the cell 10 mL of 0.4 M KCrPDTA and 0.2 M potassium tetraborate were used as the electrolyte, while on the positive side of the cell 50 mL of 0.3 M K$_4$Fe(CN)$_6$, 0.45 M K$_3$Fe(CN)$_6$, and 0.025 M potassium tetraborate were used as the electrolyte solution in the fully discharged state. The solutions were contained in 100 mL glass round bottom flasks at room temperature. The CrPDTA solution was purged with argon for one hour before cycling began and was kept under positive argon pressure during the experiment.

1.0 M CrPDTA flow cell experiments on the negative side of the cell 10 mL of a 1.0 M Cr$^{3+}$PDTA and 0.1 M potassium tetraborate were used as the electrolyte, while on the positive side of the cell 50 mL of a 0.4 M K$_4$Fe(CN)$_6$, 0.6 M K$_3$Fe(CN)$_6$, and 0.025 M potassium tetraborate were used as the electrolyte solution in the fully discharged state. The solutions were contained in 100 mL glass round bottom flasks submerged in an oil bath at 40° C. The CrPDTA solution was purged with argon for one hour before cycling began and was kept under positive argon pressure during the experiment. The argon was bubbled through a solution of distilled water also heated to 40° C. to pre-saturate the argon with H$_2$O and minimize the CrPDTA solution volume loss.

The Fe(CN)$_6$ concentrations were selected so that the kinetics of the iron side was never the limiting factor in discharging the system and the full capabilities of the CrPDTA could be showcased. Even when the iron side was run in large excess where the species concentrations did not change substantially, the charged species would be at minimum 0.45 M whereas the CrPDTA would have a maximum of 0.4 M. Due to the limited solubility of both K$_4$Fe(CN)$_6$ and K$_3$Fe(CN)$_6$, for the 1.0 M CrPDTA runs the iron concentrations were selected so that they were as high as possible while keeping the same Fe$^{3+}$/Fe$^{2+}$ ratio as to not alter the voltage associated with the iron side.

The formulations chosen did not result in any issues related to viscosity, and throughout cycling there were no substantial issues with electrolyte imbalance or volume changes due to electroosmotic drag. Further electrolyte optimization studies are currently underway to further improve the system.

For KBr flow cell experiments, on the negative side of the cell 10 mL of 0.4 M KCrPDTA and 0.2 M potassium tetraborate were used as the electrolyte, while on the positive side of the cell 20 mL of 2.0 M KBr, 0.5 M Br$a$ and 0.1 M potassium tetraborate were used as the electrolyte solution in the fully discharged state. The CrPDTA solution was contained at room temperature in a 100 mL glass round bottom flask at room temperature. The KBr solution was contained in a 60 mL PFA column component vessel capped with a 58 mm transfer closure with two ⅛" OD compression fitting ports (Savillex). The CrPDTA solution was purged with argon for one hour before cycling began and was kept under positive argon pressure during the experiment.

Example 2

Flow Cell Experiments

Open circuit potential (OCP) experiments were conducted by charging the CrPDTA solution at a constant current at 5% state of charge (SOC) intervals from 5-95% SOC and taking a 30 second OCP reading, which was then averaged to find the reported value. Power experiments were conducted by charging the CrPDTA solution at a constant current for a specified time to a desired SOC before running a CV at a 200 mV s$^{-1}$ scan rate and then discharging the solution at a constant current and subsequently holding at a low voltage for 5 minutes to fully discharge the solution before starting the next charge to a specific SOC. Cycling experiments were conducted by charging and discharging at a constant current, with the charging terminating at a specified time to reach the desired SOC, and with the discharge terminating at a voltage cutoff. The voltage cutoff was 0.5 V when the positive electrolyte was Fe(CN)$_6$ and 0.8 V when the positive electrolyte was KBr. Current efficiency was calculated by dividing the final discharge time by the charge time. Overall voltage efficiency was calculated by dividing the voltage at the midpoint of the discharge run by the voltage at the midpoint of the charge run. Overall energy efficiency was calculated by multiplying the overall voltage efficiency by the current efficiency. Discharge voltage efficiency was calculated by dividing the voltage at the midpoint of the discharge run by the open circuit potential of the cell immediately before the discharge cycle. Discharge energy efficiency was calculated by multiplying the discharge voltage efficiency by the current efficiency. A PTFE diaphragm pump used due to incompatibility of [Cr(PDTA)] with stainless steel.

Example 3

Figure 2A:
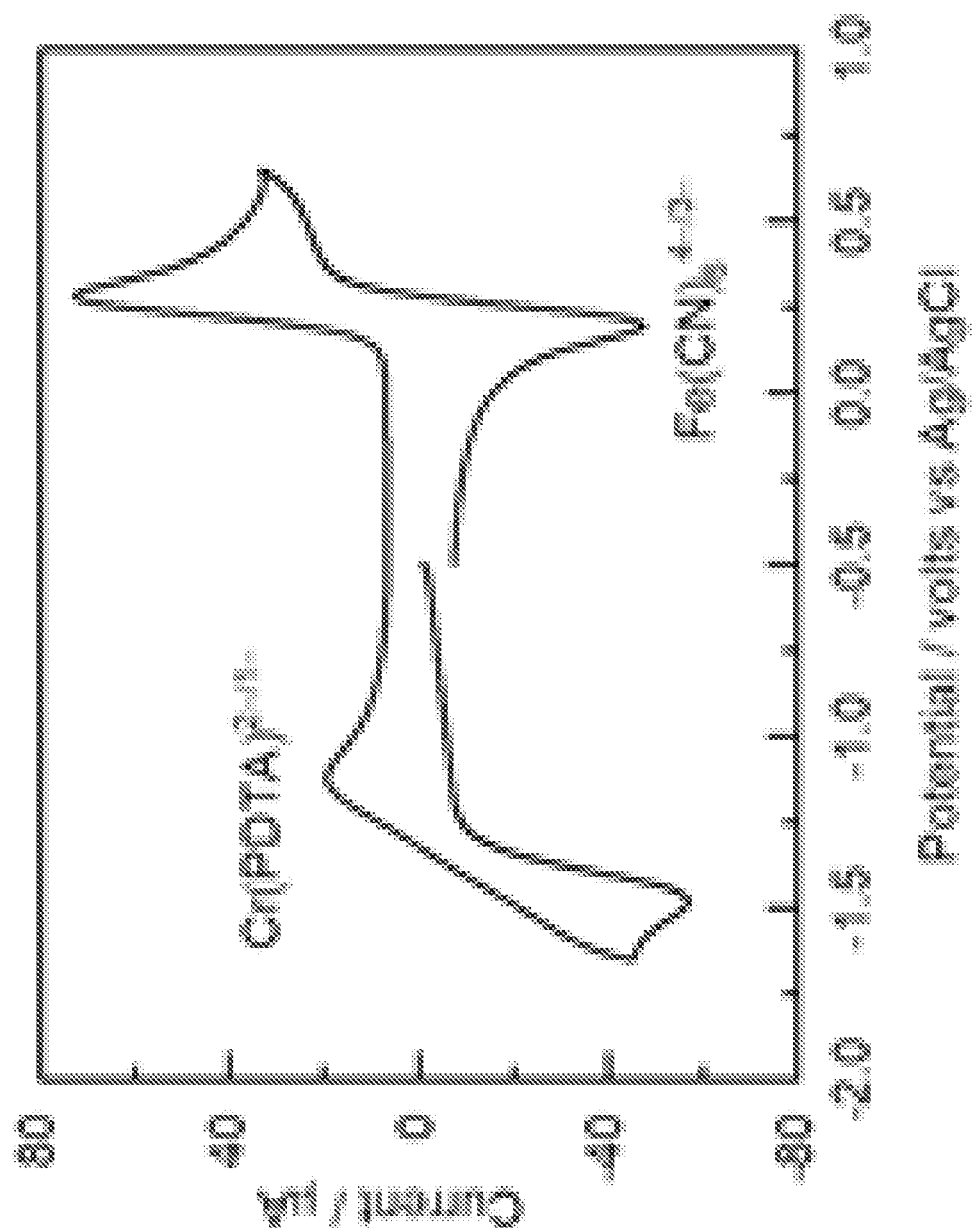
FIG. 2A illustrates a cyclic voltammogram recorded at 100 mV s$^{-1}$ of 5 mM K[Cr(PDTA)] and 5 mM K$_4$[Fe(CN)$_6$] in 0.125 M KB$_i$ (pH 9) recorded on a glassy carbon working electrode.
Figure 5A:
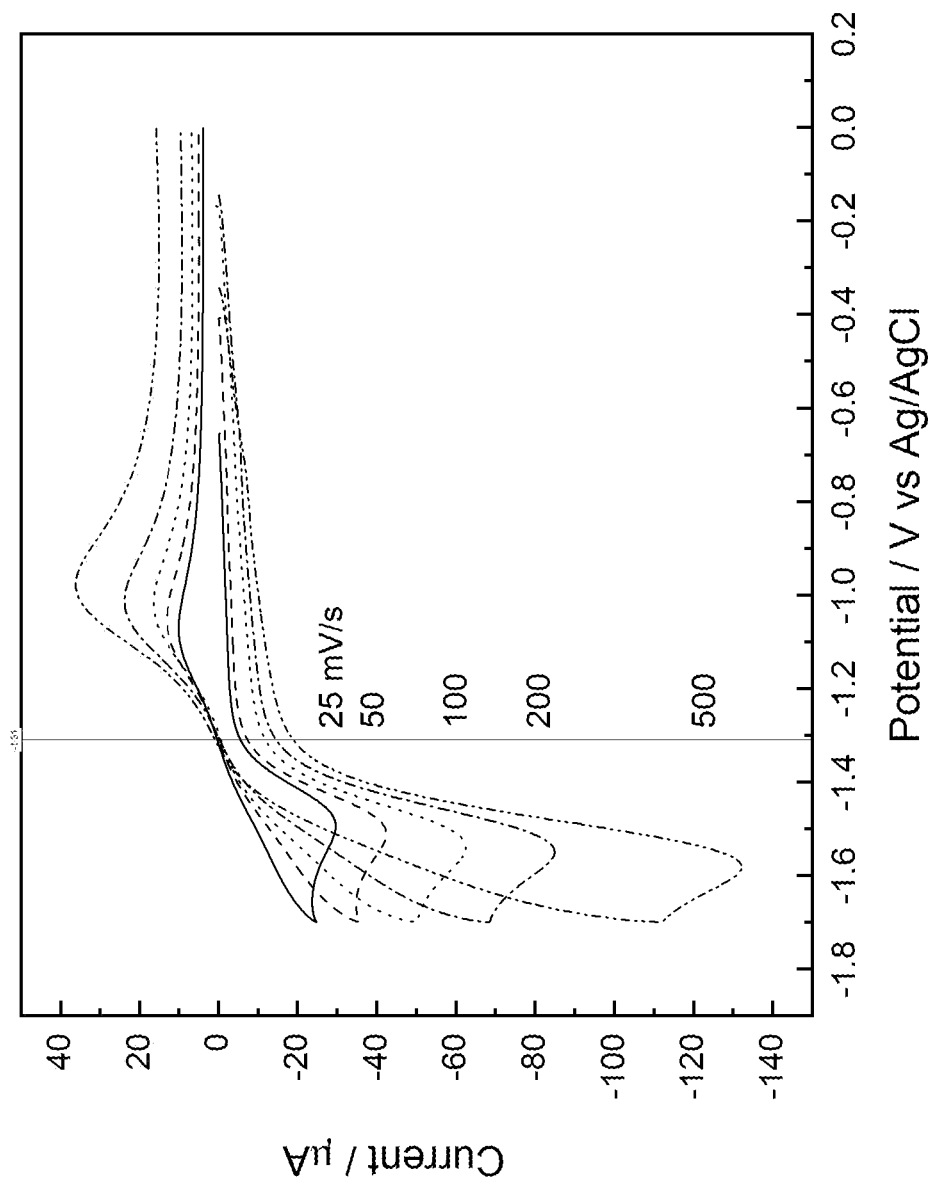
FIG. 5A illustrates the kinetic analysis of CrPDTA reduction illustrating the cyclic voltammetry recorded at different scan rates of a solution containing 5 mM K[Cr(PDTA)] in 0.125 M KB$_i$ at pH 9. The vertical line represents the literature value of E$^0$ (−1.31 V vs Ag/AgCl)
Figure 5B:
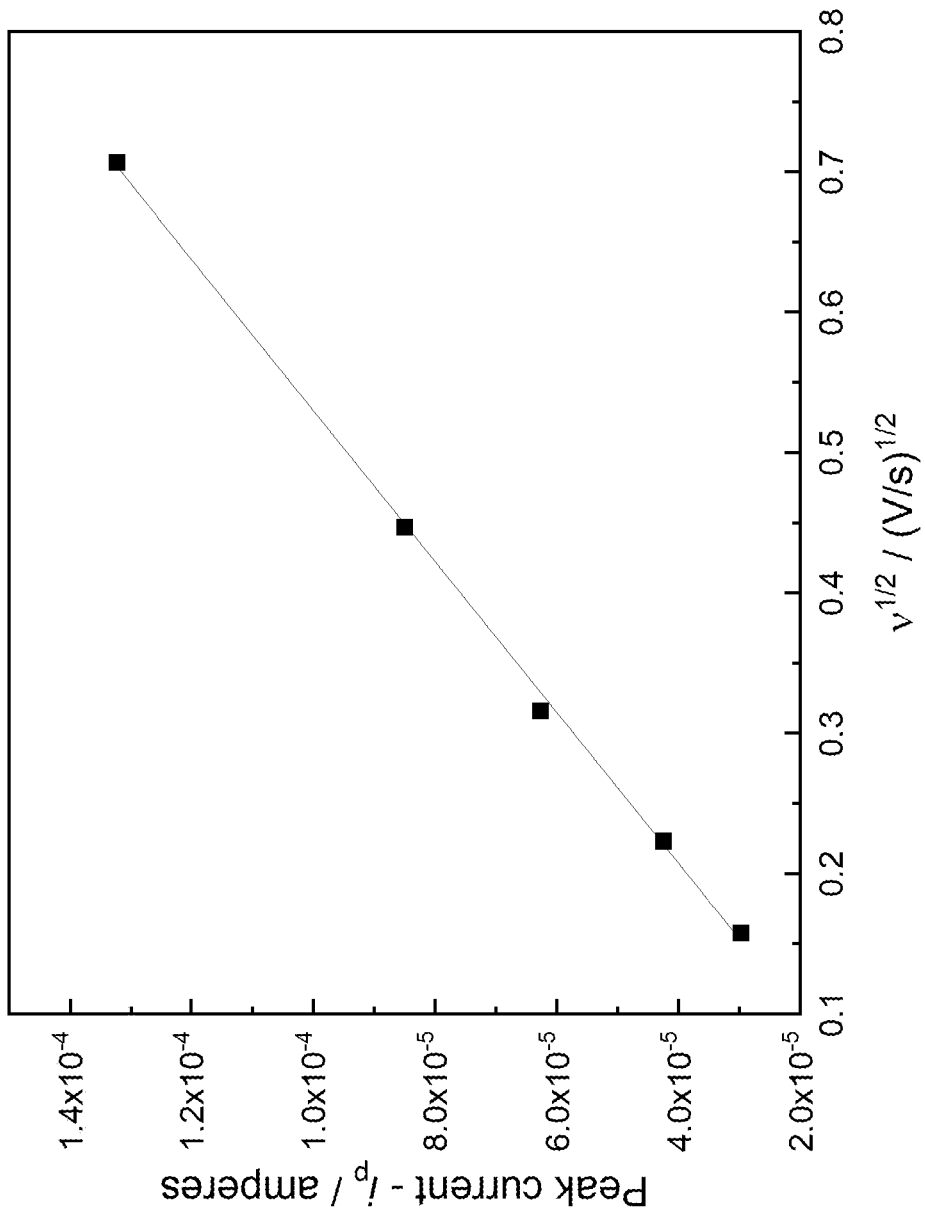
FIG. 5B illustrates the kinetic analysis of CrPDTA reduction illustrating the peak reduction current versus scan rate, v$^{1/2}$ for different scan rates; with a linear fit.
Figure 5C:
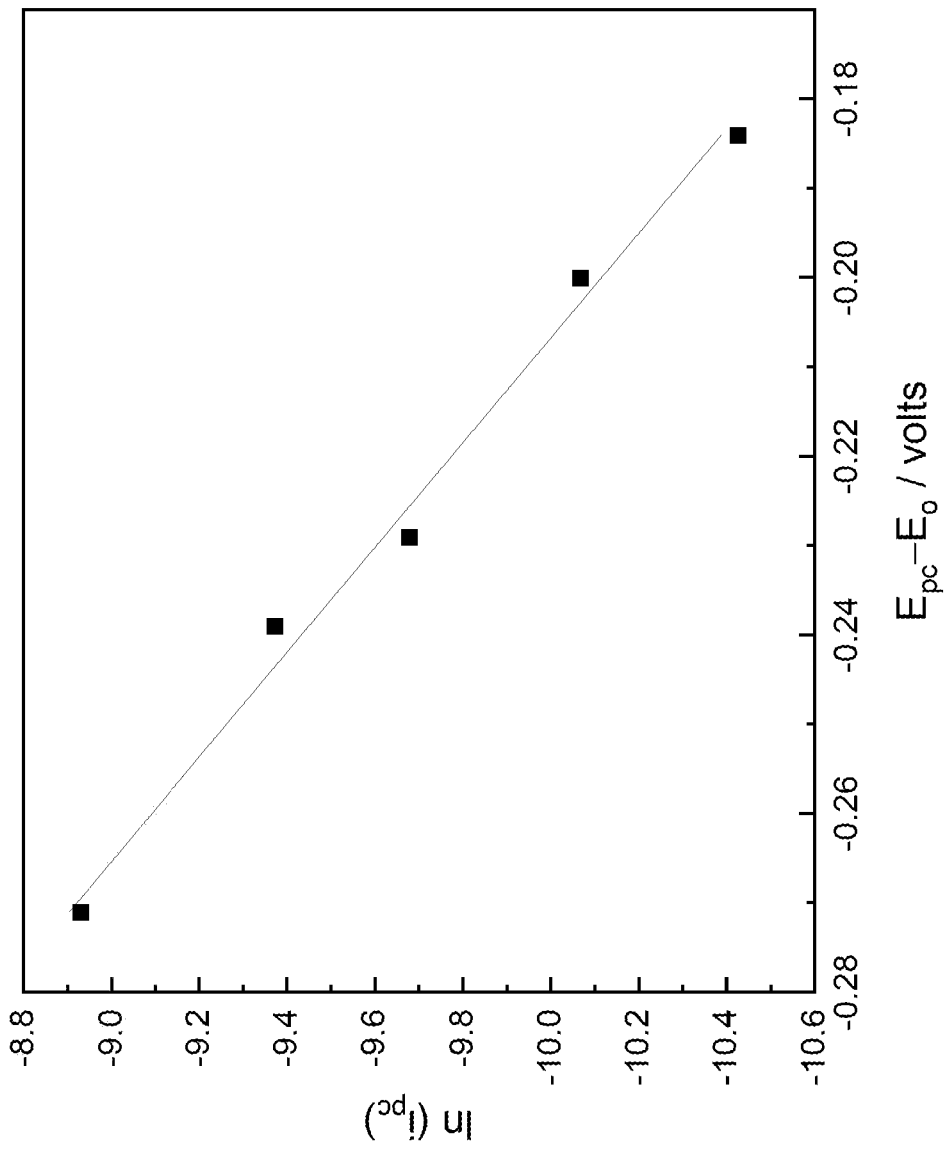
FIG. 5C illustrates the kinetic analysis of CrPDTA reduction illustrating the natural log of the peak reduction current (i$_{pc}$) versus the difference in potential between the voltage at the peak reduction current (E$_{pc}$) and the E$^0$ of the reduction given in literature; with a linear fit.

Cyclic voltammetry (CV) of an aqueous solution containing both CrPDTA and Fe(CN)$_6$ along with a potassium tetraborate (KB) buffer shows redox reactions at -1.31 V and 0.31 vs. Ag/AgCl respectively, demonstrating the compatibility of these complexes with a 1.62 V potential difference (FIG. 2A). Kinetic analysis of the CrPDTA reduction provided a diffusion coefficient D$_O$=6.2×10$^{-6}$ cm$^2$ s$^{-1}$ and a reduction rate constant k$^0$=1.7×10$^{-4}$ cm s$^{-1}$ on glassy carbon (FIGS. 5A-5C), which suggests that CrPDTA diffuses freely in solution and can be reduced faster than V$^{3+/2+}$, but slower than some organics. Table 5 illustrates electrochemical data for the reduction of CrPDTA. All values in Table 5 are approximate.

TABLE 5

| Scan Rate (mV s$^{-1}$) | E$_{pc}$ (V) | E$_{pa}$ (V) | ΔE$_p$ (V) | i$_{pa}$ (µA) | i$_{pc}$ (µA) |
| --- | --- | --- | --- | --- | --- |
| 25 | -1.494 | -1.071 | 0.423 | 10.01 | -29.63 |
| 50 | -1.510 | -1.053 | 0.457 | 13.08 | -42.39 |
| 100 | -1.539 | -1.019 | 0.520 | 16.50 | -62.55 |
| 200 | -1.549 | -1.012 | 0.537 | 23.84 | -84.91 |
| 500 | -1.581 | -0.976 | 0.605 | 36.18 | -132.2 |

Figure 2B:
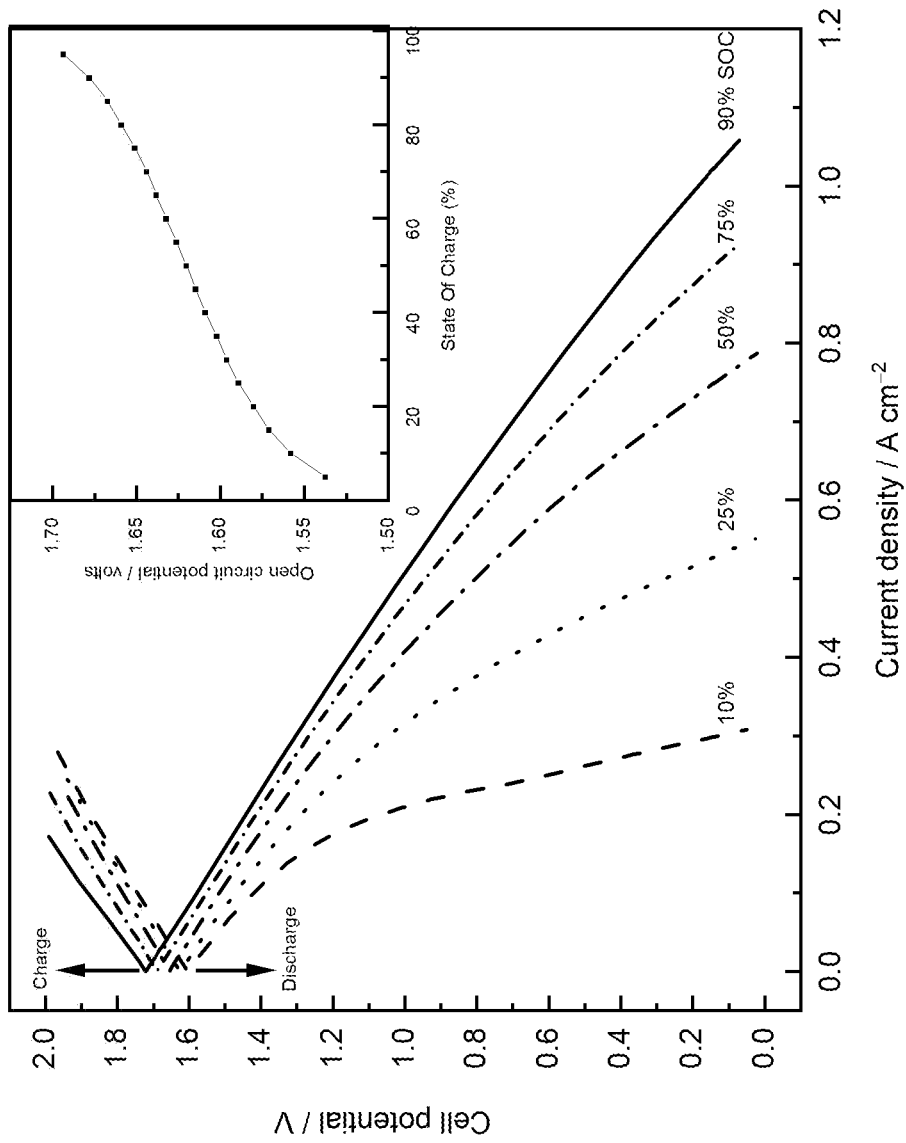
FIG. 2B illustrates polarization curves of iron-chromium chelate cell at varying SOC, and the inset illustrates cell OCP vs. SOC.
Figure 2C:
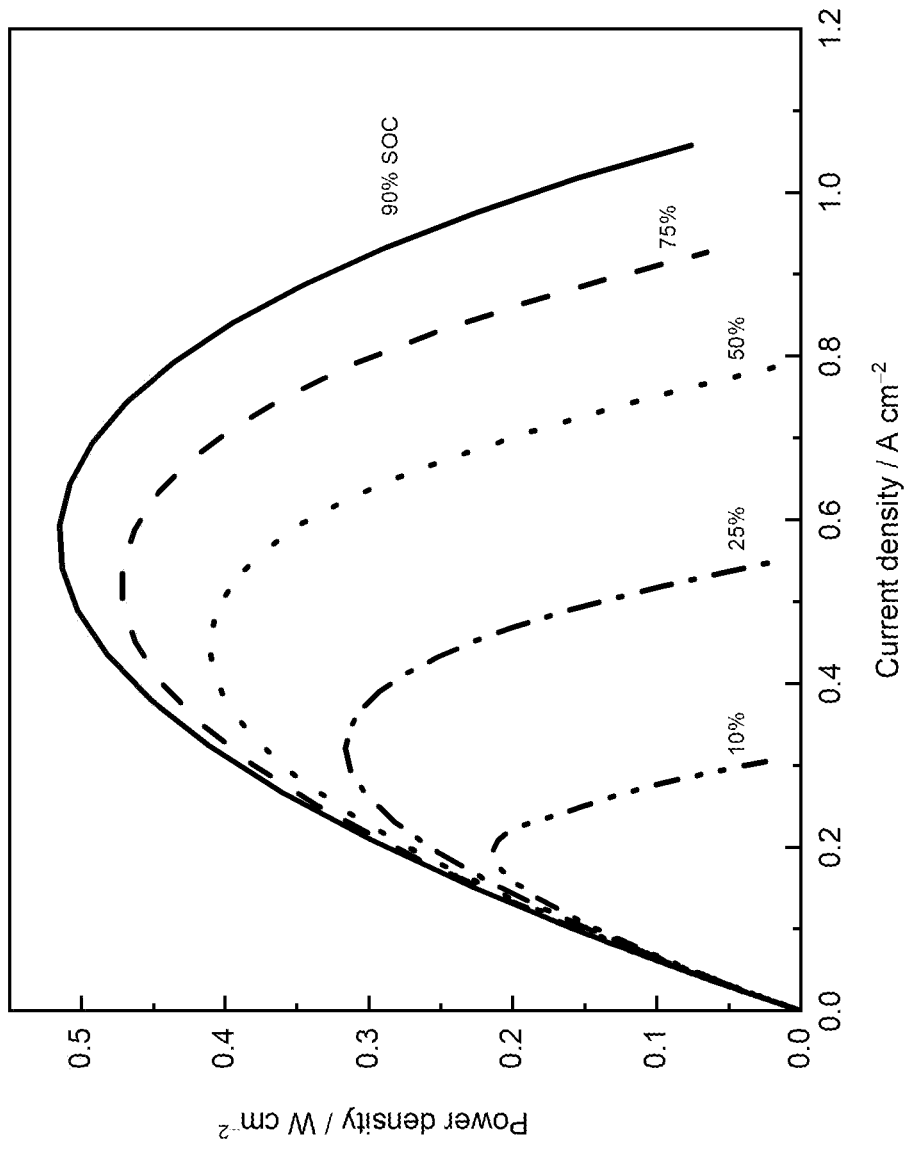
FIG. 2C illustrates the discharge power density versus current density of an iron-chromium chelate cell at varying SOC.

A bulk electrolyte solution of 0.4 M K[Cr(PDTA)] was prepared by heating chrome alum with PDTA in the presence of KOH and buffered at pH 9.5 with 0.2 M KB$_t$. The positive electrolyte was prepared with a volumetric excess of both $K_3[Fe(CN)_6]$ and $K_4[Fe(CN)_6]$ (0.75 M total Fe conc.) and buffered with 25 mM $KB_i$. These solutions were pumped through a flow cell containing carbon paper electrodes separated by a cation exchange membrane. The cell was charged at 50 mA cm$^{-2}$ and the open-circuit potential (OCP) monitored as a function of state of charge (SOC) from 5 to 95% (FIG. 2B, inset). The OCP increased from 1.54 to 1.70 V, with a value of 1.62 V at 50% SOC. The current-voltage behavior of the cell was monitored at various SOC values (FIG. 2B) and shows nearly linear (i.e. ohmic) response between 1.2 and 2.0 V at 50% SOC, suggesting the cell performance is not substantially hindered by CrPDTA redox kinetics, but rather by the membrane resistance (total ohmic resistance=1.7 $\Omega$cm$^2$). The discharge power density shown in FIG. 2C shows peak power densities ranging from 0.2 to 0.5 W cm$^{-2}$ between 10% and 90% SOC, with a peak power of 0.515 W cm$^{-2}$.

Figure 3A:
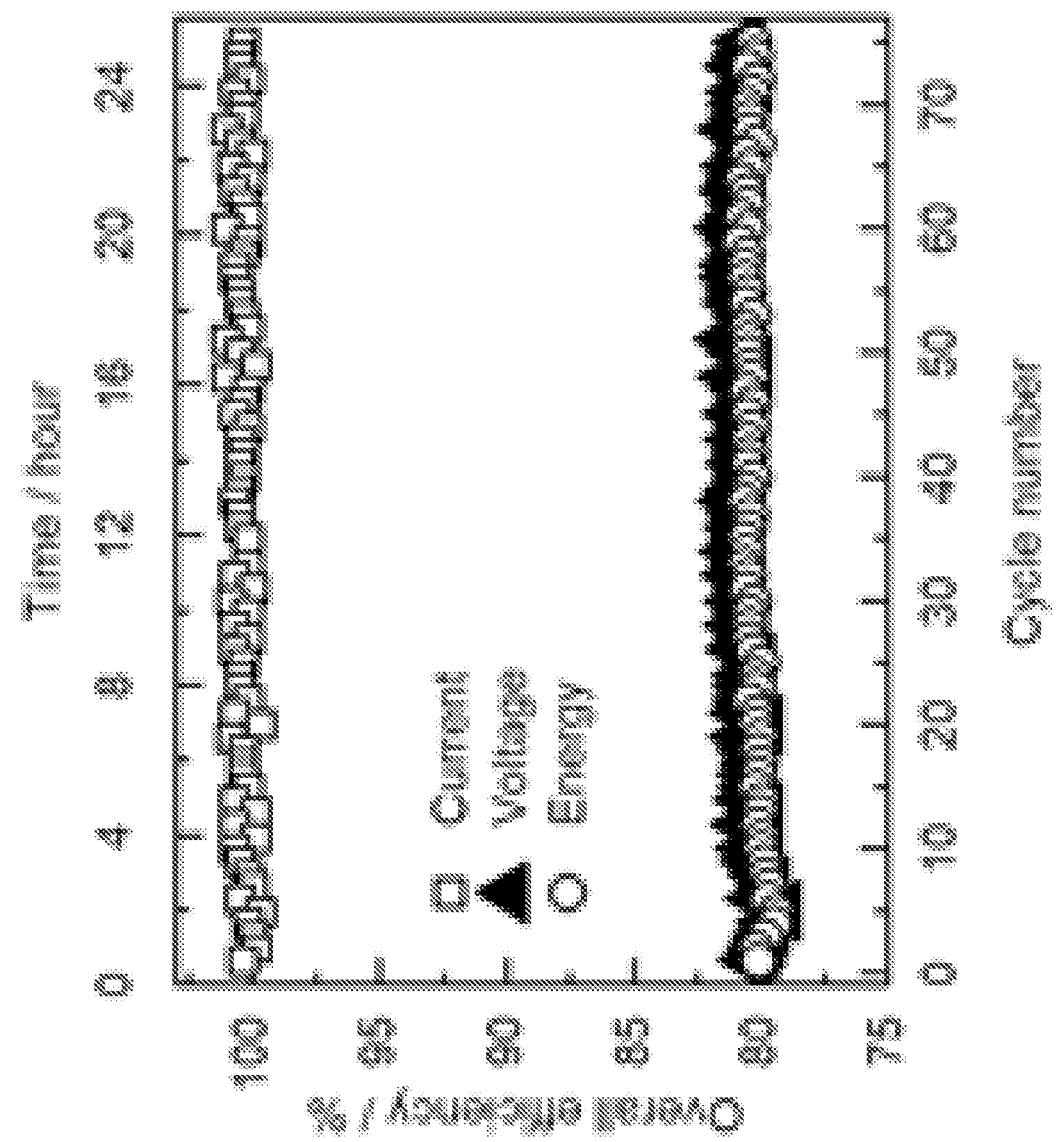
FIG. 3A illustrates iron-chromium chelate cell cycling illustrating the current, voltage and energy efficiency per cycle at ±0.1 A cm$^{-2}$ to 80% SOC using 0.4 M CrPDTA electrolyte.
Figure 6A:
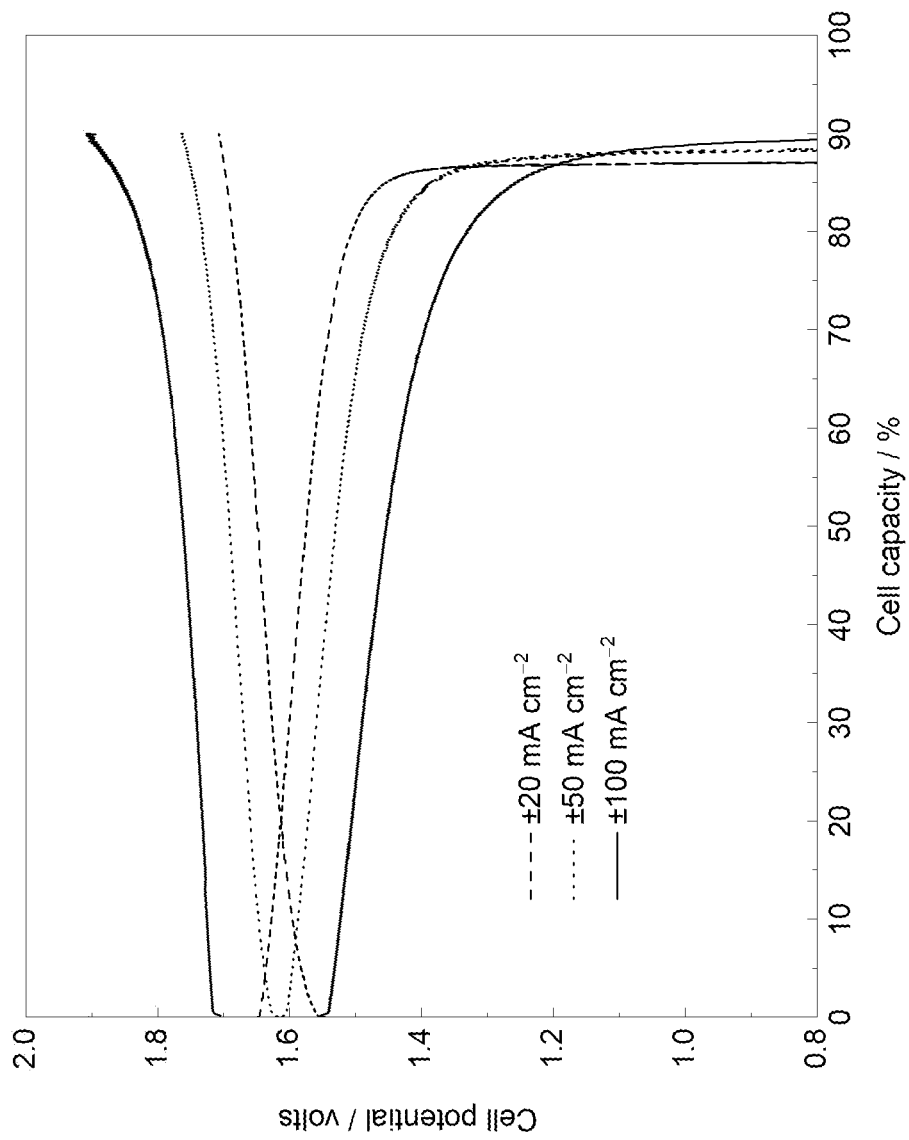
FIG. 6A illustrates iron-chromium cell cycling efficiency illustrating the cell potential upon constant charge/discharge at three current densities to 90% SOC; the horizontal line at 1.62 V represents the OCP at 50% SOC.
Figure 6B:
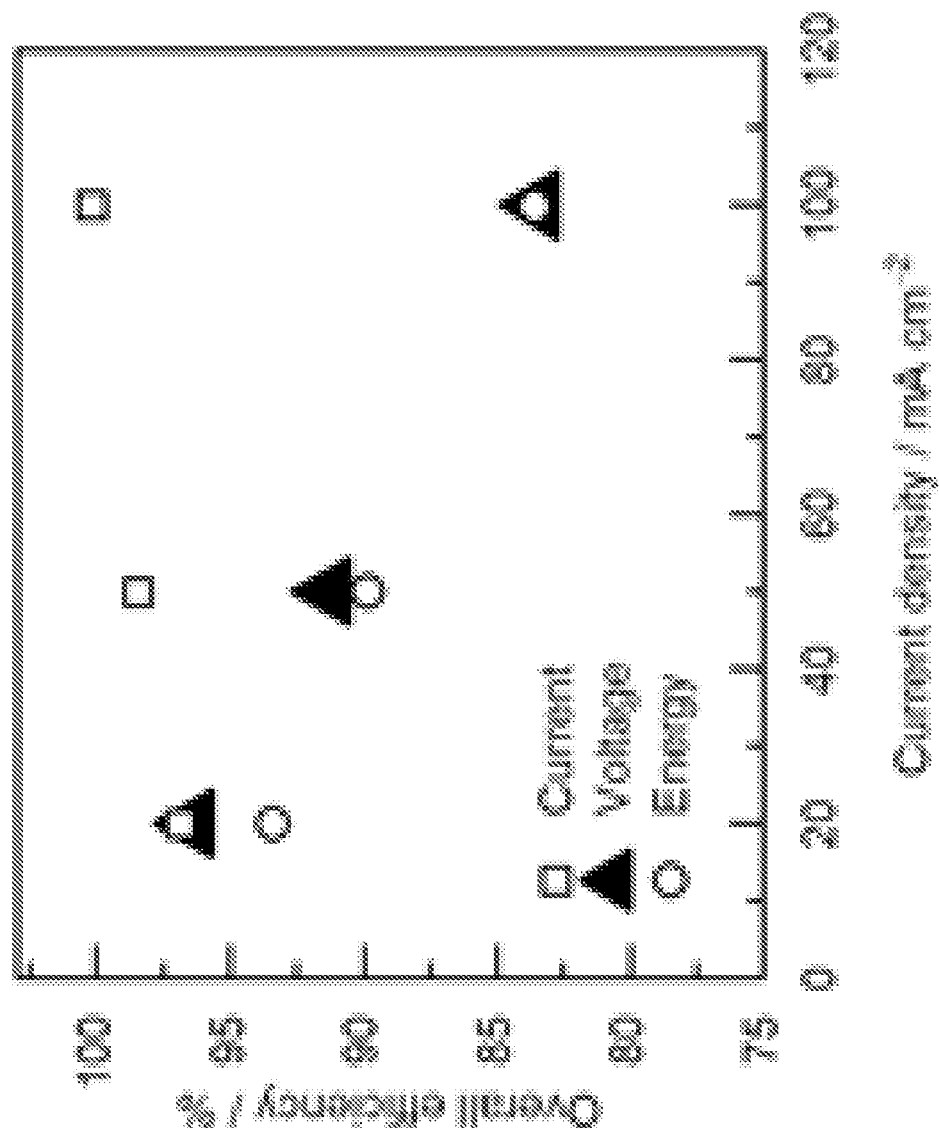
FIG. 6B illustrates iron-chromium cell cycling efficiency illustrating the current, voltage, and energy efficiencies for the cell charge/discharge cycles in FIG. 6A.
Figure 6C:
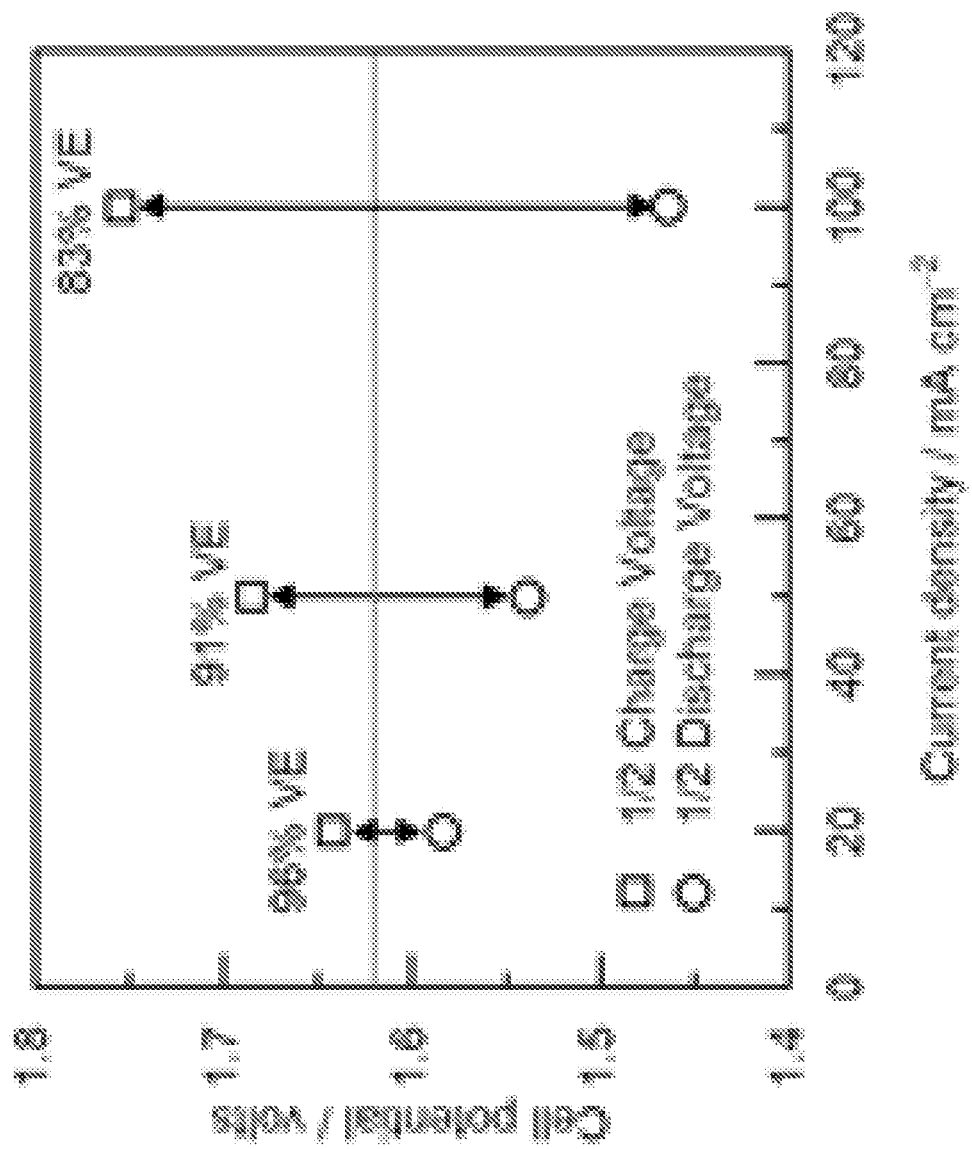
FIG. 6C illustrates iron-chromium cell cycling efficiency illustrating the cell potential at ½ total charge time and ½ total discharge time during constant charge/discharge cycles.

The cell was cycled 75 times at room temperature over 26 h at a constant current of ±0.1 A cm$^{-2}$ using 80% of the total electrolyte capacity as a coulombic charging limit per cycle (FIG. 3A). Under these conditions, the current efficiency per cycle was quantitative (100.0±0.3%) indicating no significant side reactions occurred, the round-trip energy efficiency was 80.0±0.4%, and the discharge capacity was unchanged from the first to the last cycle. Cycling at 50 and 20 mA cm$^{-2}$ reduced the overpotential, raising the round trip energy efficiencies to 90 and 93% respectively as illustrated in FIGS. 6A-6C. Table 7 illustrates the cycling data for Cr(PDTA)-Fe(CN)$_6$ flow battery. All values in Table 7 are approximate.

TABLE 7

| Cycle Rate/mA cm$^{-2}$ | 20 | 50 | 100 |
| --- | --- | --- | --- |
| Charge Time/s | 3475 | 1390 | 695 |
| Discharge Time/s | 3365 | 1368 | 695 |
| Total Charge/C | 347.5 | 347.5 | 347.5 |
| Total Discharge/C | 336.5 | 342 | 347.5 |
| Charge potential at 45% SOC/V | 1.642 | 1.685 | 1.754 |
| Discharge potential at 45% SOC/V | 1.583 | 1.538 | 1.464 |
| Current Efficiency/% | 96.8 | 98.4 | 100.0 |
| Voltage Efficiency/% | 96.4 | 91.3 | 83.5 |
| Energy Efficiency/% | 93.4 | 89.8 | 83.5 |

Figure 3B:
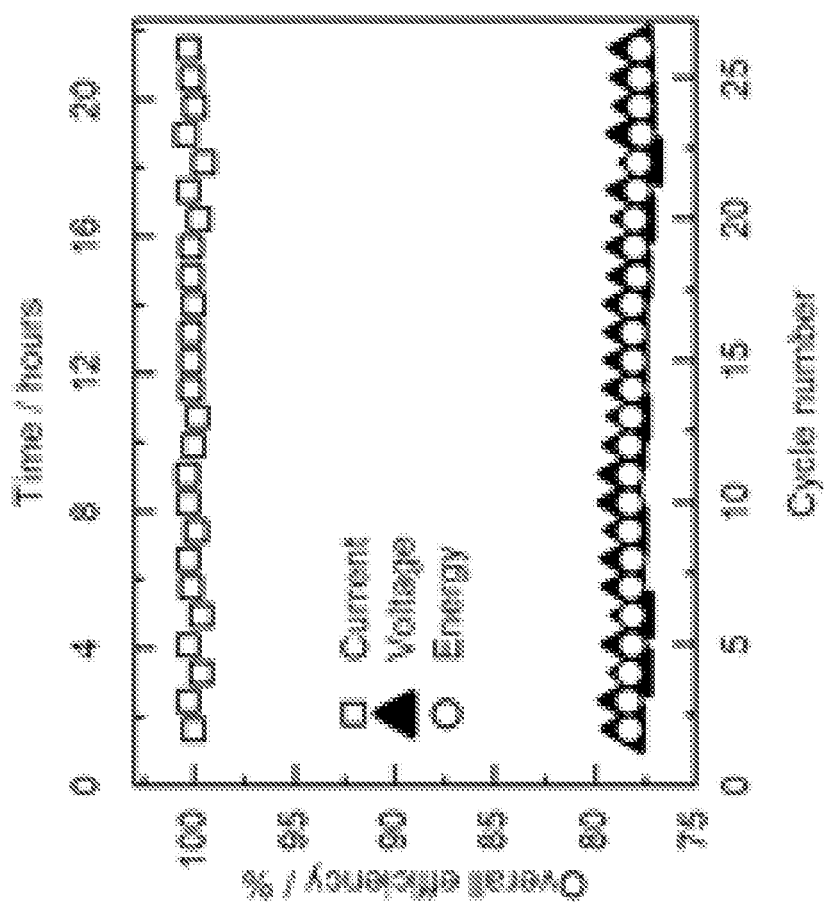
FIG. 3B illustrates cell efficiencies for iron-chromium chelate cell per cycle for 25 cycles at ±0.1 A cm$^{-2}$ to 80% SOC using 1.0 M CrPDTA electrolyte.
Figure 3C:
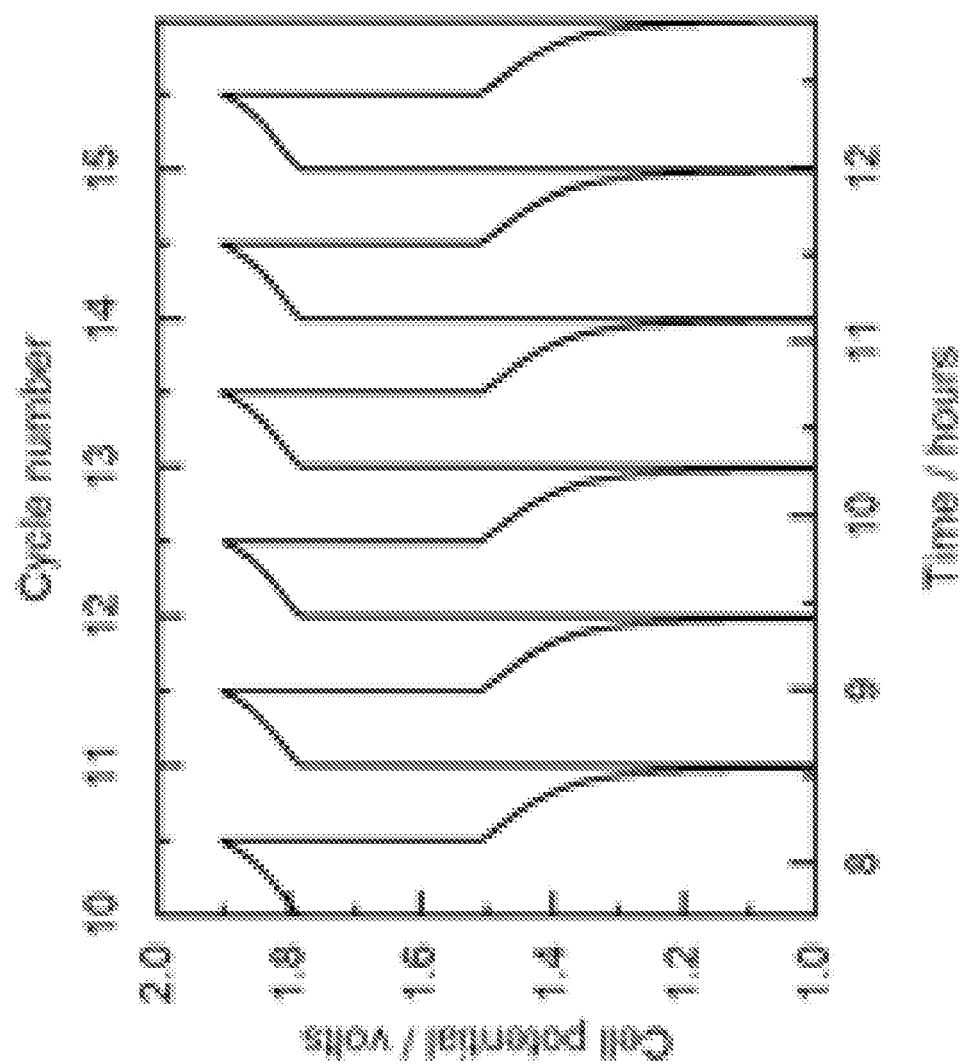
FIG. 3C illustrates the cell voltage for iron-chromium chelate cell during cycling from FIG. 3B.

The concentration of the Cr(PDTA) electrolyte was increased to 1.0 M and cycled the cell 25 times at 40° C. (FIGS. 3B and 3C). Again, quantitative current efficiency (100±0.2%) was observed, although the energy efficiency was 78.1±0.2%. The maximum solubility of K[Cr(PDTA)] at room temperature was observed to be 1.32 M; therefore, significant opportunities are available for improving the CrPDTA electrolyte to optimize concentration, viscosity, and performance, as has been shown for the Fe(CN)$_6$ electrolyte.

Figure 7A:
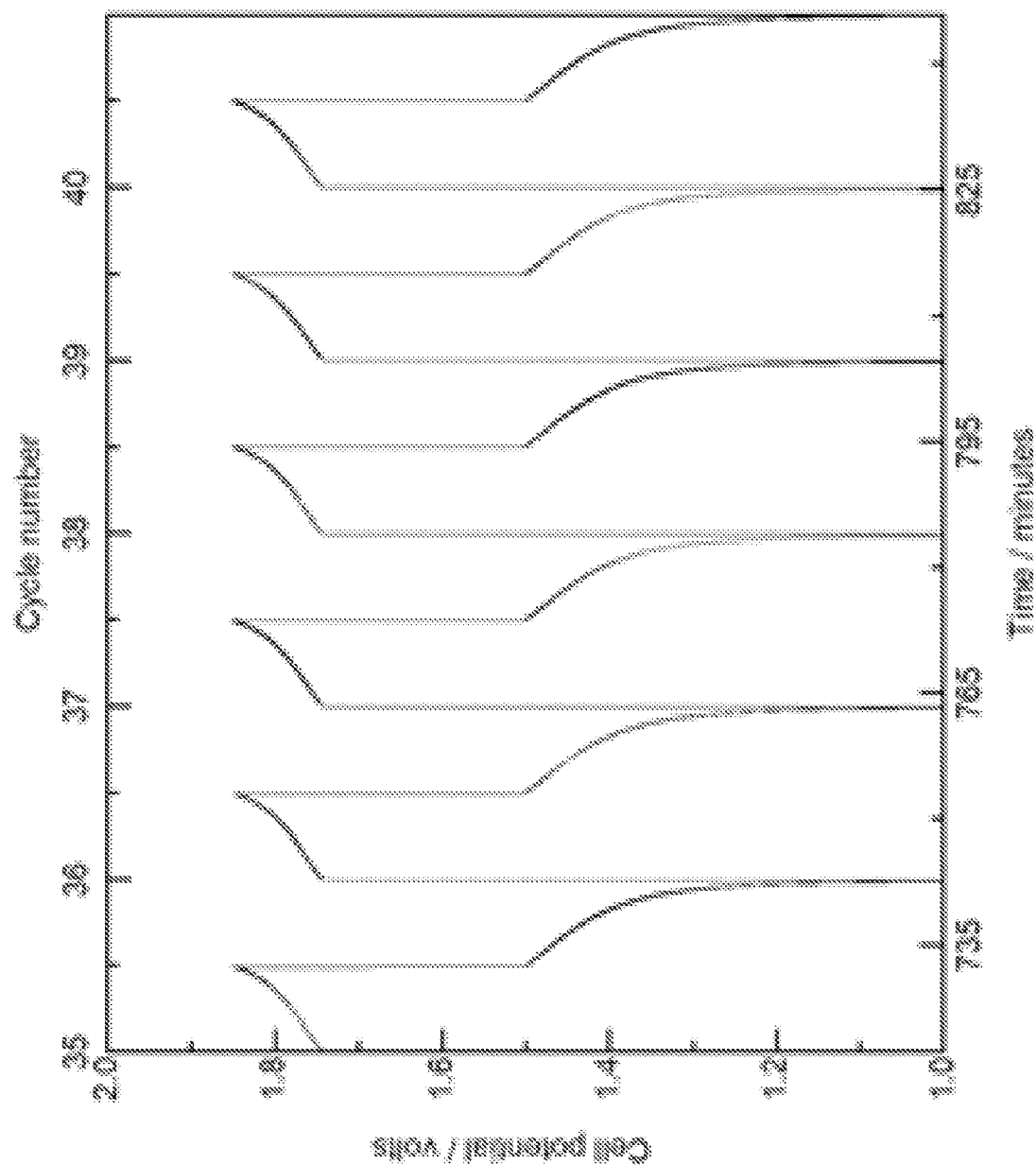
FIG. 7A illustrates iron-chromium cell cycling plots illustrating the cell potential upon constant current charge/discharge at 0.1 A cm$^{-2}$ to 80% SOC.
Figure 7B:
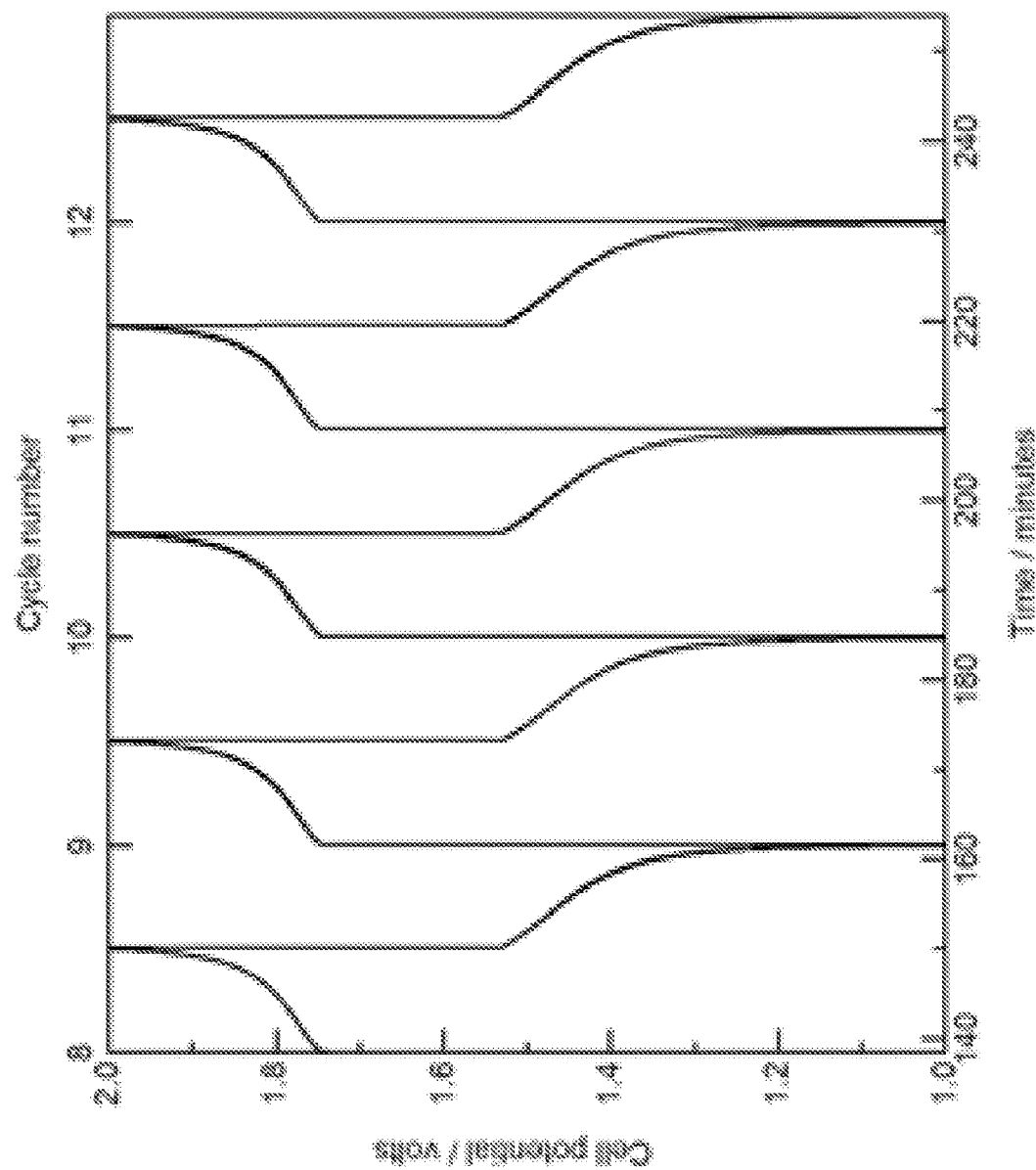
FIG. 7B illustrates iron-chromium cell cycling plots illustrating the cell potential upon constant current charge/discharge at 0.1 A cm$^{-2}$ to 90% SOC.
Figure 8A:
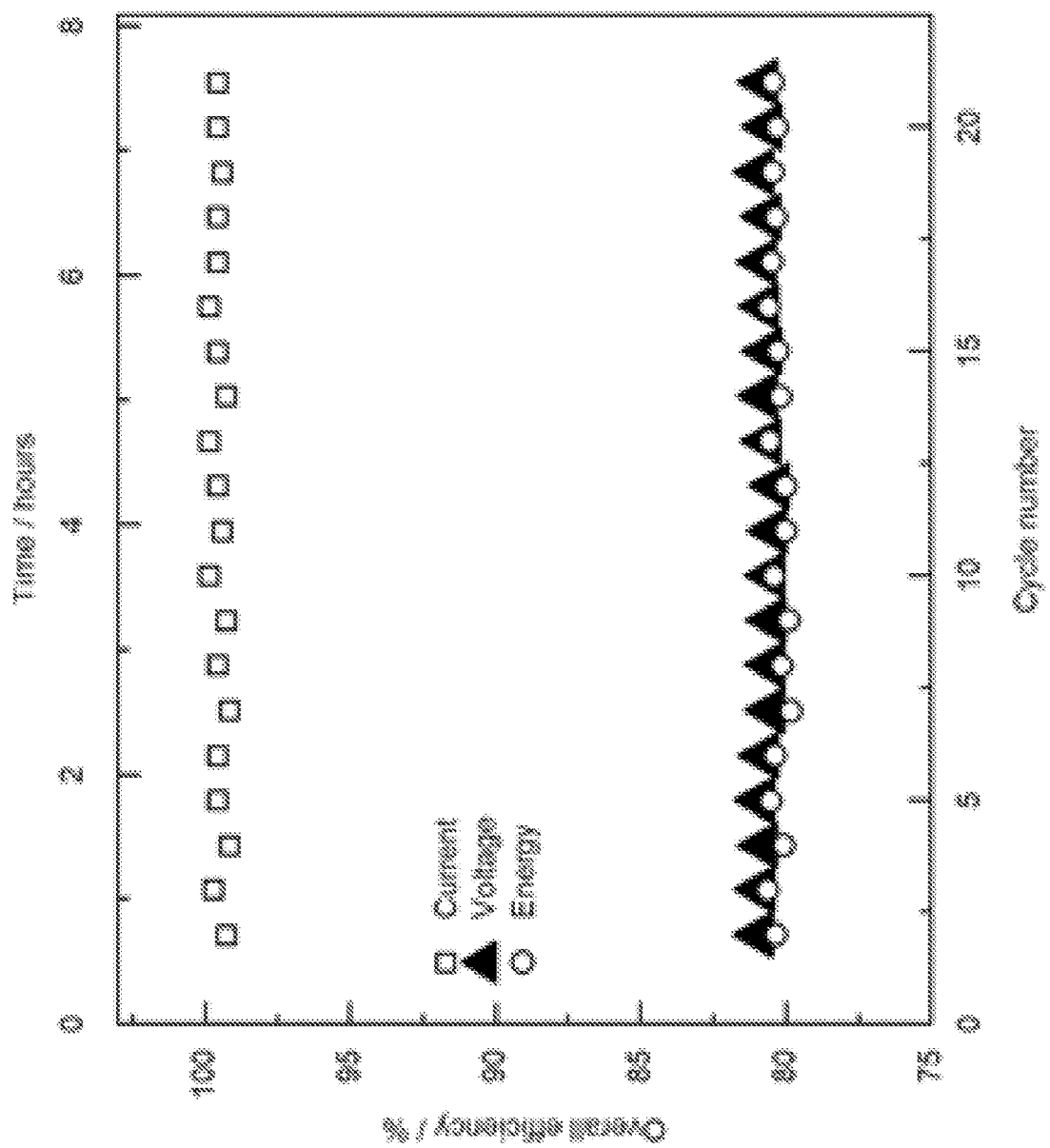
FIG. 8A illustrates iron-chromium and chromium-bromine cell cycling efficiency illustrating a FeCr cell efficiencies upon charge/discharge at 0.1 A cm$^{-2}$ to 90% SOC.

During battery testing, increasing the maximum SOC from 80% to 90% resulted in a decrease in current efficiency to 99.5% (as illustrated in FIGS. 7A-B and FIG. 8A), which may be attributed to H$_2$ evolution. The stability of a fully charged 0.4 M CrPDTA solution was evaluated by analyzing the headspace via gas chromatography. Although H$_2$ was observed after standing for one week, it amounted to an equivalent capacity loss of 2.7%, or 0.4% per day. Consistent with this observation, the electrolyte pH of CrPDTA increased from 9.5 to 10.0 during the cycling experiment in FIG. 3A. This would equate to a current efficiency loss of 0.1% per cycle if attributed exclusively to H$_2$ evolution. The pH increase could also be caused by cross-over of $KB_i$ or exposure of reduced CrPDTA to O$_2$ before or after cycling to form OH$^-$.

Decomposition of CrPDTA was not observed during testing, and the final discharge capacity was unchanged in each cycling experiment. Although very slow decomposition cannot be ruled out without long-term durability studies, the related chelating agent EDTA is considered a persistent organic chemical that decomposes primarily through exposure to UV radiation. Any decomposition of PDTA would be accompanied by the precipitation of Cr$^{3+}$ ions as Cr$_2$O$_3$ at pH 9, which was not observed, but any potential degradation could be mitigated by the addition of excess PDTA to the electrolyte solution.

Example 4

CrBr RFB

Figure 4A:
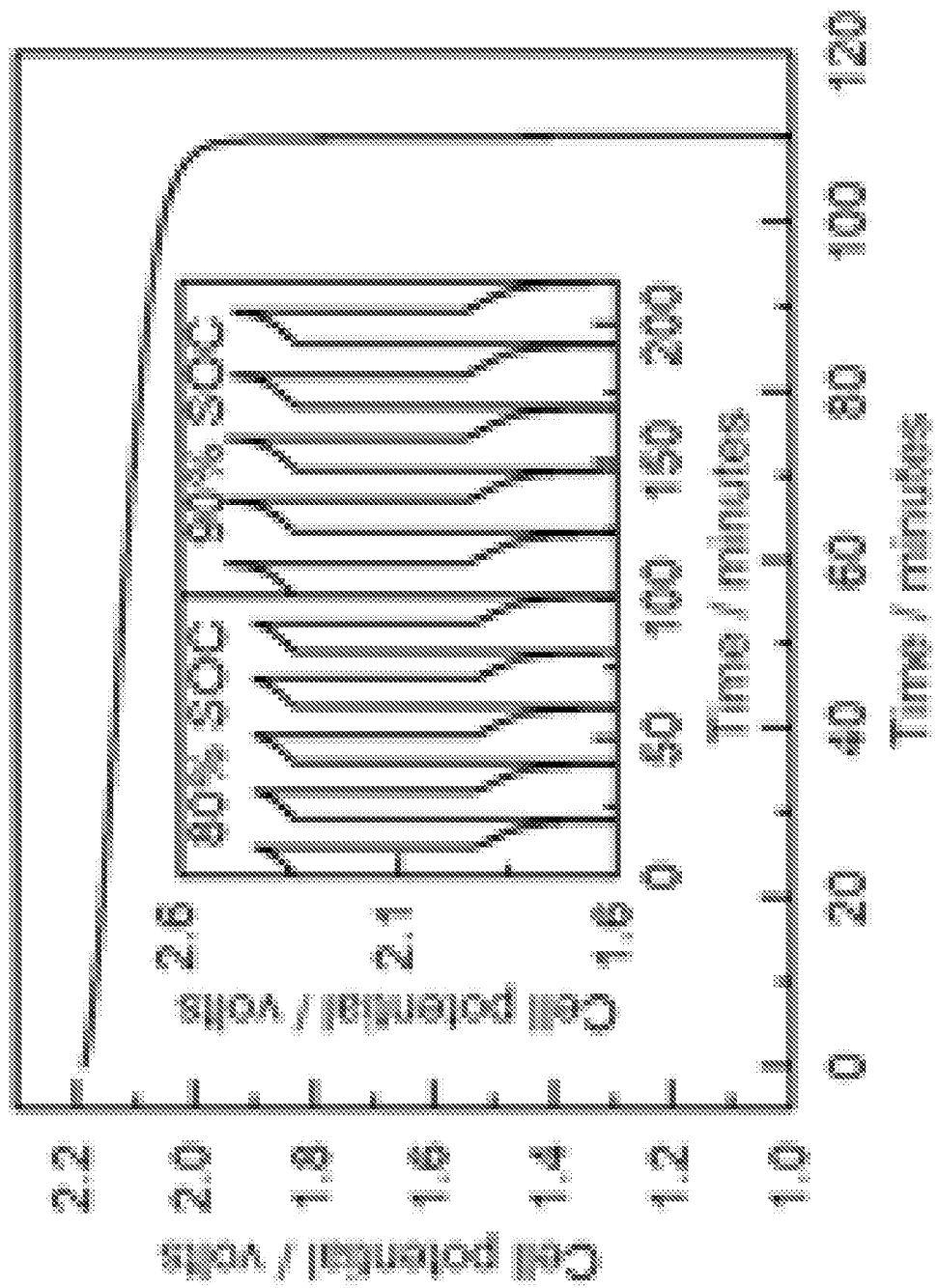
FIG. 4A illustrates chromium-bromine cell cycling data illustrating the cell potential during 10 mA cm$^{-2}$ discharge from 90% SOC, the insert includes the cell potential during cycles at ±0.1 A cm$^{-2}$ to 80% and 90% SOC.
Figure 4B:
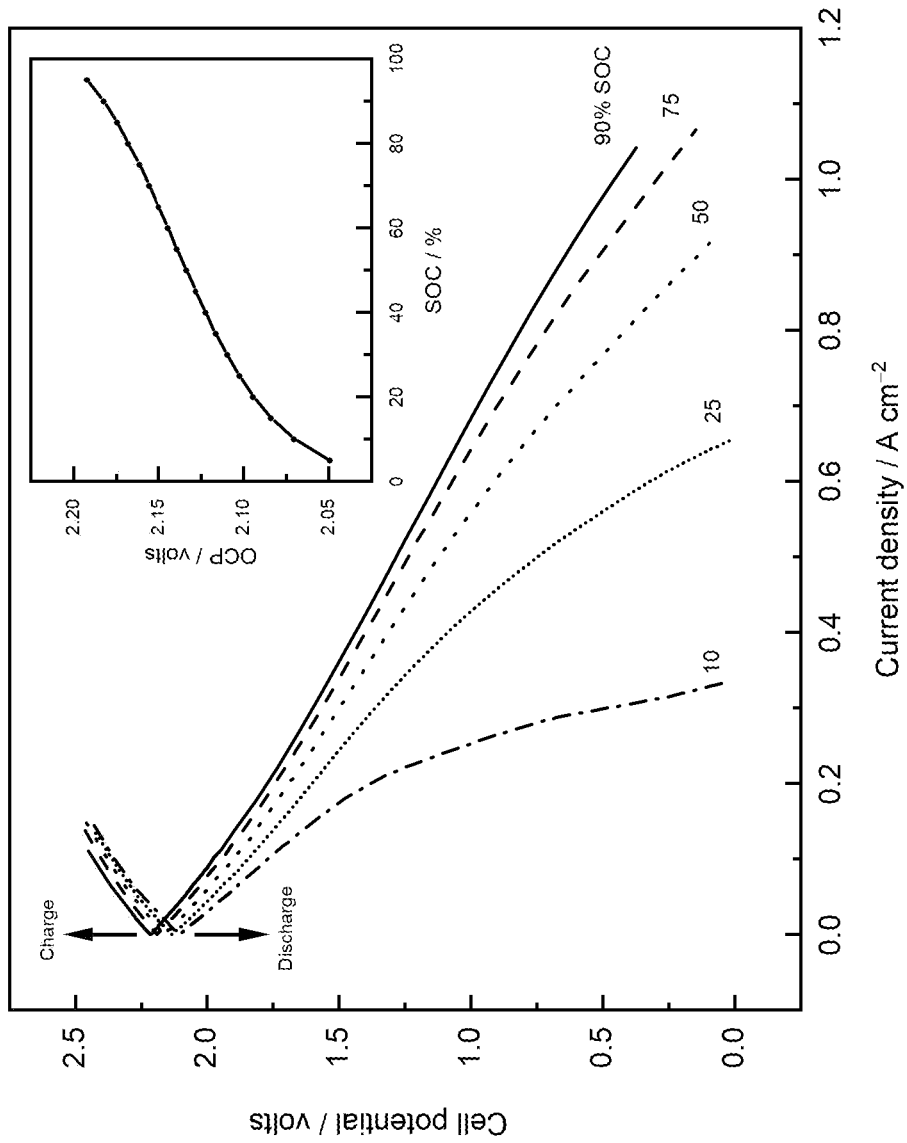
FIG. 4B illustrates chromium-bromine cell polarization curves at varying SOC, with the insert illustrating the cell OCP versus SOC.
Figure 4C:
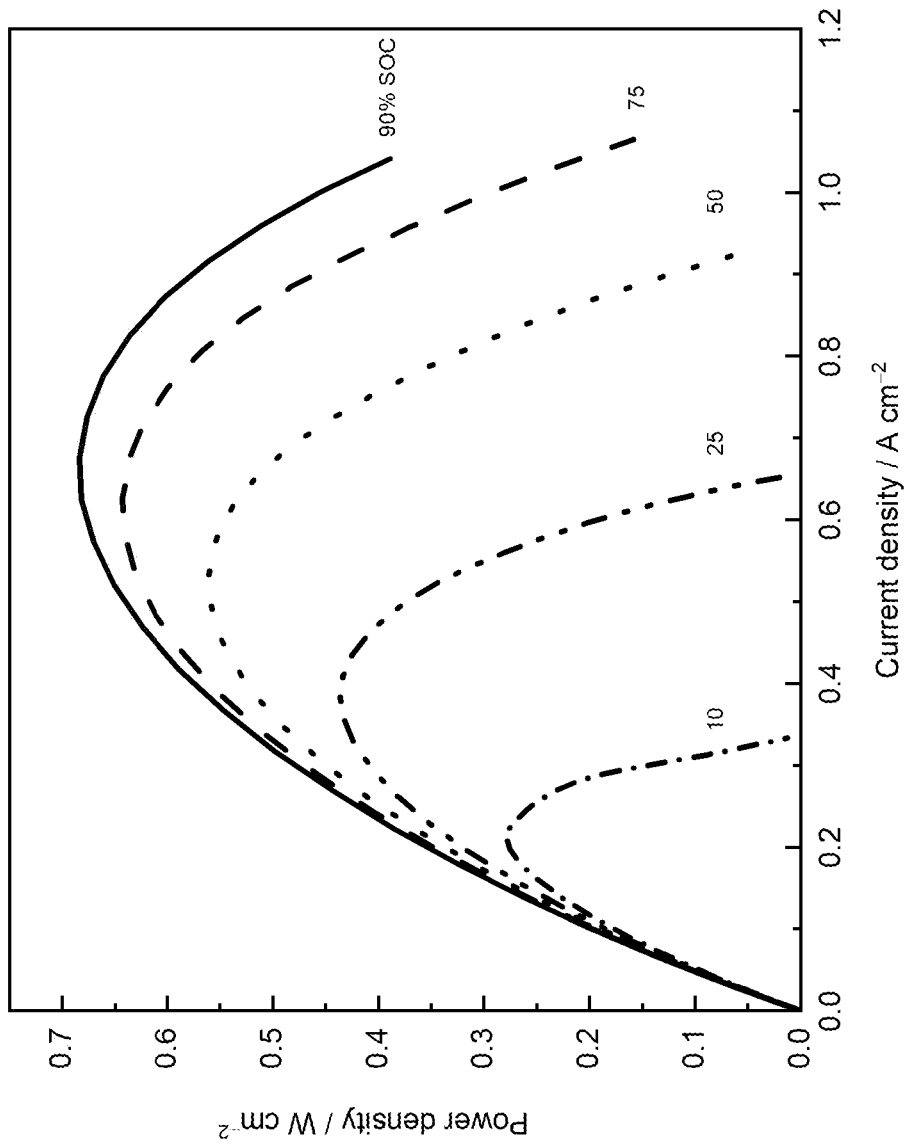
FIG. 4C illustrates chromium-bromine cell discharge power density versus current density at varying SOC.
Figure 8B:
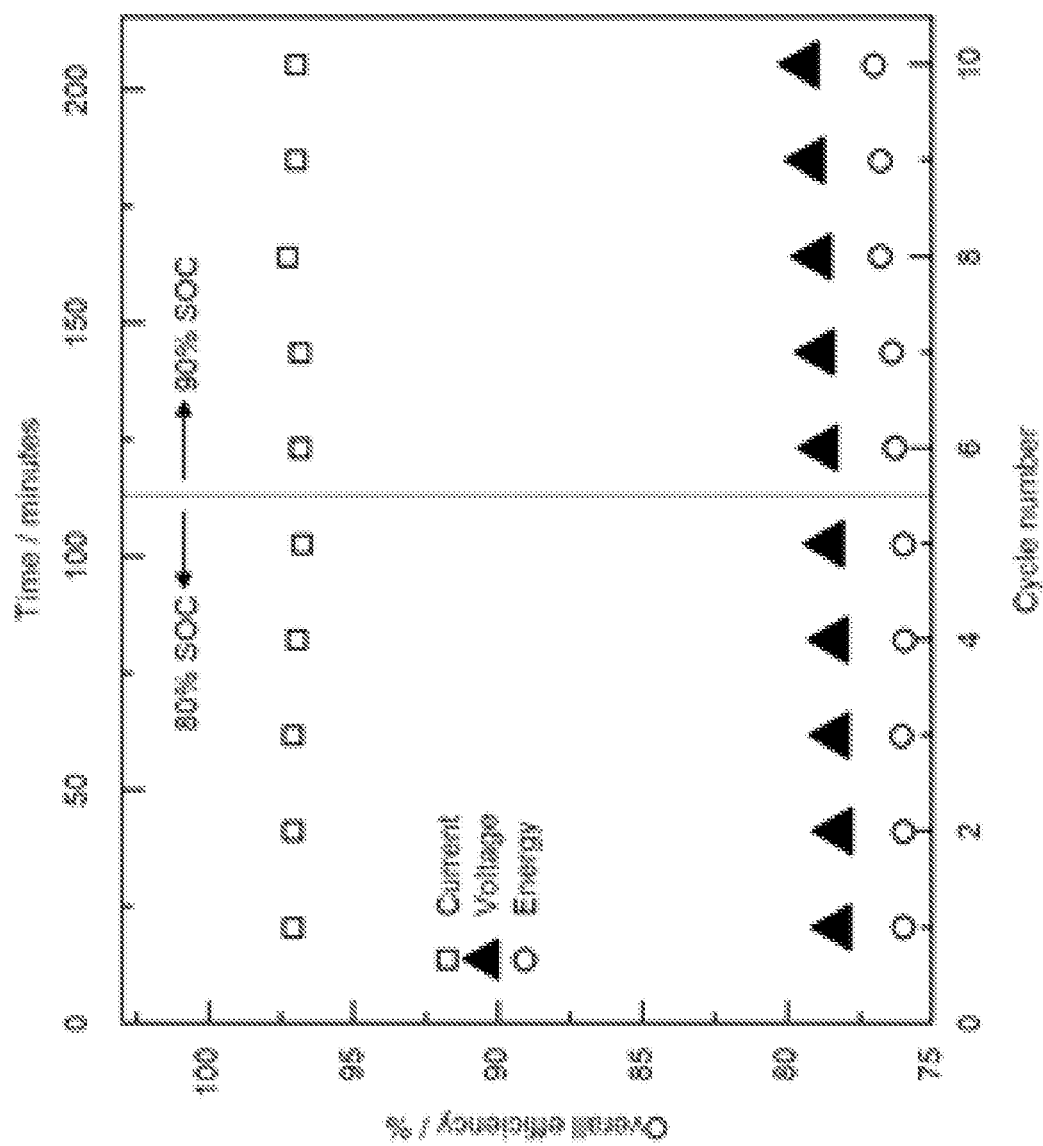
FIG. 8B illustrates iron-chromium and chromium-bromine cell cycling efficiency illustrating a CrBr cell efficiencies upon charge/discharge at 0.1 A cm$^{-2}$ to 80% SOC (cycles 1-5) and 90% SOC (cycles 6-10)
Figure 9A:
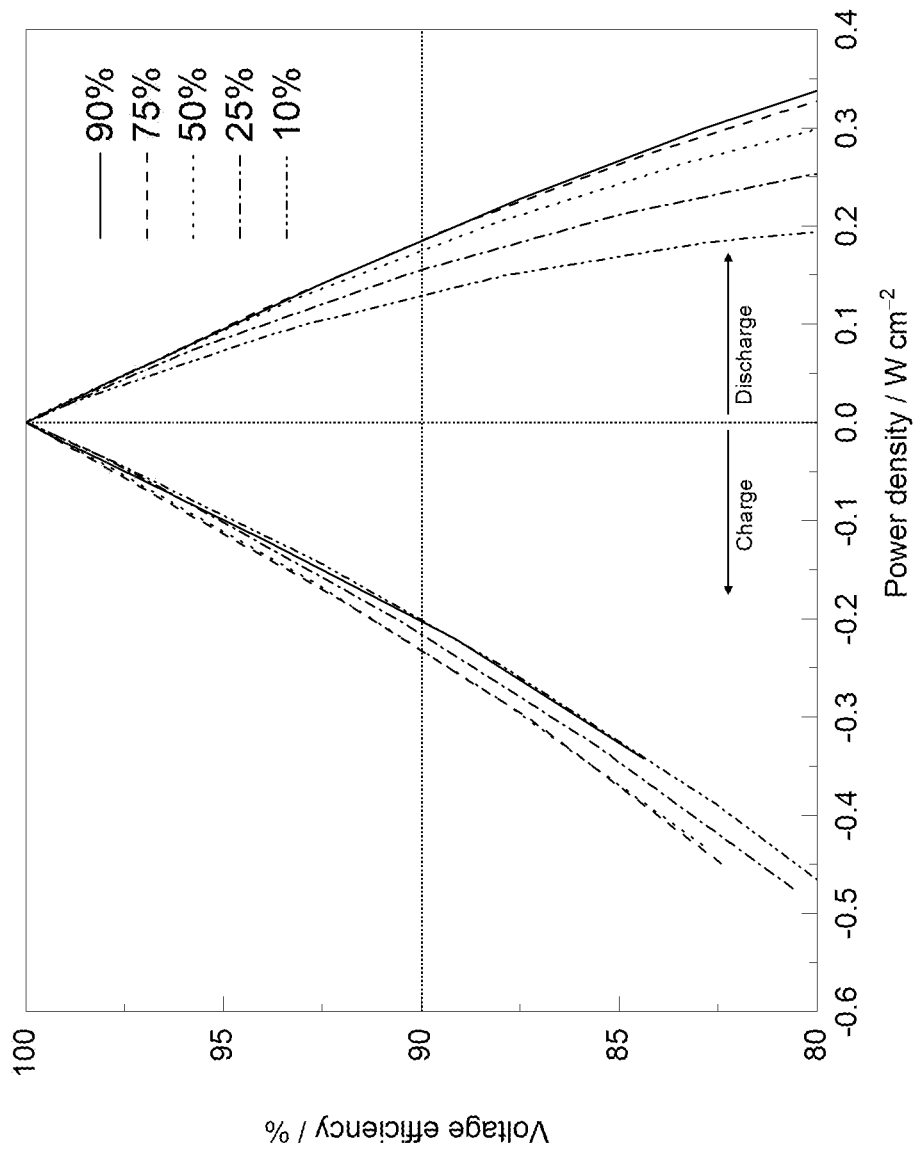
FIG. 9A illustrates iron-chromium cell polarization data with fitting of pump pulses illustrating the voltage efficiency versus power density at 5 different SOC.
Figure 9B:
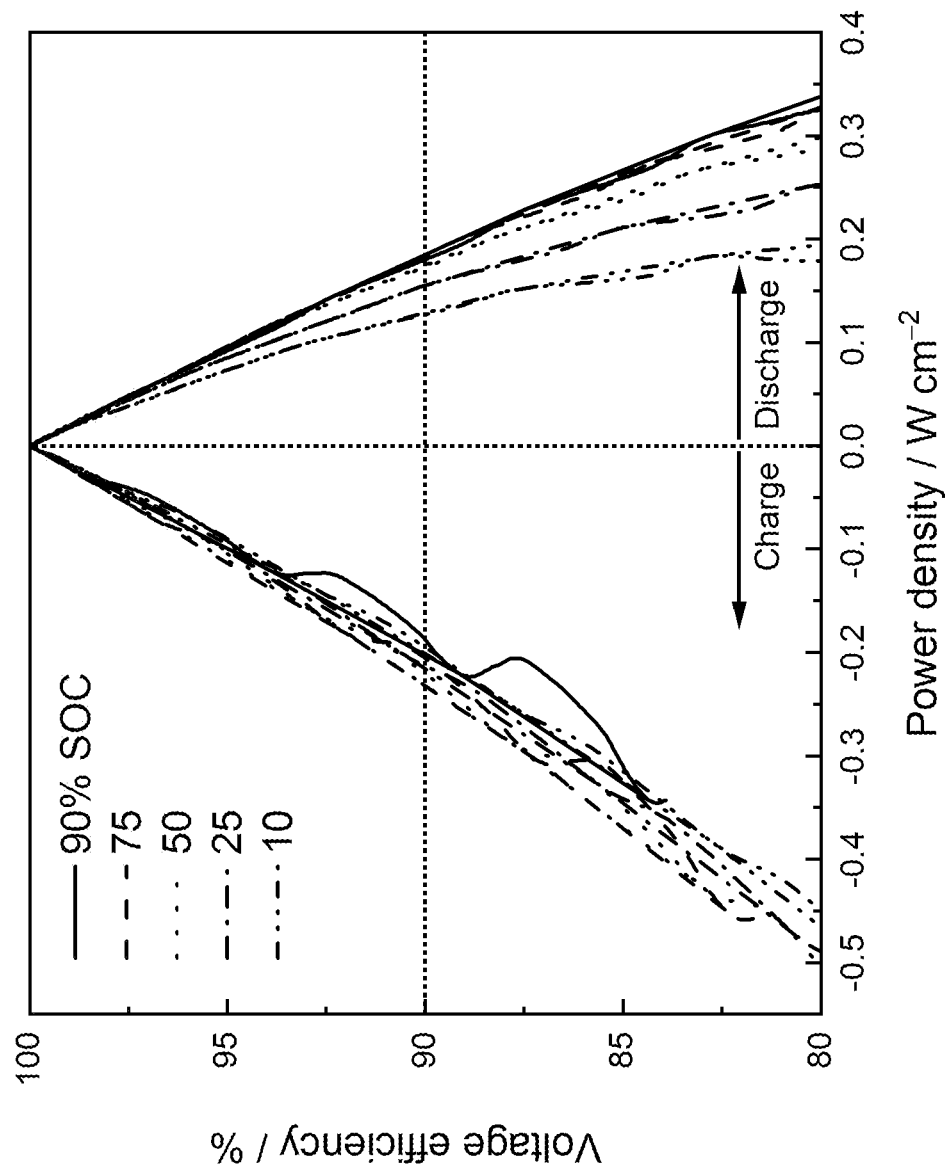
FIG. 9B illustrates iron-chromium cell polarization data with fitting of pump pulses illustrating the voltage efficiency versus power density at 5 different SOC plotted with original pump pulse data.
Figure 9C:
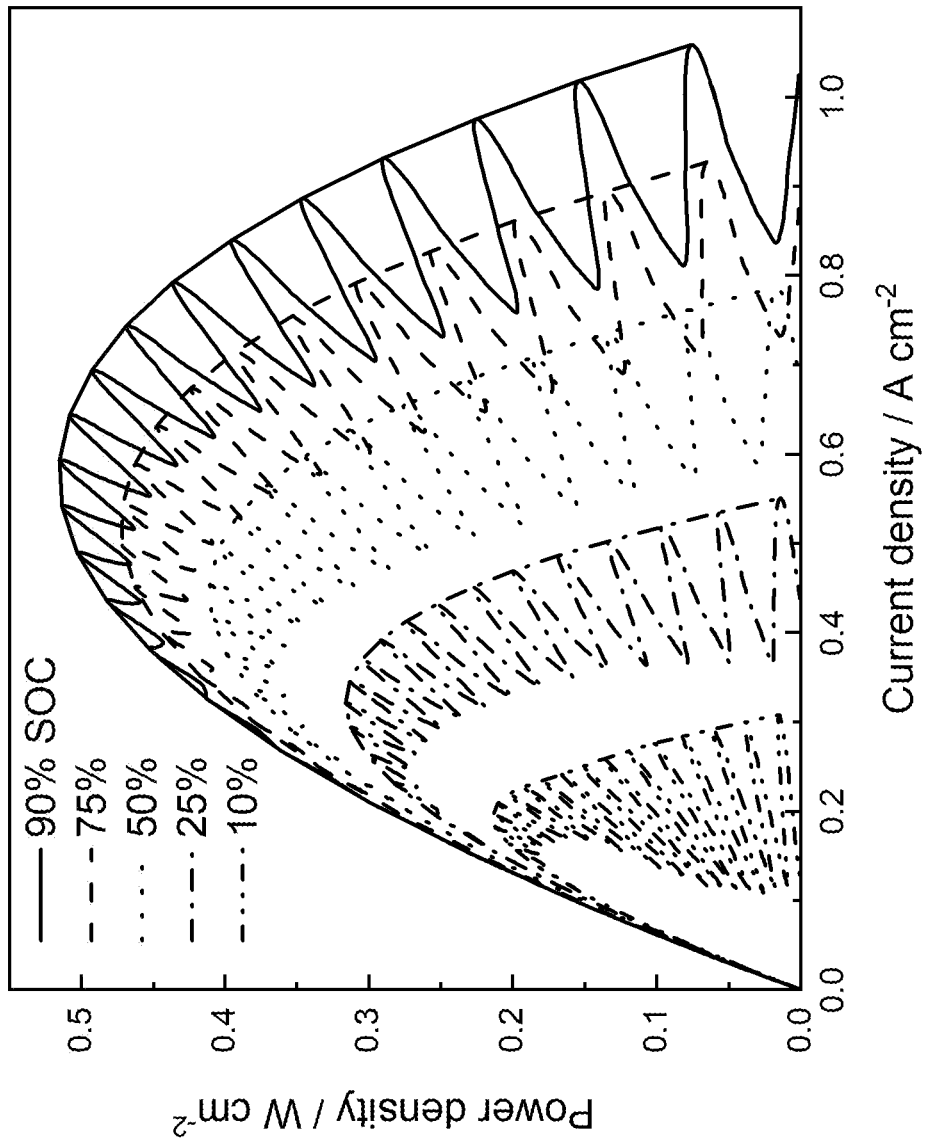
FIG. 9C illustrates iron-chromium cell polarization data with fitting of pump pulses illustrating the cell power density versus current density at varying SOC plotted with original pump pulse data.
Figure 9D:
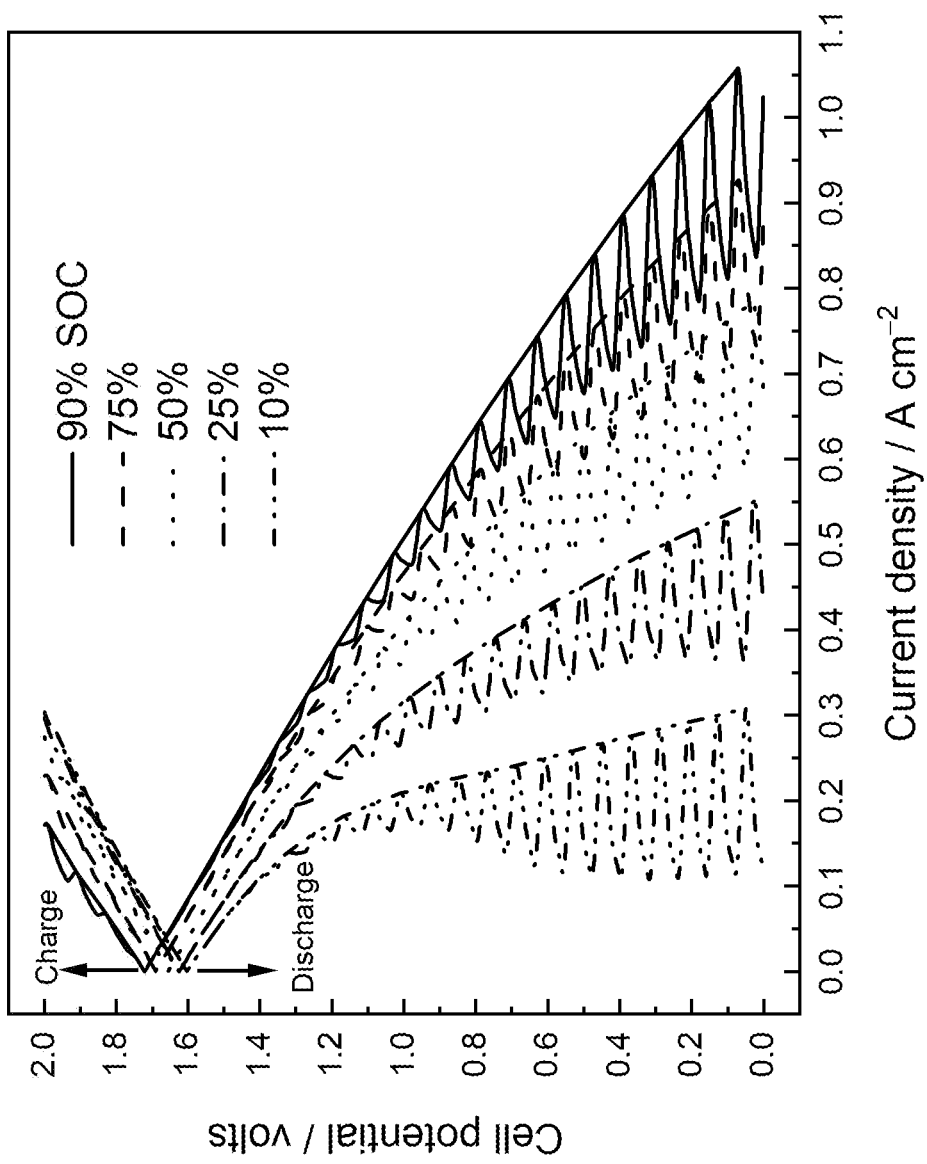
FIG. 9D illustrates iron-chromium cell polarization data with fitting of pump pulses illustrating the cell polarization data at varying SOC plotted with original pump pulse data.
Figure 10A:
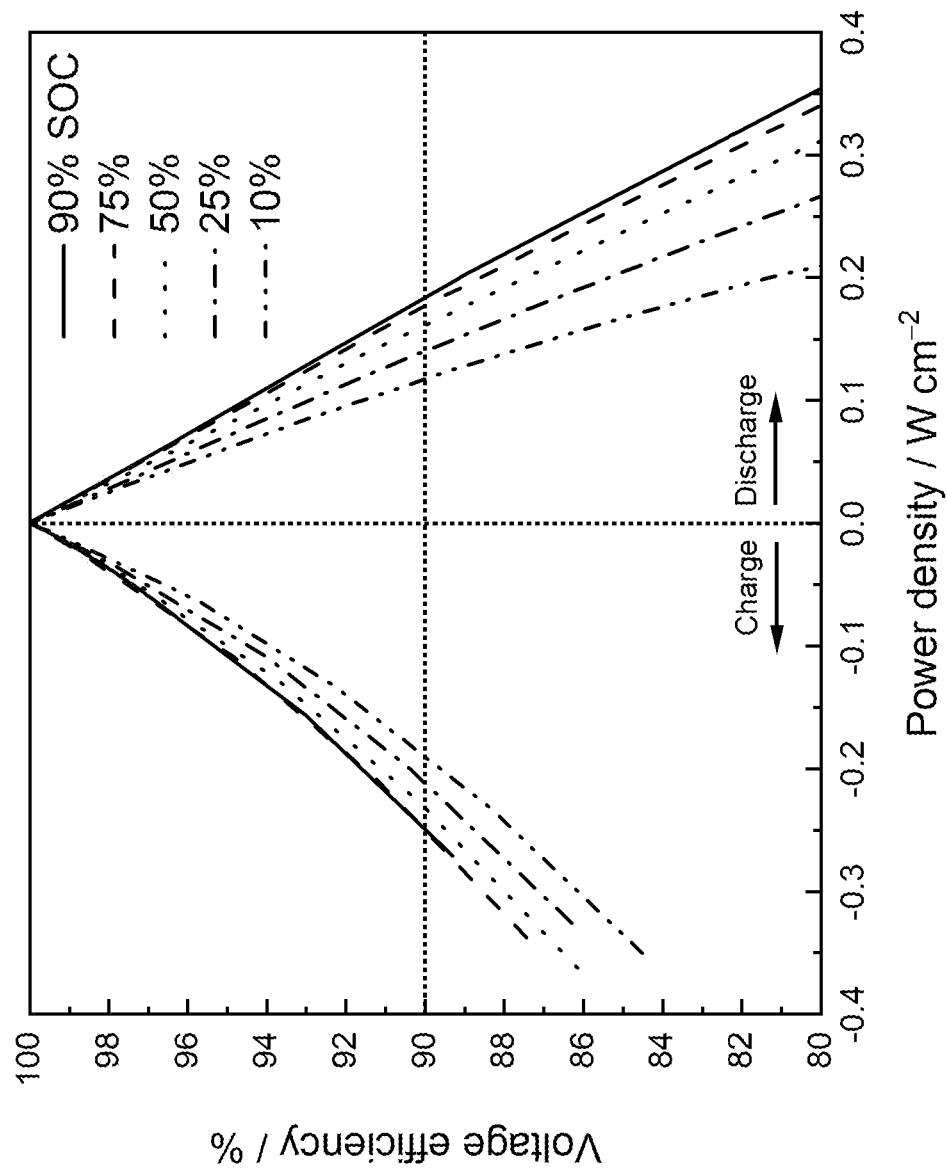
FIG. 10A illustrates the chromium-bromine cell polarization data with fitting of pump pulses illustrating the voltage efficiency versus power density at 5 different SOC.
Figure 10B:
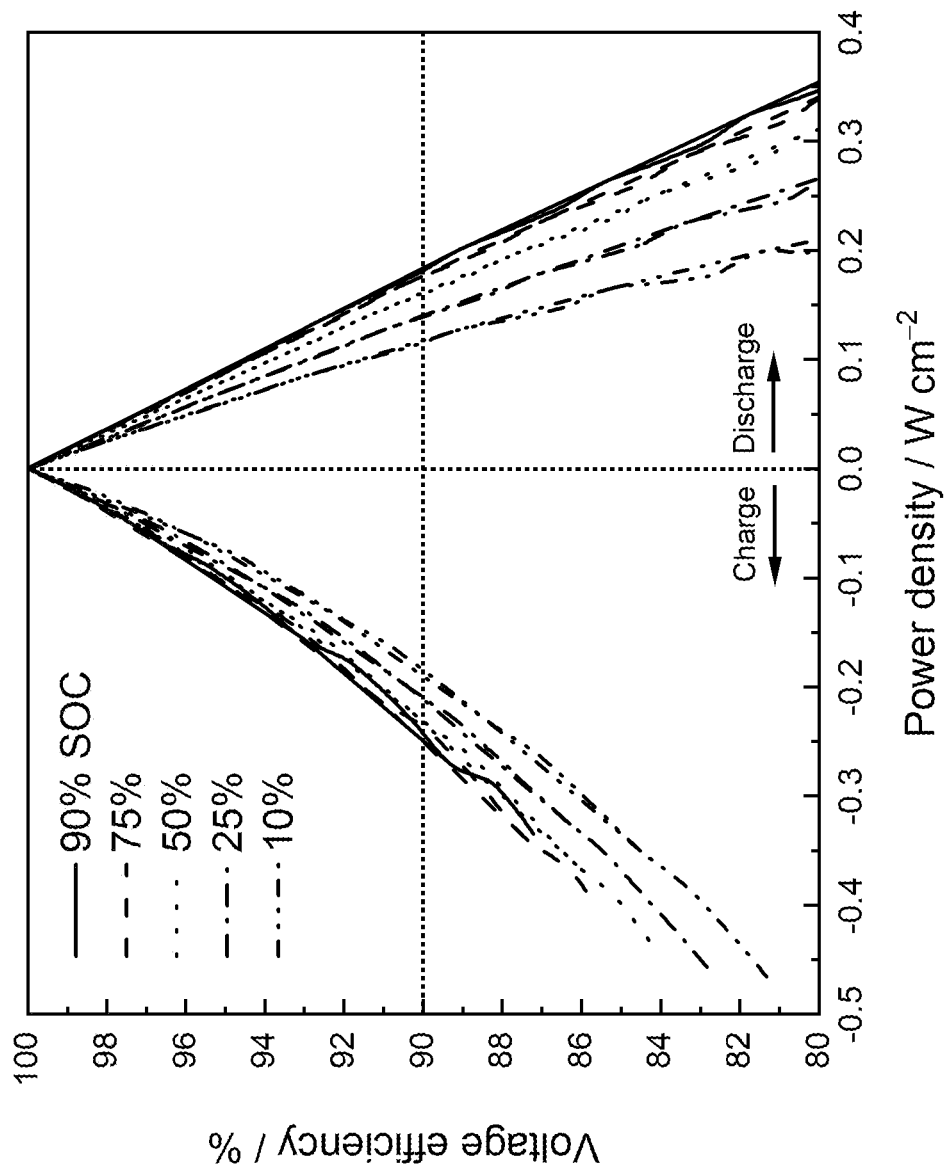
FIG. 10B illustrates the chromium-bromine cell polarization data with fitting of pump pulses illustrating the voltage efficiency versus power density at 5 different SOC plotted with original pump pulse data.
Figure 10C:
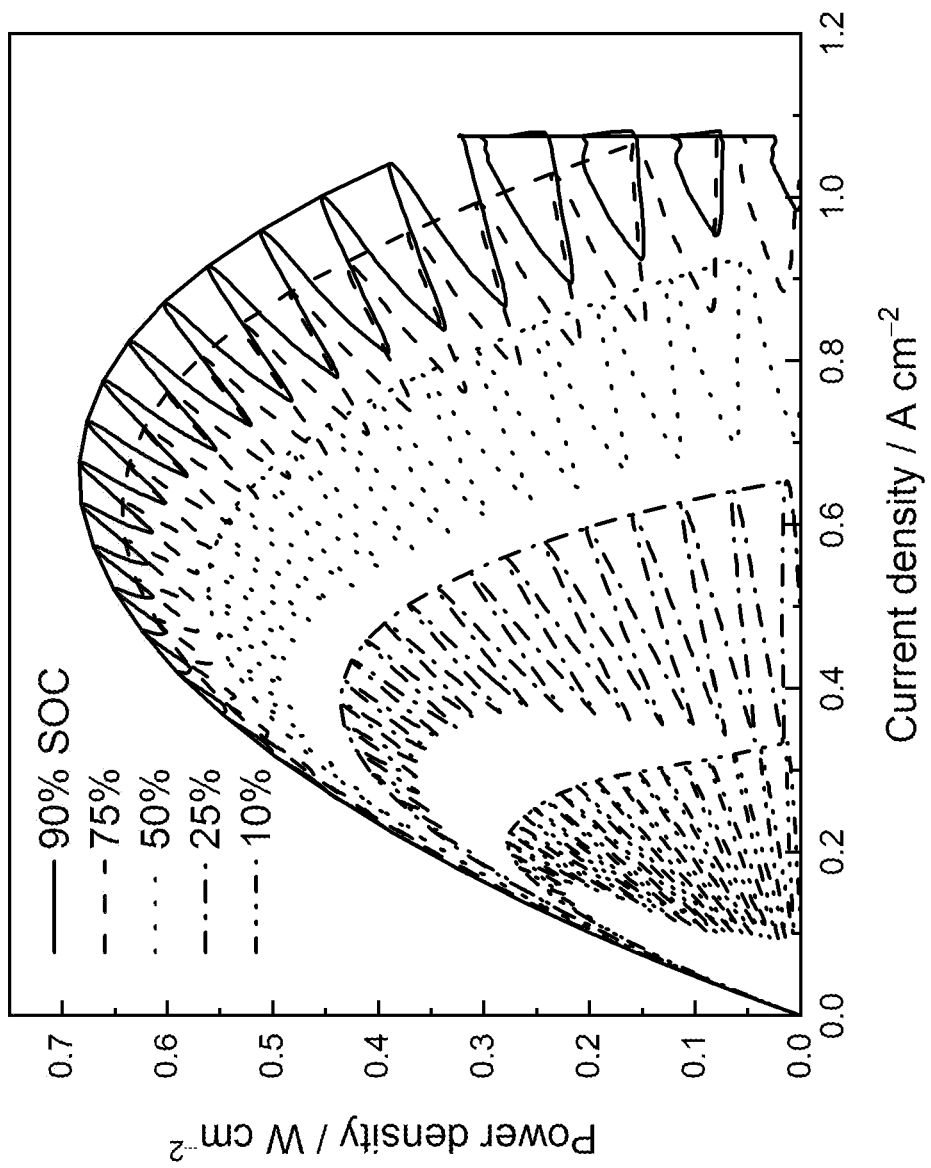
FIG. 10C illustrates the chromium-bromine cell polarization data with fitting of pump pulses illustrating the cell power density versus current density at varying SOC plotted with original pump pulse data.
Figure 10D:
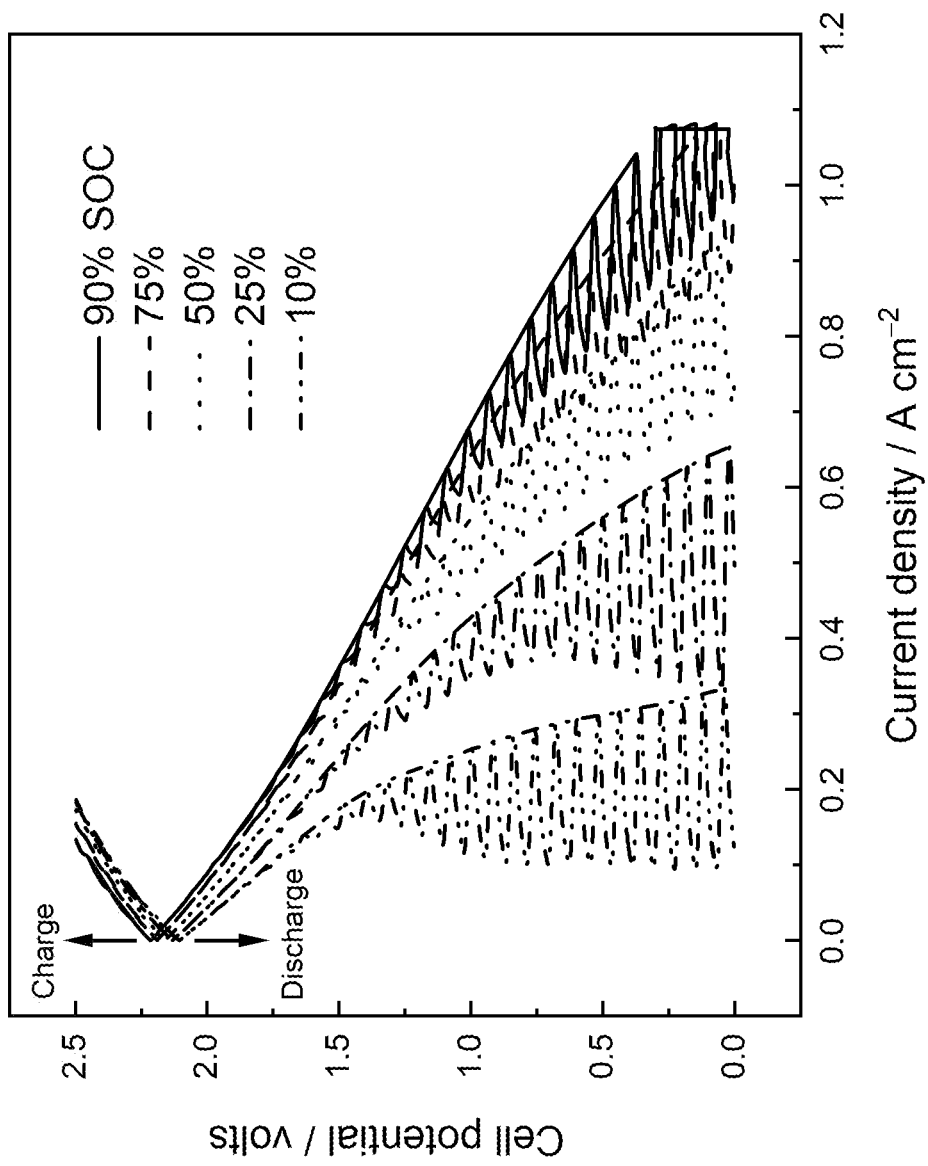
FIG. 10D illustrates the chromium-bromine cell polarization data with fitting of pump pulses illustrating the cell polarization data at varying SOC plotted with original pump pulse data.
Figure 11:
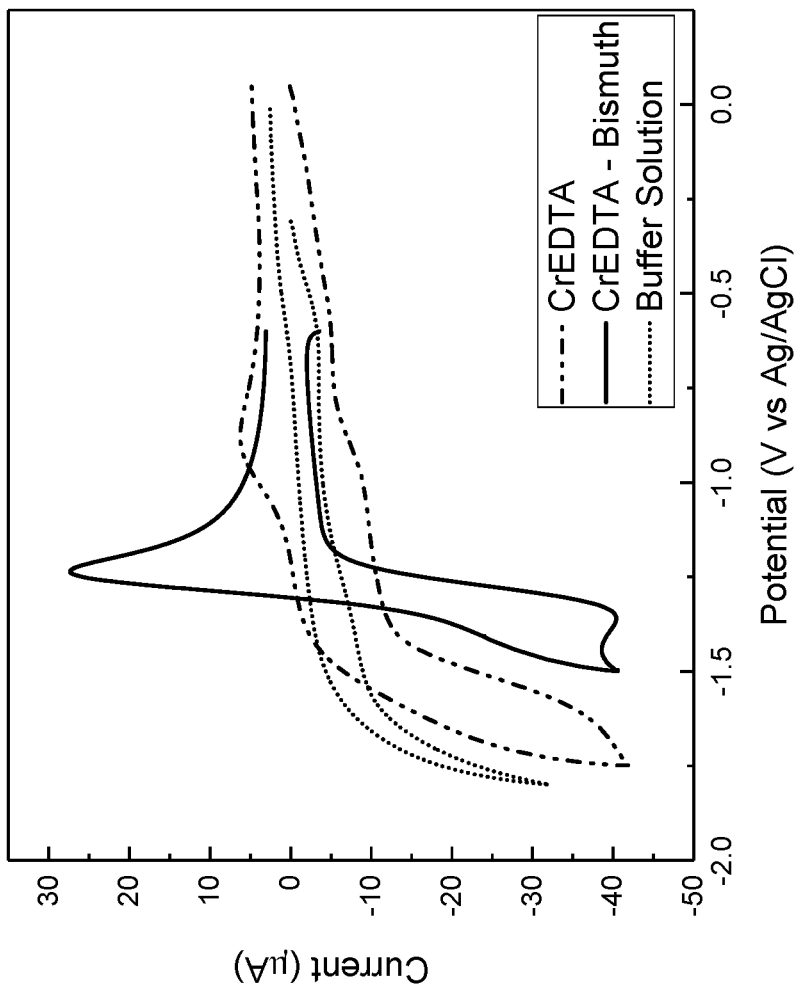
FIG. 11 illustrates CrEDTA (5 mM) at a pH of 9 in a borate buffer.
Figure 12:
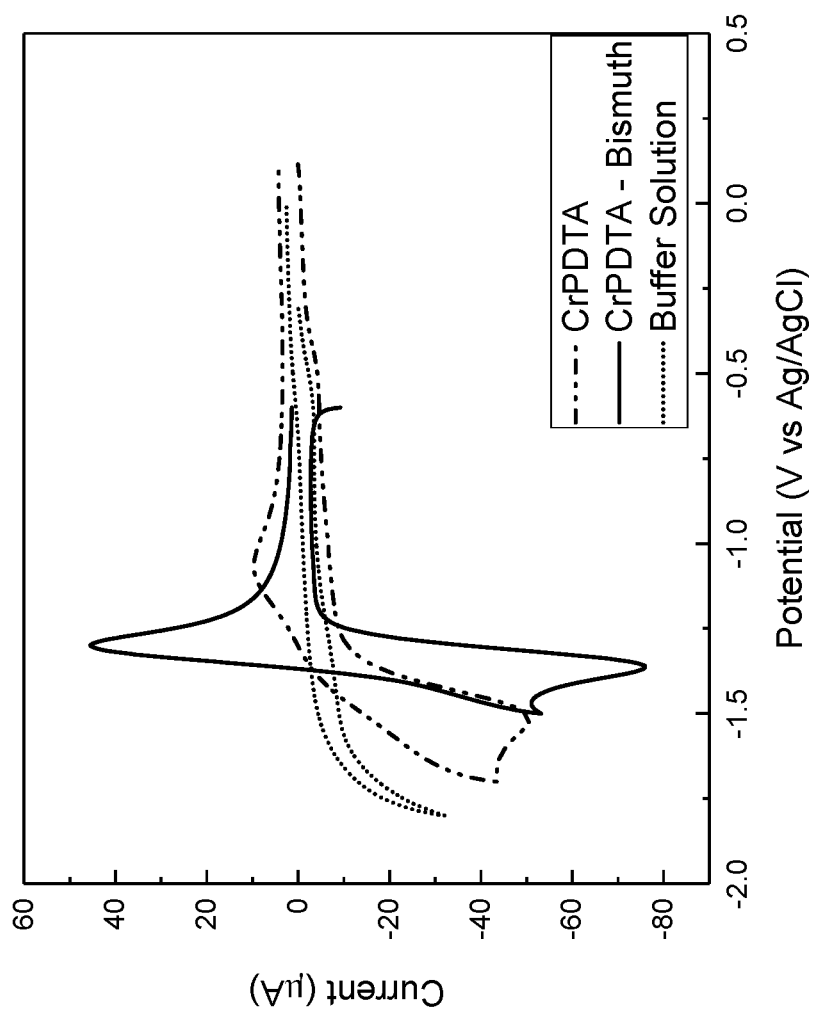
FIG. 12 illustrates a CrPDTA (5 mM) at a pH of 9 in a borate buffer.
Figure 13:
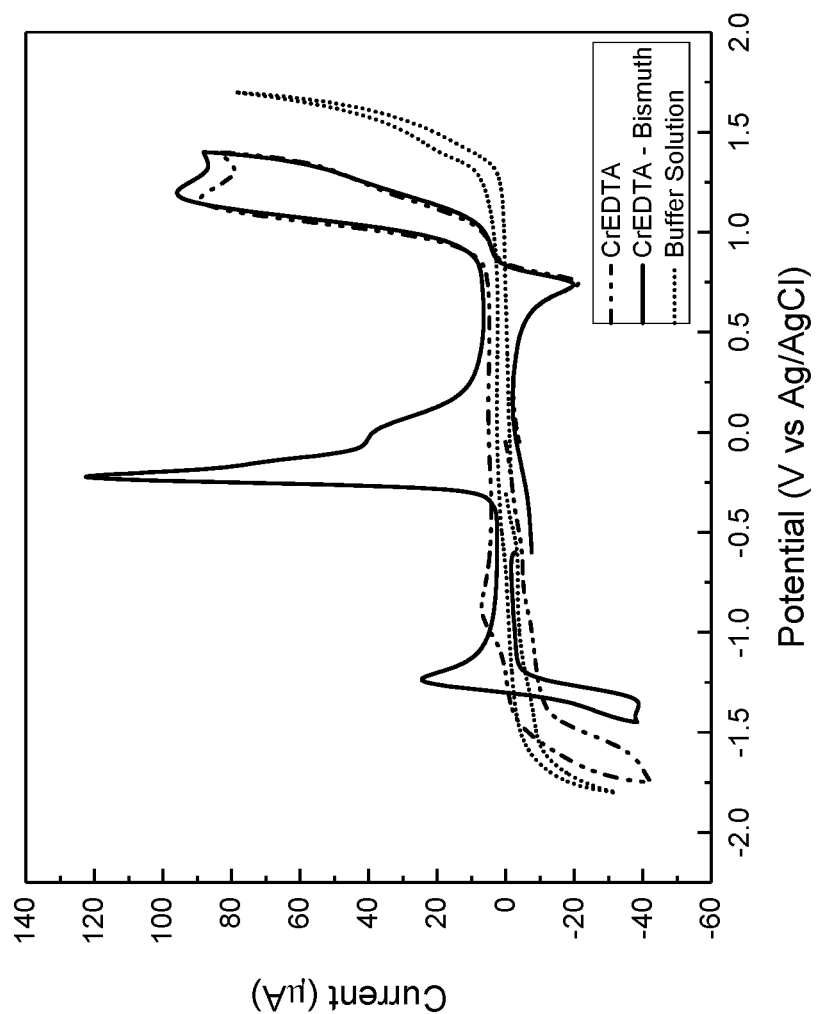
FIG. 13 illustrates a CrEDTA (5 mM) at a pH of 9 in a borate buffer over a potential of −2 to 2.
Figure 14:
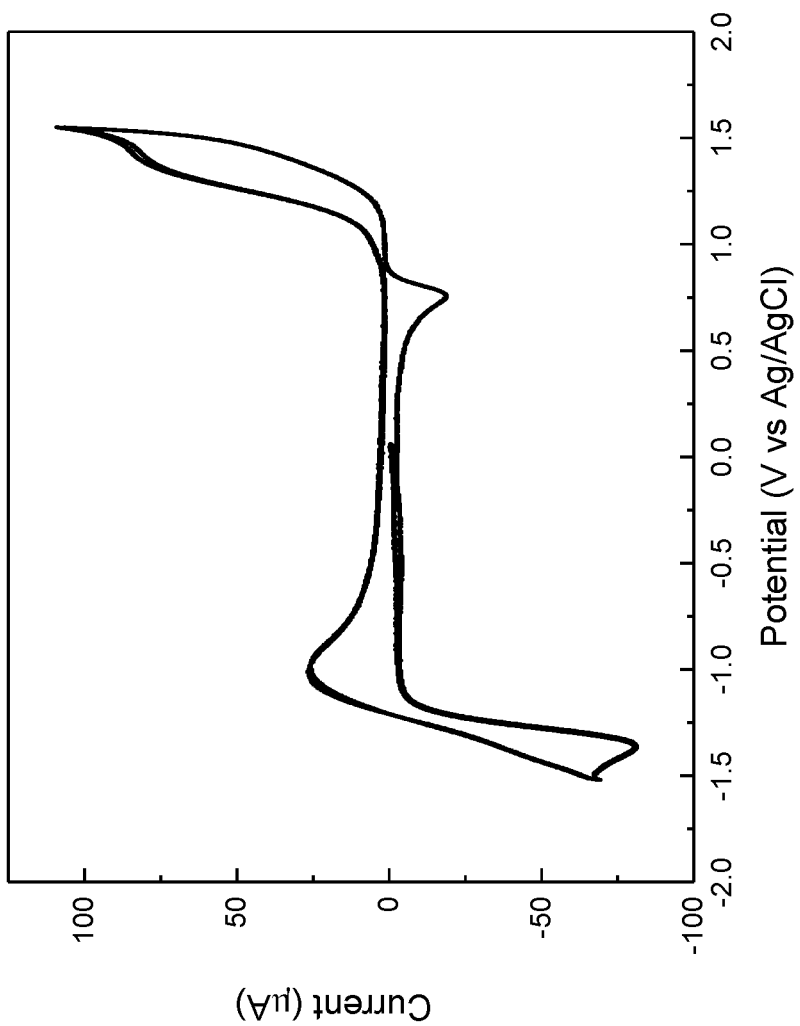
FIG. 14 illustrates a CrEDTA (approximately 10 mM) pH of 5.5 in a NaOAc buffer (without bismuth on the electrode)
Figure 15A:
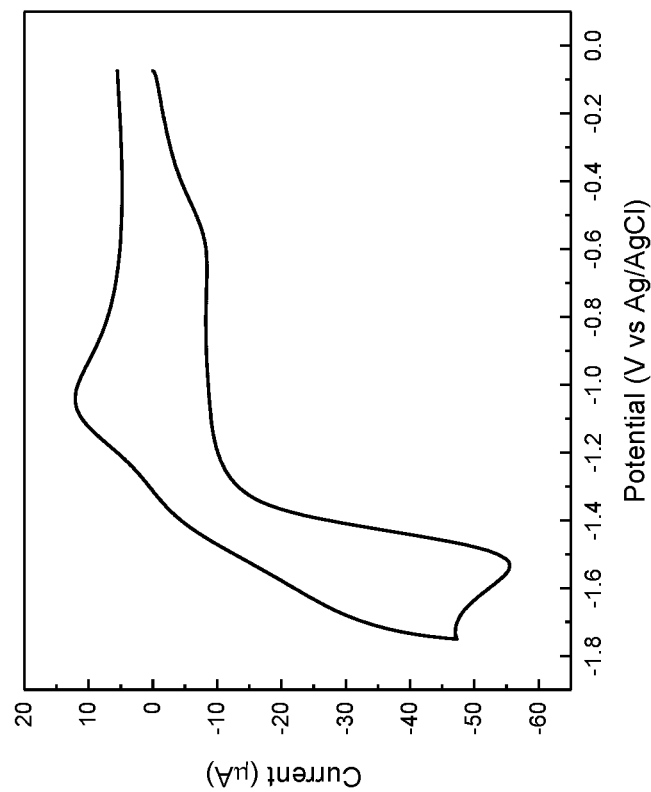
FIG. 15A illustrates a single cycle of KCrPDTA (~5 mM) pH 9 $NaHCO_3$ (without bismuth)
Figure 15B:
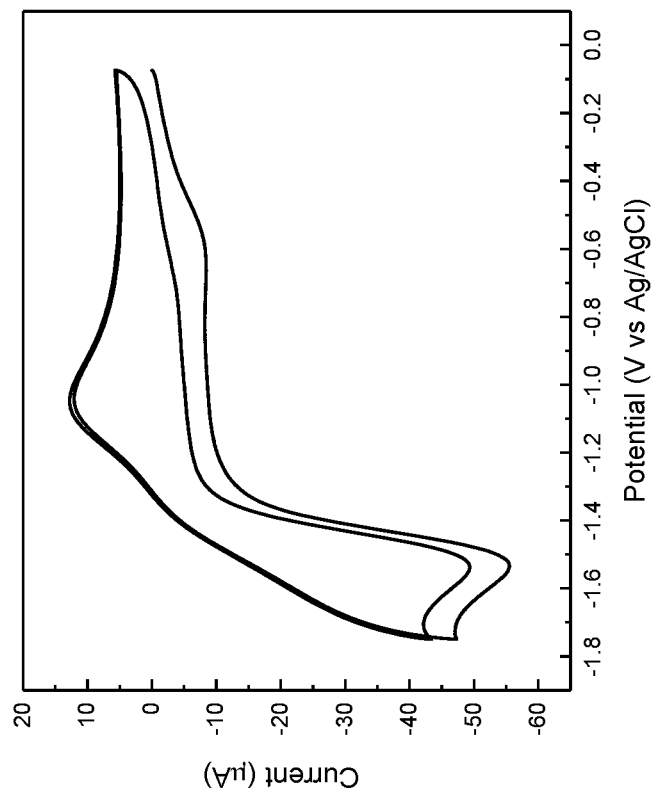
FIG. 15B illustrates two cycles of KCrPDTA (~5 mM) pH 9 $NaHCO_3$ (without bismuth)
Figure 16A:
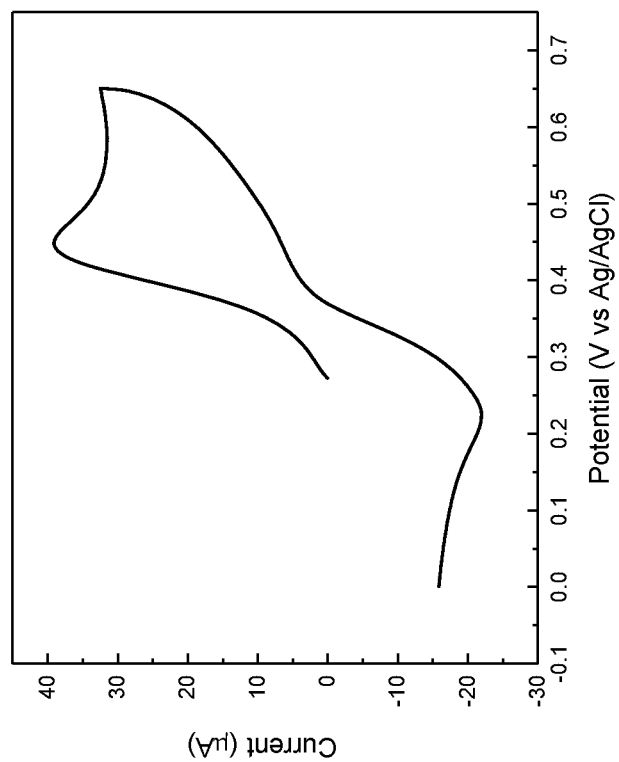
FIG. 16A illustrates a single cycle of a MgMnBDTA (~10 mM) at a pH of about 9 where the buffer is $NaHCO_3$.
Figure 16B:
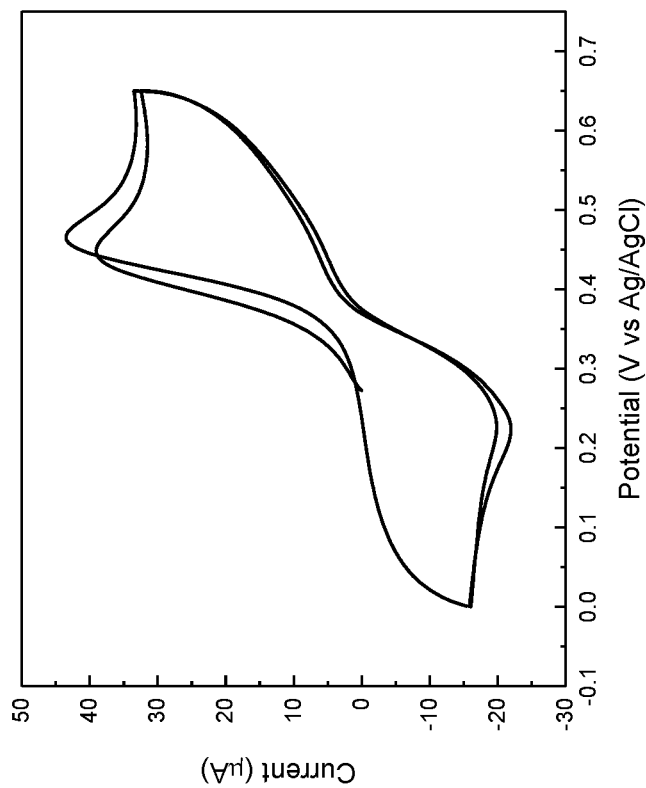
FIG. 16B illustrates two cycles of a MgMnBDTA (~10 mM) at a pH of about 9 where the buffer is $NaHCO_3$.
Figure 17A:
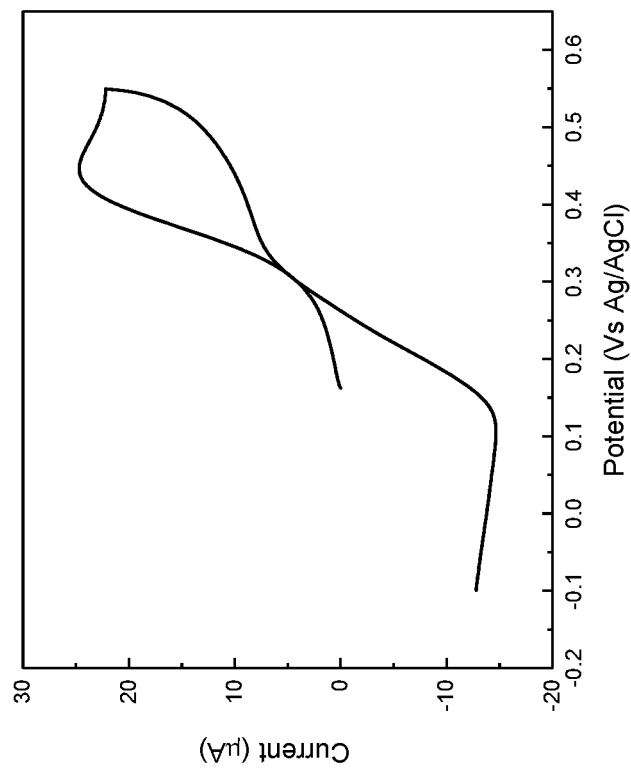
FIG. 17A illustrates a single cycle of $Na_2$MnPDTA (~5 mM) at a pH of 9 and a buffer of $NaHCO_3$.
Figure 17B:
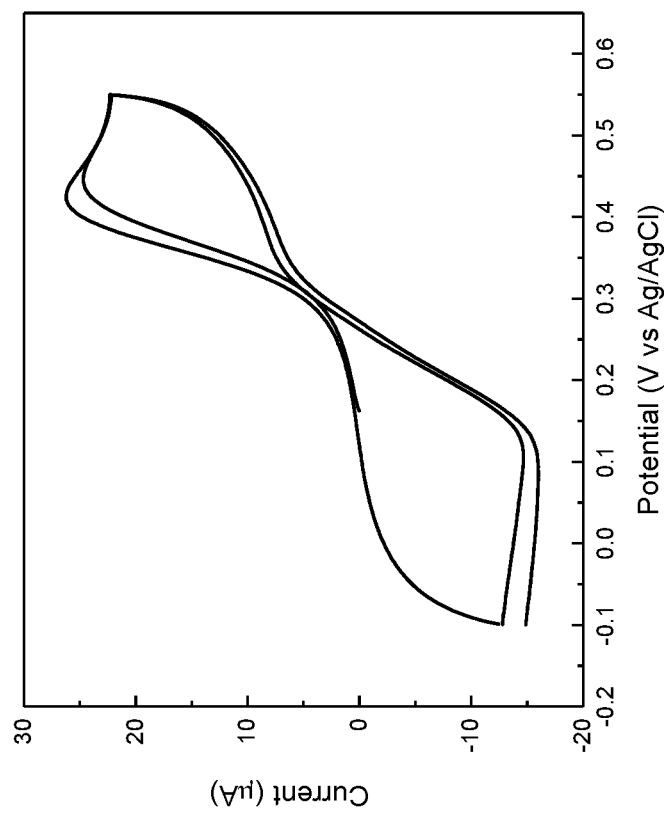
FIG. 17B illustrates two cycles of $Na_2$MnPDTA (~5 mM) at a pH of 9 and a buffer of $NaHCO_3$.

Because the CrPDTA redox couple operates near the negative limit of H$_2$ evolution on carbon, a redox couple more positive than Fe(CN)$_6^{3-/4-}$ is required to further increase the battery voltage. Therefore, the Br$_2$/Br$^-$ redox couple was chosen to produce an RFB with a potential over 2.1 V. FIG. 4A shows the discharge curve of a chromium-bromine (CrBr) RFB, wherein the cell maintains an operating voltage above 2 volts for nearly the complete discharge time (FIG. 4A). Cycling at ±0.1 A cm$^{-2}$ to both 80% and 90% SOC results in stable charge-discharge cycles (FIG. 4A, inset) with 97% current efficiency and an overall energy efficiency of 76% per cycle (FIG. 8B). Cell polarization curves are reported in FIG. 4B and the open circuit potential ranged from 2.05 to 2.2 V between 5 and 95% SOC (FIG. 4B, inset). The peak power ranged from over 0.2 to 0.6 W cm$^{-2}$, with a maximum of 0.684 W cm$^{-2}$ observed at 90% SOC (FIG. 4C).

Summary

These results demonstrate two high-performance aqueous RFBs with higher operating voltages than the majority of non-aqueous or hybrid RFB systems. One claim favoring non-aqueous electrolytes for high-voltage batteries is that water is limited by the water splitting potential (1.23 V); however, water is vastly more thermodynamically stable than most organic solvents with respect to their elemental compositions. The fact that water's electrolysis products, H$_2$ and O$_2$, spontaneously recombine to reform water is an enormous advantage over non-aqueous electrolytes because water splitting can be mitigated by pH rebalancing cells. Li-ion batteries operate at high voltage in non-aqueous electrolyte by forming a corrosion layer called a solid-electrolyte interphase (SEI) that stabilizes and protects the electrodes from contact with the electrolyte. Similarly, Cr' ions are kinetically stabilized in aqueous solution by using a robust organic chelate as a barrier, or a molecular SEI, that excludes water from interacting with the reactive metal center. The coordination of water or protons to a metal ion is usually considered to be one of the first mechanistic steps in both anodic and cathodic processes in water splitting.

The CrPDTA electrolyte addresses many of the current limitations of redox flow batteries and offers a new pathway to dramatically lower the cost of grid-scale energy storage. The use of CrPDTA should enable more rapid market penetration than many organic electrolytes because EDTA and related chelates are already commodity chemicals manufactured on a scale of 10$^8$ kg yr$^{-1}$ for fertilizer, water treatment, and consumer products. More generally, the primary coordination of a metal complex can be controlled through the use of inexpensive mass-produced chelates can kinetically stabilize aqueous flow batteries at potentials in large excess of the thermodynamic water splitting potential. The disclosure, thus, can provide a general approach in imparting kinetic stability to high-voltage aqueous batteries and also will carry wider implications for managing $H_2$ evolution in other electrochemical applications.

Example 5

CrPDTA was synthesized using $CrCl_3 \cdot 6H_2O$ (21.3 g, 80 mmol) and 1,3-diaminopropane-N,N,N',N'-tetraacetic acid (27.5 g, 90 mmol), which were dissolved in 30 mL of deionized water and heated to 110° C. After 1 hour of heating, solid KOH (10 g) was added in 0.5 g increments every 15 seconds. After 24 hours, 16 mL of 5 M KOH was added slowly in 1 mL increments. Another 16 mL of 5 M KOH was added after an additional 24 hours of heating. The pH of the solution was monitored during the addition of KOH and kept below 2.5 until after 48 hours of heating. After 72 hours of total reaction time, the solution was cooled and filtered with the resulting final solution having a pH between 5 and 6. No further purification was performed.

Example 6

CrEDTA was synthesized with $CrCl_3 \cdot 6H_2O$ (21.3 g, 80 mmol) and ethylenediamine tetraacetic acid (26.28 g, 90 mmol), which were dissolved in 30 mL of deionized water and heated to 110° C. After 1 hour of heating, solid KOH (10 g) was added in 0.5 g increments every 15 seconds. After 24 hours, 16 mL of 5 M KOH was added slowly in 1 mL increments. Another 16 mL of 5 M KOH was added after an additional 24 hours of heating. The pH of the solution was monitored during the addition of KOH and kept below 2.5 until after 48 hours of total reaction time, the solution was cooled and filtered with the resulting final solution having a pH between 5 and 6. No further purification was performed. About 0.125 equivalents of free ligand (chelate) are present in solution after the synthesis of Example 1, and 0.125 equivalents of free ligand and 3 equivalents of KCl are present in solution after the synthesis of Examples 5 and 6, respectively.

Example 7

$K_2[Fe(III)DTPA]$ was synthesized with $FeCl_3$ (0.810 g, 5.0 mmol) and $H_5DTPA$ (2.162 g, 5.5 mmol) were added to deionized (DI) $H_2O$ (10 mL). With active stirring, $K_2CO_3$ (2.070 g, 15 mmol) was slowly added. The solution was stirred until the evolution of $CO_2$ subsided. A dark yellow-brown solution remained with a final pH of 9. No further purification was performed. About 0.1 equivalents of free ligand and 3 equivalents of KCl are present in solution after synthesis.

Example 8

Half-cell measurements were made using cyclic voltammetry (CV), which was conducted using a Gamry Interface 1000 potentiostat, an Ag/AgCl aqueous reference electrode (3 M NaCl filling solution), a Pt wire counter electrode, and a 3-mm-diameter glassy carbon working electrode, unless otherwise noted. Solutions were first sparged with an inert gas, for example $N_2$, helium, neon, or argon, or combinations thereof, for at least 15 minutes and then kept under a blanket of an inert gas, such as $N_2$, helium, neon, or argon, or combinations thereof, while tests were performed. All testing was performed at ambient temperatures. For carbon paper cyclic voltammetry experiments, the same setup was used as with the glassy carbon electrode, but the working electrode was a piece of carbon paper. For all chromium complexes and $Fe(CN)_6$ solution 5 mM solutions were utilized for all CV experiments except those utilizing carbon paper electrodes which utilized 50 mM solutions. Other metal chelate complexes have concentrations that are specified in the figure captions.

Example 9

A 5 $cm^2$ single-cell flow battery was purchased from Fuel Cell Technologies Inc. with the acid cell configuration, so that the tubing carrying the electrolyte feeds directly into the graphite flow plate without contacting the aluminum or stainless-steel cell components. The flow plates comprised Poco graphite blocks with 5 $cm^2$ single serpentine flow fields. Unless otherwise noted, the flow cell was comprised of a Nafion 212 membrane (50 μm thick, 3 cm×3 cm) that was soaked in DI water for a minimum of 12 hours and gasketed with a 0.002" PTFE sheet and also comprised of five stacked sheets (280 μm thick and 5 $cm^2$ each) of GDL 39 AA carbon paper (SGL) that were heated to 150° C. in air for 12 hours and used on each side with a 0.04" PTFE gasket providing 27% compression. The cell was bolted together and tightened with a torque wrench to 10 N m. Due to the reactivity of Cr(II)PDTA and Cr(II)EDTA solutions with stainless steel and other metals, either a PTFE diaphragm pump (Cole-Parmer) or peristaltic pump utilizing C-Flex ultra L/S 16 tubing was used with an average fluid flow rate of between 40-60 mL min'. The fluids were flowed using non-reactive ⅛" OD, 1/16" ID perfluoroacetoxy (PFA) tubing and PFA compression fittings. Solutions were contained either in 60 mL PFA column component vessels capped with 58 mm transfer closures with two ⅛" OD compression fitting ports (Savillex) or in 100 mL glass round bottom flasks fitted with rubber septa containing holes drilled for ⅛" OD tubing. Flow cell experiments were conducted using a Gamry Interface 5000E potentiostat/galvanostat. Flow battery experiments utilized 10 mL of the chromium solution unless otherwise noted.

Example 10

Figure 18:
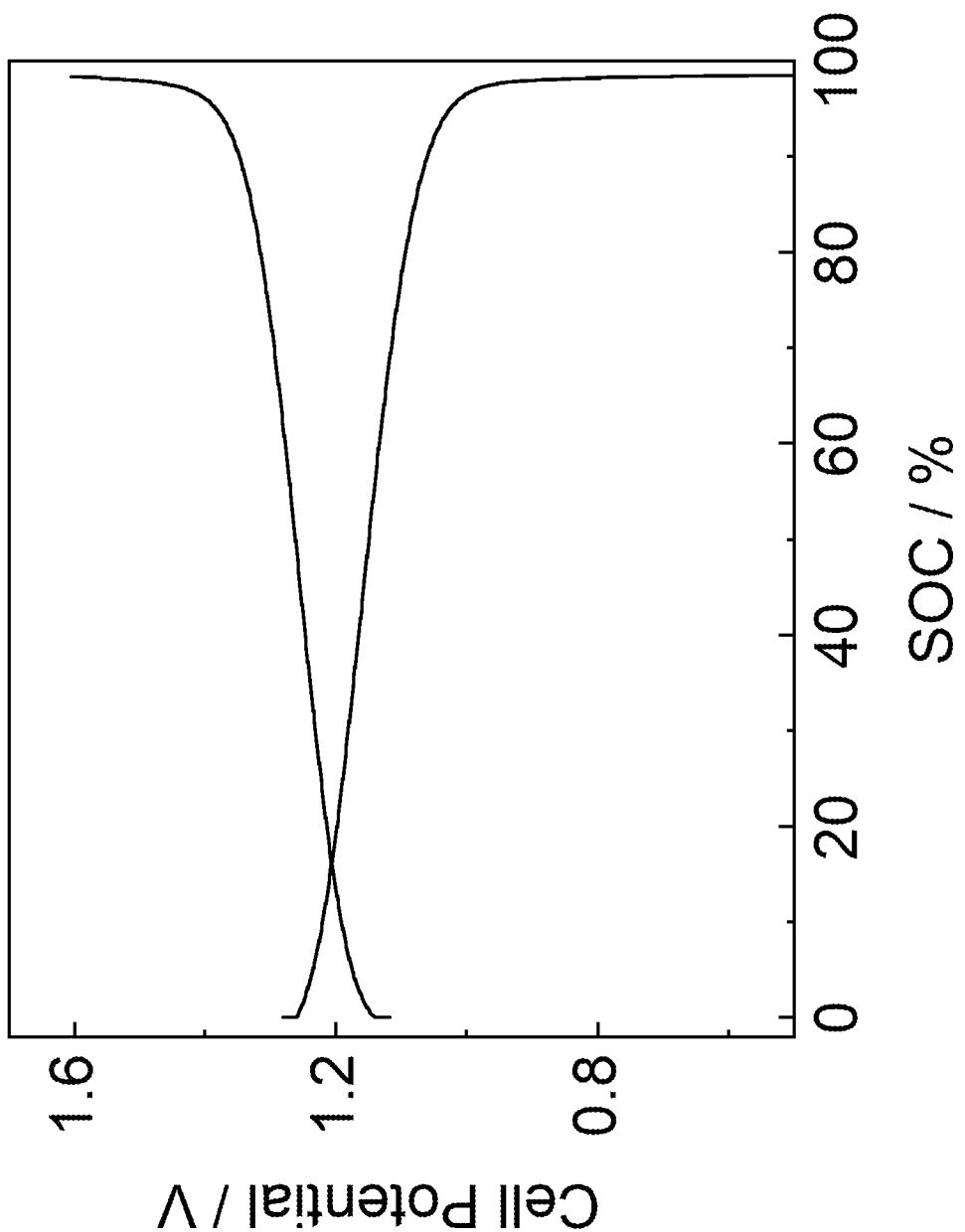
FIG. 18 illustrates a 0.5 M CrPDTA vs. FeDTPA flow battery cycle in 0.2 M $K_2B_4O_7$ buffer at pH 9 at ±20 mA/cm$^2$.

A negative electrolyte containing the same system as used in example 5 was prepared. A positive electrolyte containing $K_2FeDTPA$ as an active material for the positive electrode was prepared as described in example 7. The FeDPTA was prepared to give a concentration of 0.5 M. $K_2B_4O_7$ was added to a concentration of 0.2 M. The CrPDTA was pre-charged against a sacrificial $Fe(CN)_6$ solution similar to that used in example 10. When operated at a current density of ±20 mA/$cm^2$ had a coulombic efficiency of 100.3±0.4% and energy efficiency of 92%. The capacity of this battery for the maximum storage was found to be 36.2 Ah/liter. The cell achieved a maximum output power of 216 mW $cm^2$ and had an equilibrium potential of 1.18 V. The cell had a polarization resistance of 2.58 ohms $cm^2$. FIG. 18 illustrates a 0.5 M CrPDTA vs. FeDTPA flow battery cycle in 0.2 M $K_2B_4O_7$ buffer at pH 9 at ±20 mA/$cm^2$.

Example 11

Figure 19:
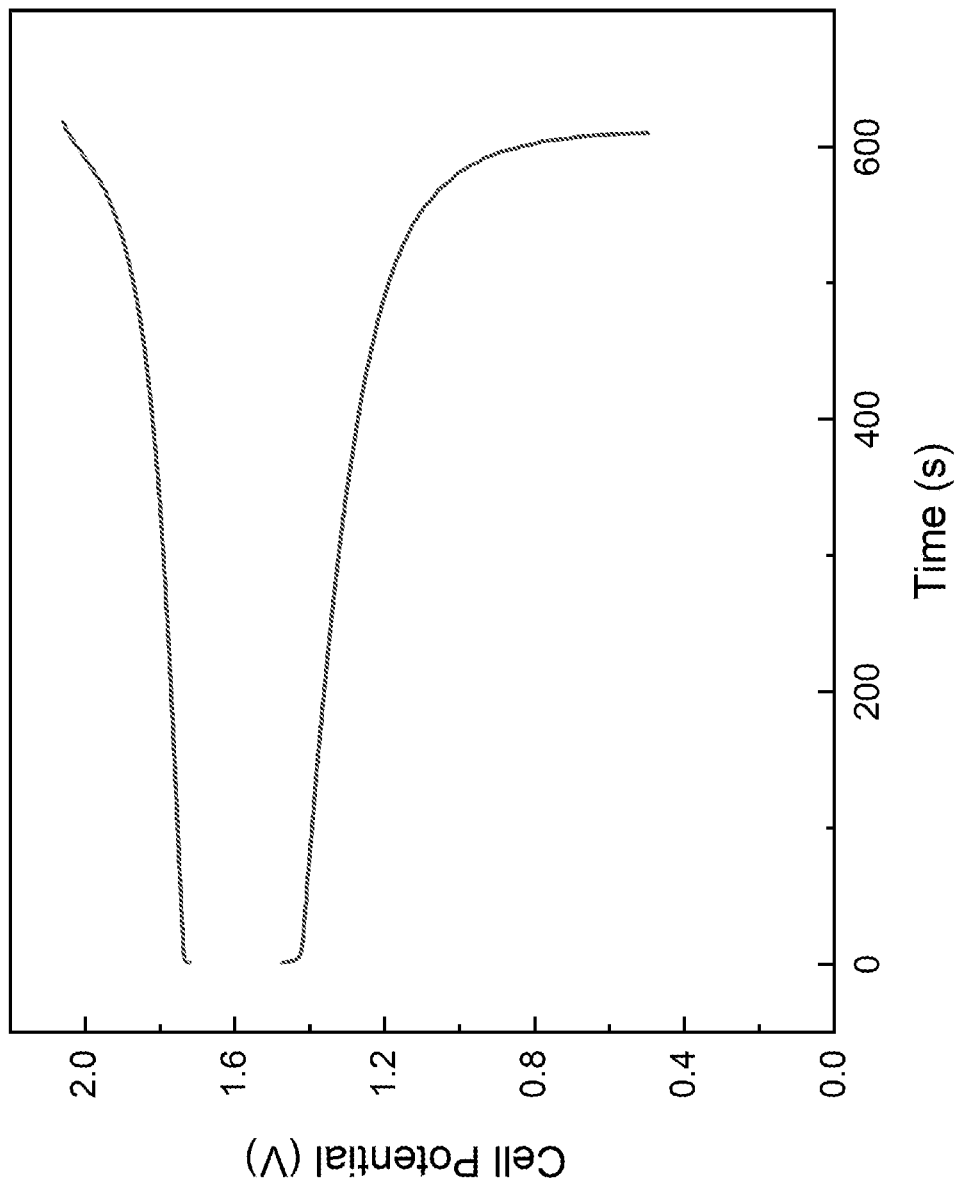
FIG. 19 illustrates a single 0.2 M CrPDTA and 0.2M CrEDTA vs Fe(CN)$_6$ flow battery cycle to 80% SOC in $K_2B_4O_7$ buffer at ±100 mA/cm$^2$.

A negative electrolyte containing a NaCrPDTA and potassium 1,2-ethylenediaminetetraacetic acid (KCrEDTA) redox system as the active materials for the negative electrode was prepared as described in examples 5 and 6 but with the alternate cation (such that a different cationic form is formed by the addition of a base comprised of the desired cation, for example NaOH or NH$_4$OH). The concentration of the CrPDTA was 0.2 M and CrEDTA was 0.2 M. Potassium tetraborate (K$_2$B$_4$O$_7$) was added to a concentration of 0.2 M and the resulting pH was 8.75. A positive electrolyte containing the same system as used in example 10 was prepared. The resulting flow battery, assembled as described in example 9, when operated utilizing 80% of the total electrolyte capacity at a current density of ±100 mA/cm$^2$ had a coulombic efficiency of 98.7% and energy efficiency of 72.7%. FIG. 19 illustrates a single 0.2 M CrPDTA and 0.2M CrEDTA vs Fe(CN)$_6$ flow battery cycle to 80% SOC in K$_2$B$_4$O$_7$ buffer at ±100 mA/cm$^2$.

Example 12

Figure 20:
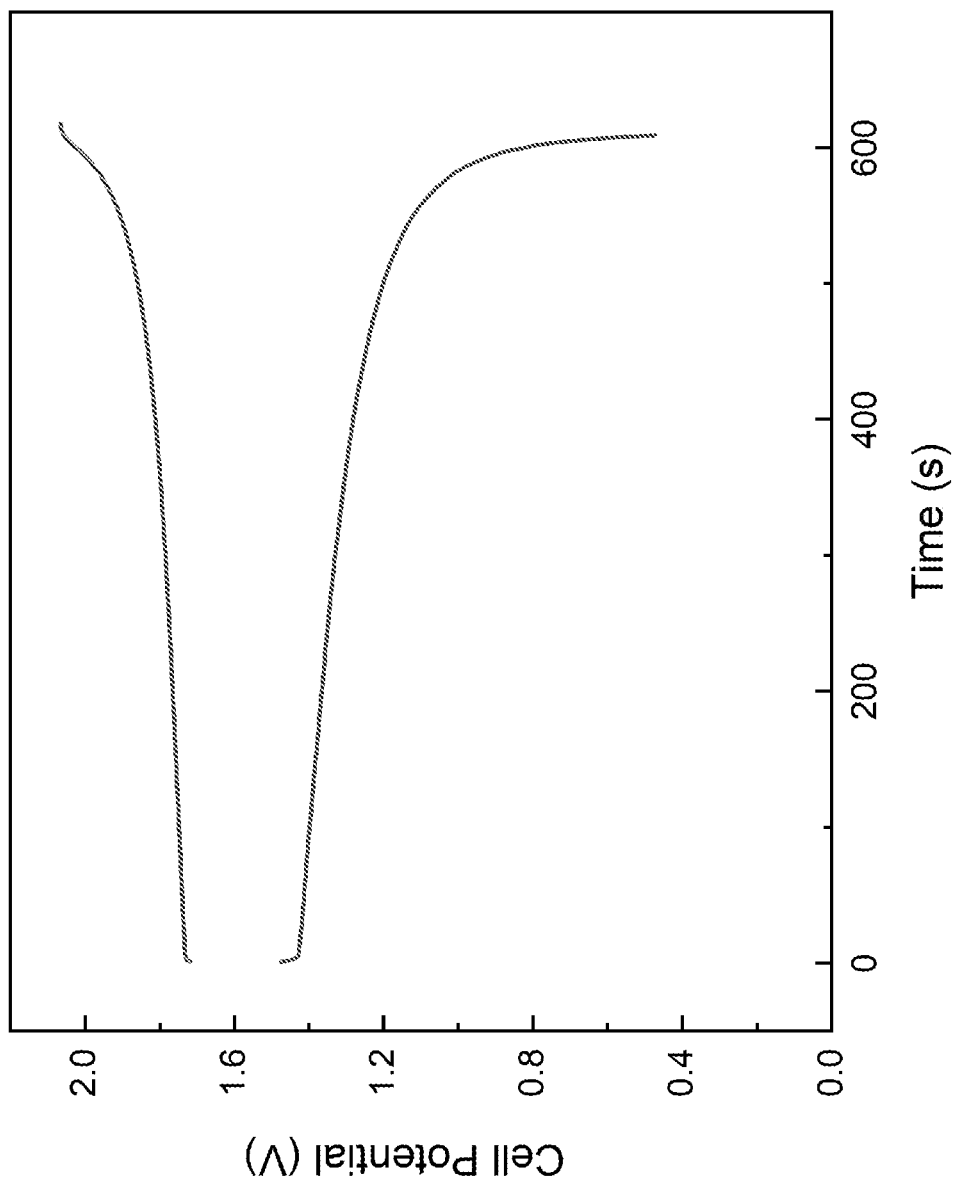
FIG. 20 illustrates a single 0.2 M CrPDTA and 0.2M CrEDTA vs Fe(CN)$_6$ flow battery cycle to 80% SOC in $K_2B_4O_7$ and NTA buffer at ±100 mA/cm$^2$.

To the negative electrolyte from example 14, 1 mL of 1.0 M NTA solution at pH 10 was added. When continuing to utilize the negative electrolyte described in example 14, the resulting flow battery, when operated utilizing 80% of the total electrolyte capacity at a current density of ±100 mA/cm$^2$, had a coulombic efficiency of 98.5% and energy efficiency of 73.2%. FIG. 20 illustrates a single 0.2 M CrPDTA and 0.2M CrEDTA vs Fe(CN)$_6$ flow battery cycle to 80% SOC in K$_2$B$_4$O$_7$ and NTA buffer at ±100 mA/cm$^2$.

Example 13

Figure 21:
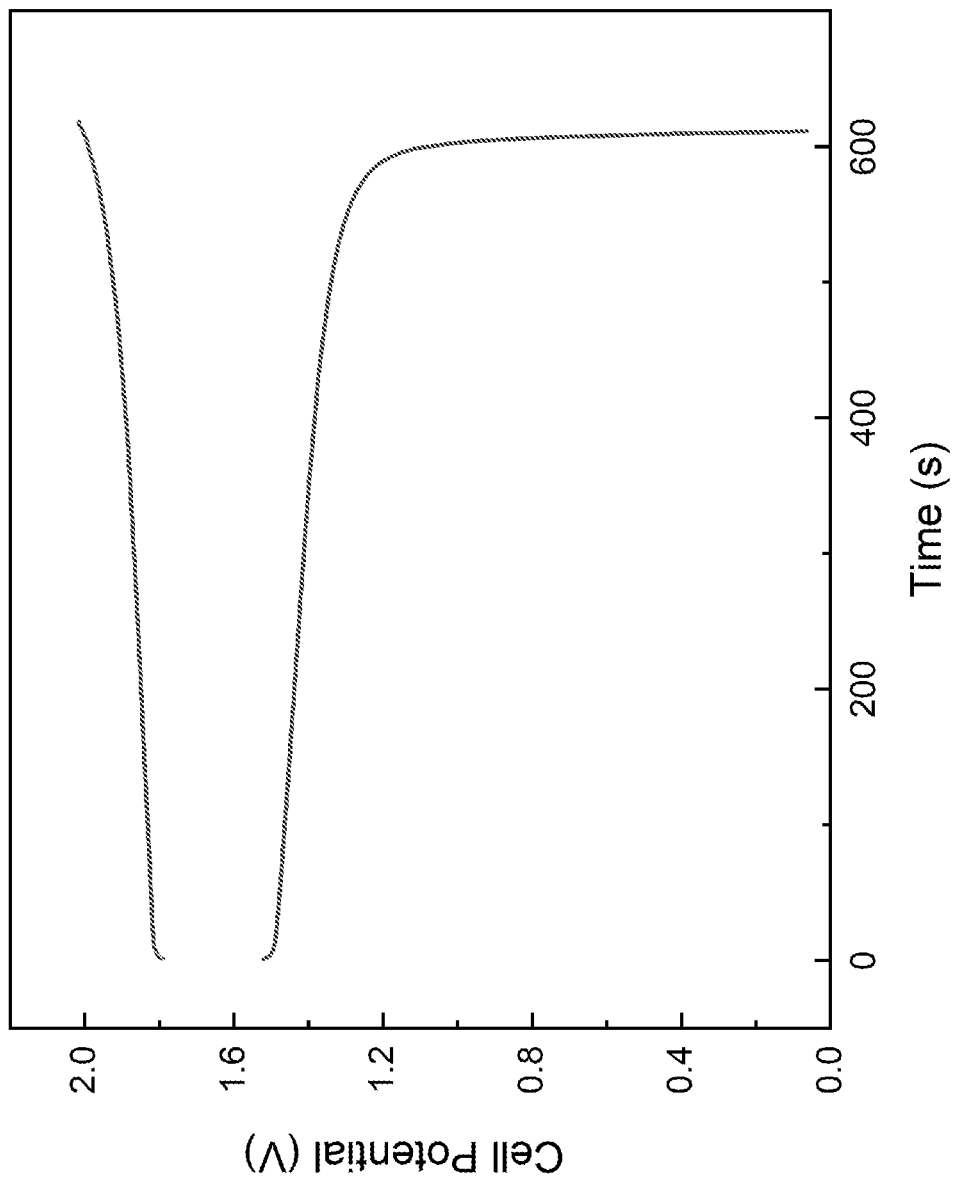
FIG. 21 illustrates a single 0.4 M CrPDTA vs Fe(CN)$_6$ flow battery cycle to 80% SOC in PDTA buffer at ±100 mA/cm$^2$.

A negative electrolyte containing the KCrPDTA redox system as the active material for the negative electrode was prepared as described in example 5, but with only the excess PDTA from the reaction described in example 5 as a buffer. The pH of the solution was adjusted to pH 8.32 with KOH and the concentration of the CrPDTA was 0.4 M. The resulting PDTA buffer would be 0.045 M based on the excess ligand from the synthesis. A positive electrolyte containing the same system as used in example 10 was prepared. The resulting flow battery, assembled as described in example 9, when operated utilizing 80% of the total electrolyte capacity at a current density of ±100 mA/cm$^2$ had a coulombic efficiency of 98.9% and energy efficiency of 74.6%. FIG. 21 illustrates a single 0.4 M CrPDTA vs Fe(CN)$_6$ flow battery cycle to 80% SOC in PDTA buffer at ±100 mA/cm$^2$.

Example 14

Figure 22:
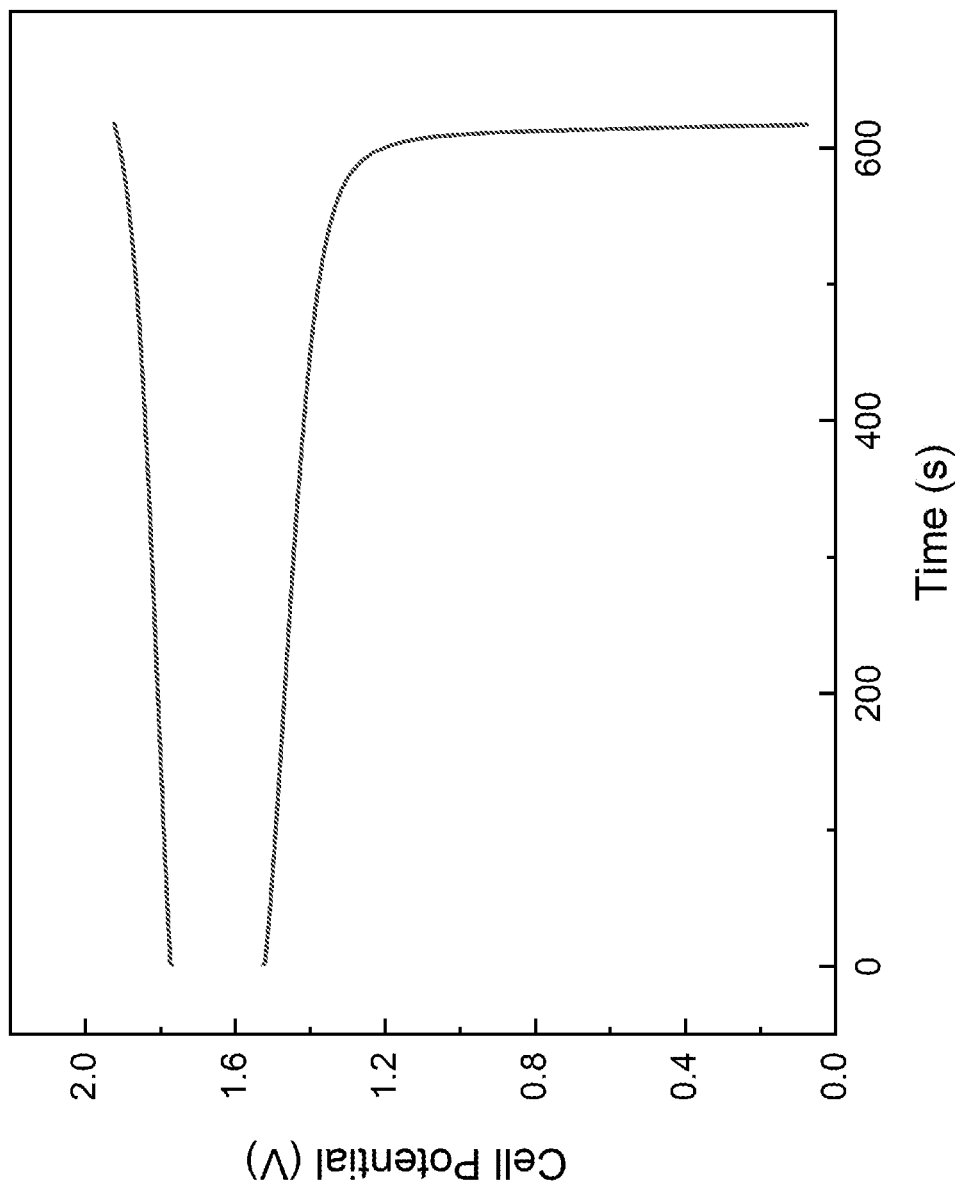
FIG. 22 illustrates a single 0.4 M CrPDTA vs Fe(CN)$_6$ flow battery cycle to 80% SOC in PDTA and NTA buffer at ±100 mA/cm$^2$.

To the negative electrolyte from example 16, 1 mL of 1.0 M NTA solution at pH 9 was added. When continuing to utilize the negative electrolyte described in example 16, the resulting flow battery, when operated utilizing 80% of the total electrolyte capacity at a current density of ±100 mA/cm$^2$, had a coulombic efficiency of 99.8% and energy efficiency of 79.0%. FIG. 22 illustrates a single 0.4 M CrPDTA vs Fe(CN)$_6$ flow battery cycle to 80% SOC in PDTA and NTA buffer at ±100 mA/cm$^2$.

Example 15

Figure 23:
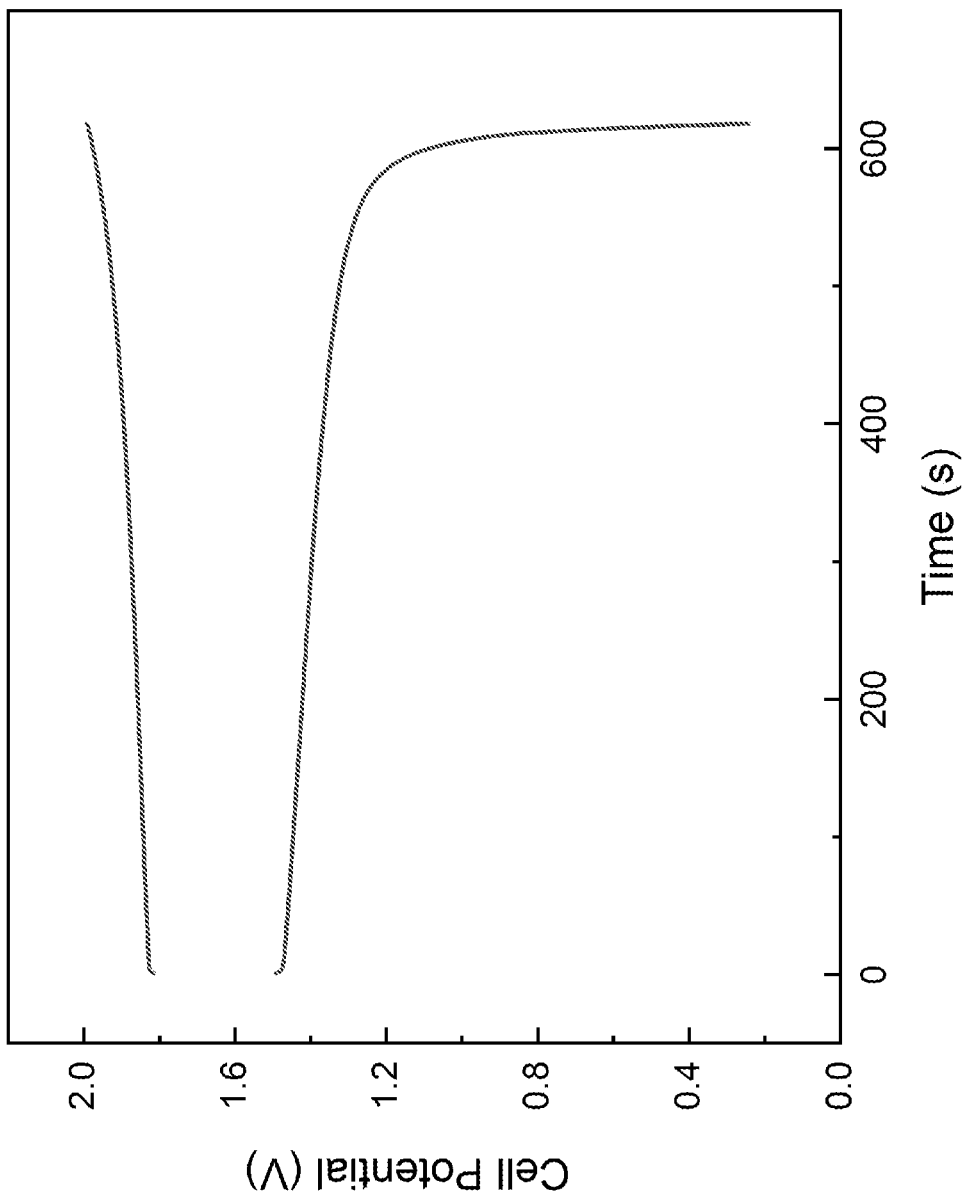
FIG. 23 illustrates a single 0.4 M CrPDTA vs Fe(CN)$_6$ flow battery cycle to 80% SOC in $K_2HPO_4$ buffer at ±100 mA/cm$^2$.

A negative electrolyte containing the KCrPDTA redox system as the active material for the negative electrode was prepared as in example 16, but with 0.2M K$_2$HPO$_4$ solid added as the buffer. The pH of the resulting solution was 7.85. A positive electrolyte containing the same system as used in example 10 was prepared. The resulting flow battery, assembled as described in example 9, when operated utilizing 80% of the total electrolyte capacity at a current density of ±100 mA/cm$^2$ had a coulombic efficiency of 100.0% and energy efficiency of 74.4%. FIG. 23 illustrates a single 0.4 M CrPDTA vs Fe(CN)$_6$ flow battery cycle to 80% SOC in K$_2$HPO$_4$ buffer at ±100 mA/cm$^2$.

Example 16

Figure 24:
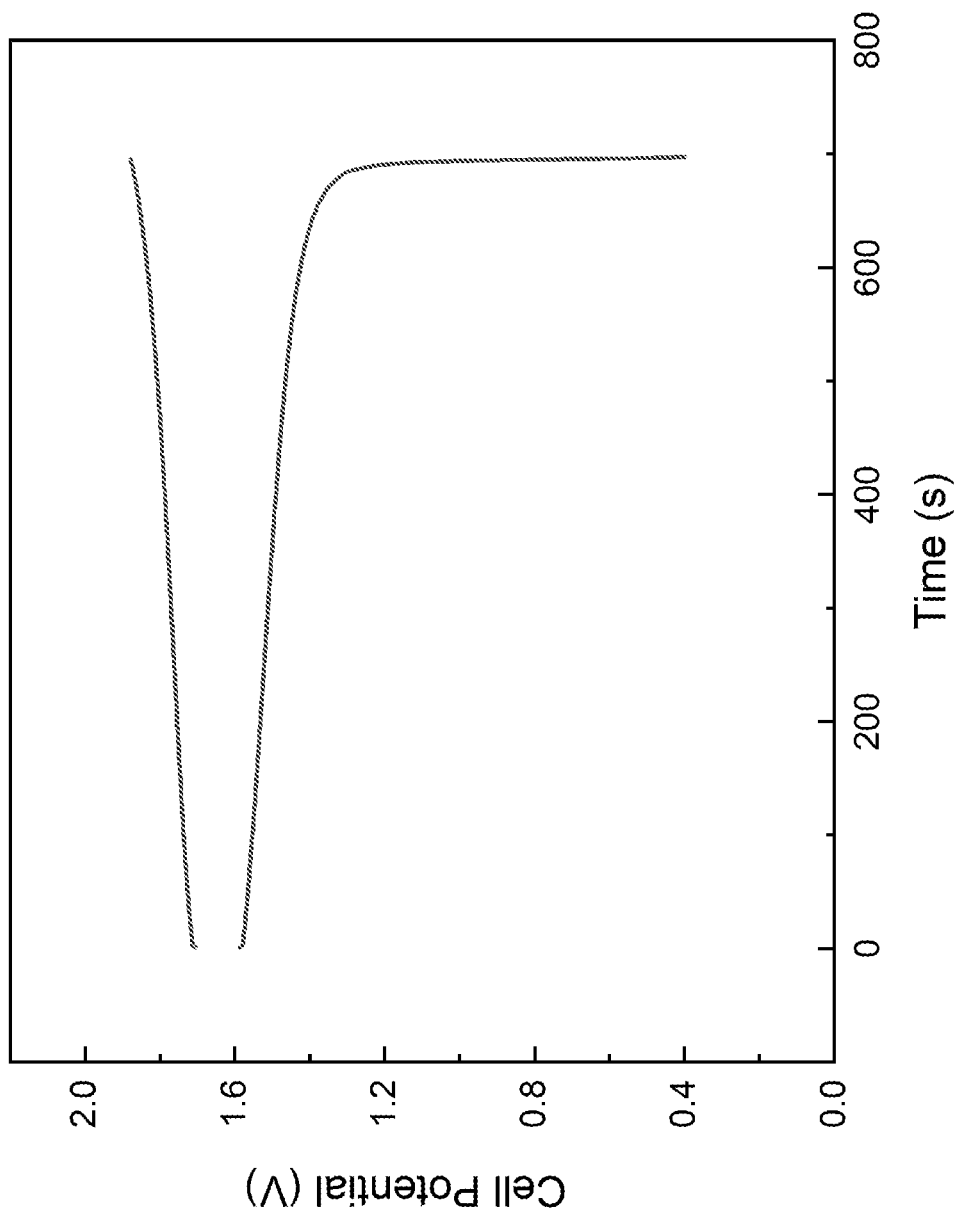
FIG. 24 illustrates a single 0.4 M CrPDTA vs Fe(CN)$_6$ flow battery cycle to 90% SOC in $K_2B_4O_7$ buffer with Bi plated carbon paper at ±100 mA/cm$^2$.

A negative electrolyte containing the KCrPDTA redox system as the active material for the negative electrode was prepared as in example 16, but with 0.2M K$_2$B$_4$O$_7$ solid added as the buffer. The resulting solution pH was 9.31. A positive electrolyte containing the same system as used in example 10 was prepared. Prior to cycling, the carbon paper electrodes on the chromium side were plated with bismuth utilizing a BiEDTA complex. The resulting flow battery, assembled as described in example 9, when operated utilizing 90% of the total electrolyte capacity at a current density of ±100 mA/cm$^2$ had a coulombic efficiency of 100.0% and energy efficiency of 84.7%. FIG. 24 illustrates a single 0.4 M CrPDTA vs Fe(CN)$_6$ flow battery cycle to 90% SOC in K$_2$B$_4$O$_7$ buffer with Bi plated carbon paper at ±100 mA/cm$^2$.

Example 17

Figure 25:
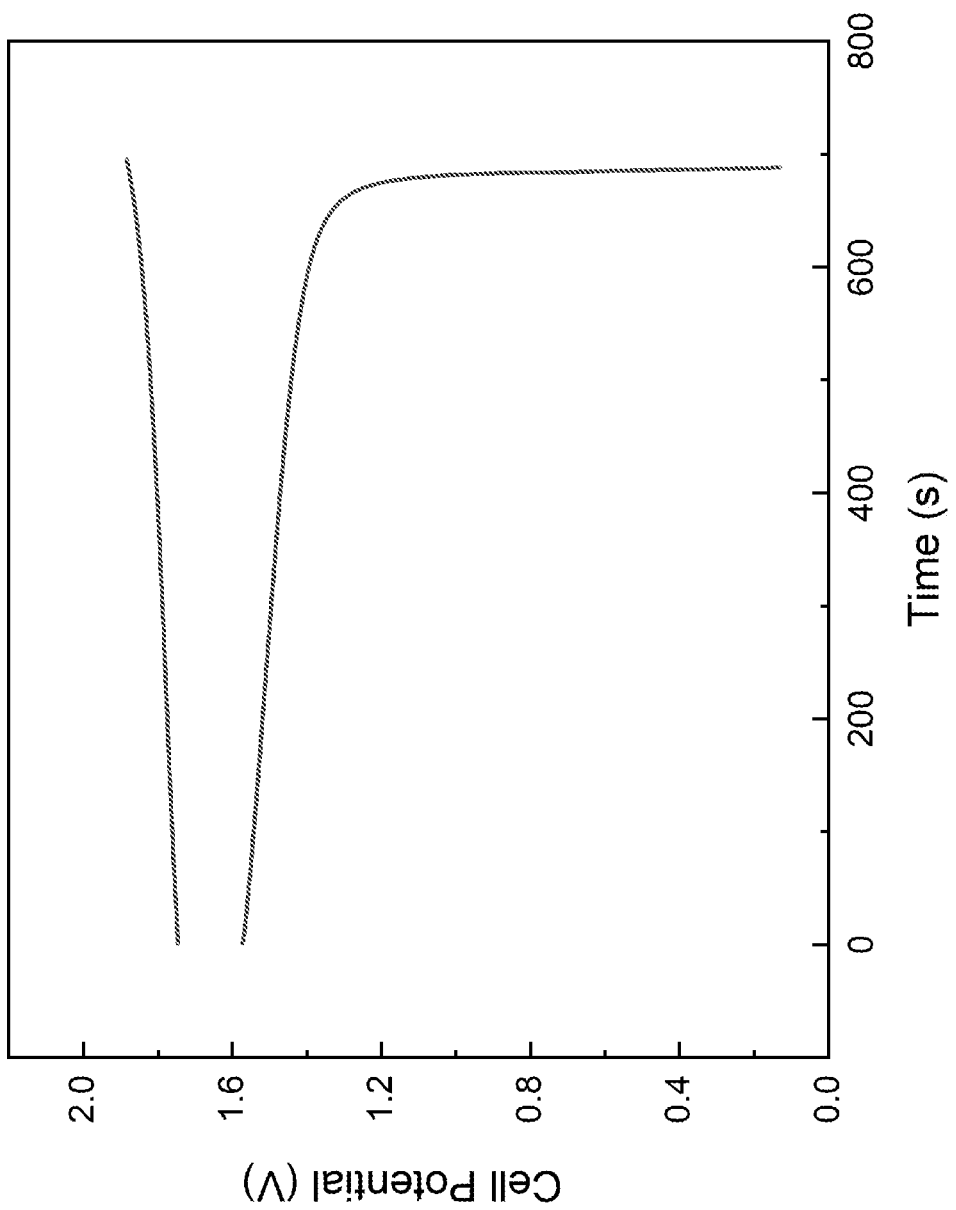
FIG. 25 illustrates a single 0.4 M CrPDTA vs Fe(CN)$_6$ flow battery cycle to 90% SOC in $K_2B_4O_7$ buffer with carbon cloth electrodes at ±100 mA/cm$^2$.

A negative electrolyte containing the KCrPDTA redox system as the active material for the negative electrode was prepared as in example 19. The resulting solution pH was 9.31. A positive electrolyte containing the same system as used in example 10 was prepared. The resulting flow battery was assembled as described in example 9, with the exception of the 5 carbon paper electrodes on each side being replaced with 4 of the same size ELAT hydrophobic carbon cloth electrodes, that were untreated. This resulted in 37.4% compression. The resulting flow battery, when operated utilizing 90% of the total electrolyte capacity at a current density of ±100 mA/cm$^2$, had a coulombic efficiency of 99.0% and energy efficiency of 82.0%. FIG. 25 illustrates a single 0.4 M CrPDTA vs Fe(CN)$_6$ flow battery cycle to 90% SOC in K$_2$B$_4$O$_7$ buffer with carbon cloth electrodes at ±100 mA/cm$^2$.

Example 18

Figure 26:
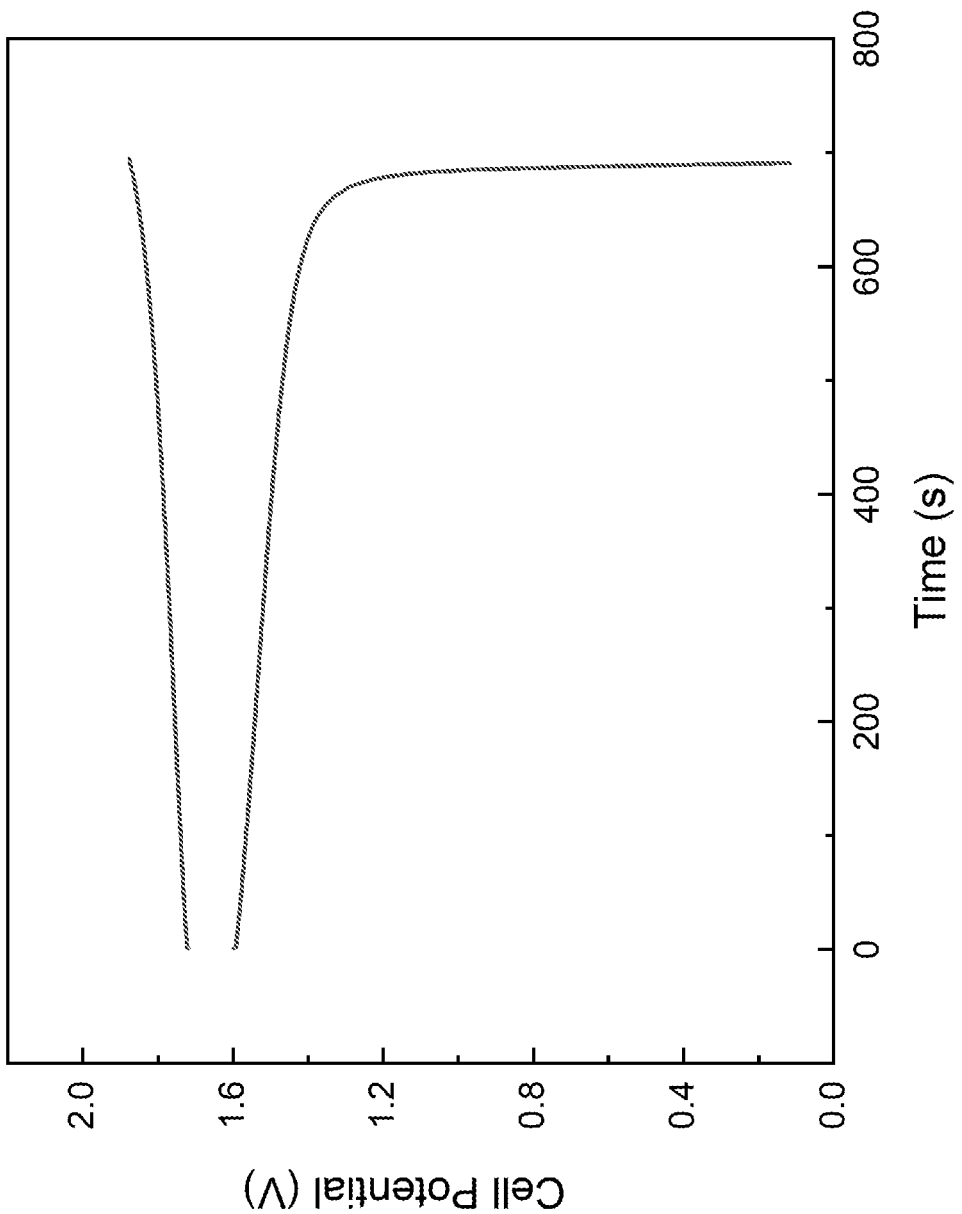
FIG. 26 illustrates a single 0.4 M CrPDTA vs Fe(CN)$_6$ flow battery cycle to 90% SOC in $K_2B_4O_7$ buffer with Nafion 211 paper at ±100 mA/cm$^2$.

A negative electrolyte containing the KCrPDTA redox system as the active material for the negative electrode was prepared as in example 19. The resulting solution pH was 9.31. A positive electrolyte containing the same system as used in example 10 was prepared. The resulting flow battery was assembled as described in example 9, with the exception of the Nafion 212 membrane being replaced with a Nafion 211 membrane with the same treatment, the 0.002" PTFE sheet being replaced with a 0.001" PTFE sheet, and the 5 carbon paper electrodes being replaced by 4 carbon paper electrodes with the same treatment. This results in a compression of 9.3%. The resulting flow battery, when operated utilizing 90% of the total electrolyte capacity at a current density of ±100 mA/cm$^2$, had a coulombic efficiency of 99.4% and energy efficiency of 84.5%. FIG. 26 illustrates a single 0.4 M CrPDTA vs Fe(CN)$_6$ flow battery cycle to 90% SOC in K$_2$B$_4$O$_7$ buffer with Nafion 211 paper at ±100 mA/cm$^2$.

Example 19

Figure 27:
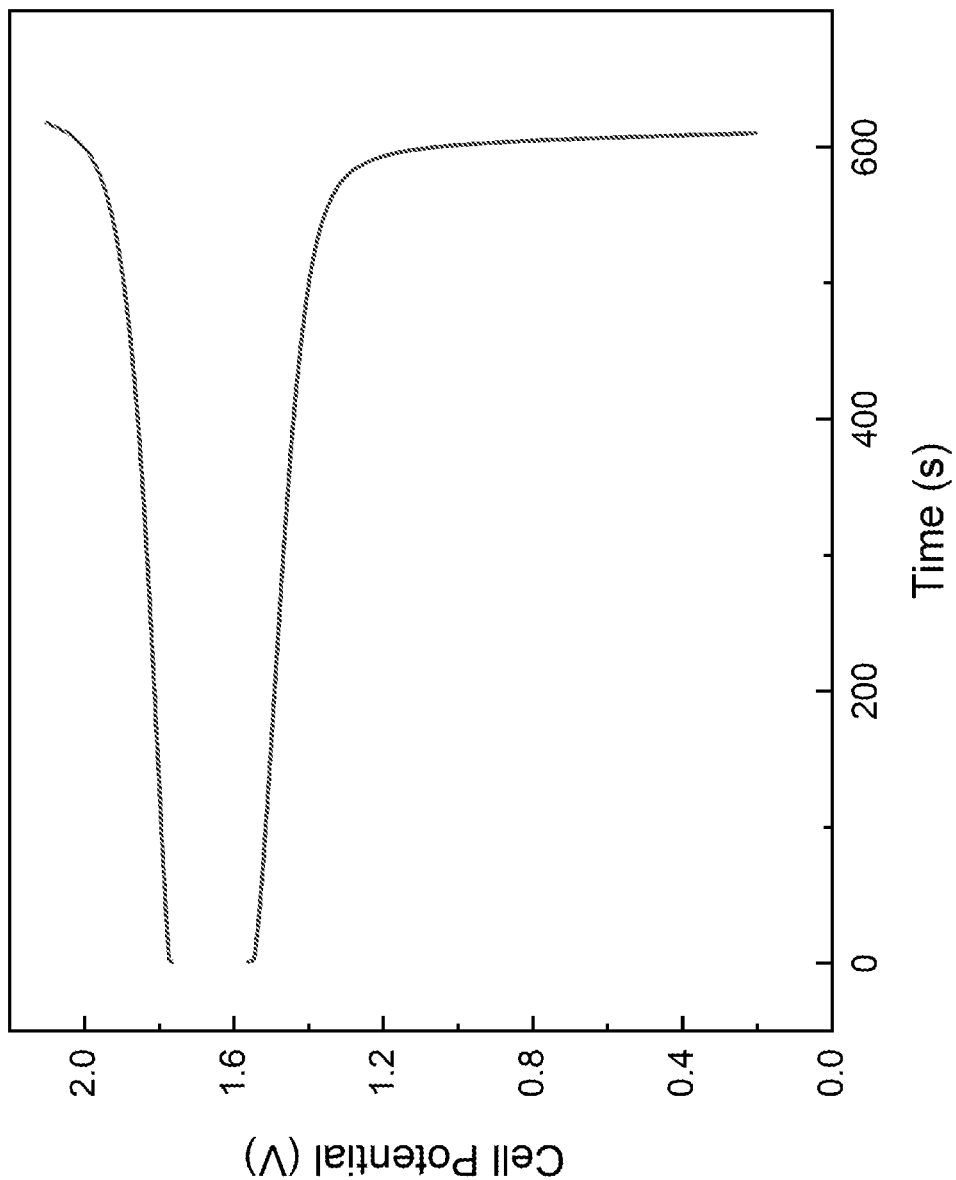
FIG. 27 illustrates a single 0.4 M CrPDTA vs Fe(CN)$_6$ flow battery cycle to 80% SOC in $K_2B_4O_7$ buffer with Fumapem F-930 RFS membrane at ±100 mA/cm$^2$.

A negative electrolyte containing the KCrPDTA redox system as the active material for the negative electrode was prepared as in example 19. The resulting solution pH was 9.31. A positive electrolyte containing the same system as used in example 10 was prepared. The resulting flow battery was assembled as described in example 9, with the exception of the Nafion 212 membrane being replaced with a Fumapem F-930 RFS membrane with no treatment, and the 0.002" PTFE sheet being replaced with a 0.001" PTFE sheet. The resulting flow battery, when operated utilizing 80% of the total electrolyte capacity at a current density of ±100 mA/cm$^2$, had a coulombic efficiency of 98.7% and energy efficiency of 78.9%. FIG. 27 illustrates a single 0.4 M CrPDTA vs Fe(CN)$_6$ flow battery cycle to 80% SOC in K$_2$B$_4$O$_7$ buffer with Fumapem F-930 RFS membrane at ±100 mA/cm$^2$.

Example 20

A negative electrolyte containing the KCrPDTA redox system as the active material for the negative electrode was prepared as in example 19. The resulting solution pH was 9.31. A positive electrolyte containing the same system as used in example 10 was prepared. The system was charged to 90% SOC at a current density of 100 mA/cm$^2$, followed by a 20 mA/cm$^2$ charge until visible H$_2$ generation was observed. The resulting charged chromium solution was transferred to a sealed flask to which the headspace was filled with CO$_2$. The resulting mixture was allowed to stand for 7 days, after which a gas chromatography sample was taking utilizing a hayesep-d column. Both CO and CH$_4$ products were observed when compared to reference gas samples containing CO and CH$_4$.

Example 21

A negative electrolyte containing the KCrPDTA redox system as the active material for the negative electrode was prepared as in example 19. The resulting solution pH was 9.31. A positive electrolyte containing the same system as used in example 10 was prepared. The system was charged to 90% SOC at a current density of 100 mA/cm$^2$, followed by a 20 mA/cm$^2$ charge until visible H$_2$ generation was observed. The resulting charged chromium solution was transferred to a sealed flask containing CuCl$_2$ solids, and to which the headspace was filled with CO$_2$. The resulting mixture was allowed to stand for 7 days, after which a gas chromatography sample was taking utilizing a hayesep-d column. Both CO and CH$_4$ products were observed when compared to reference gas samples containing CO and CH$_4$.

Example 22

Figure 28:
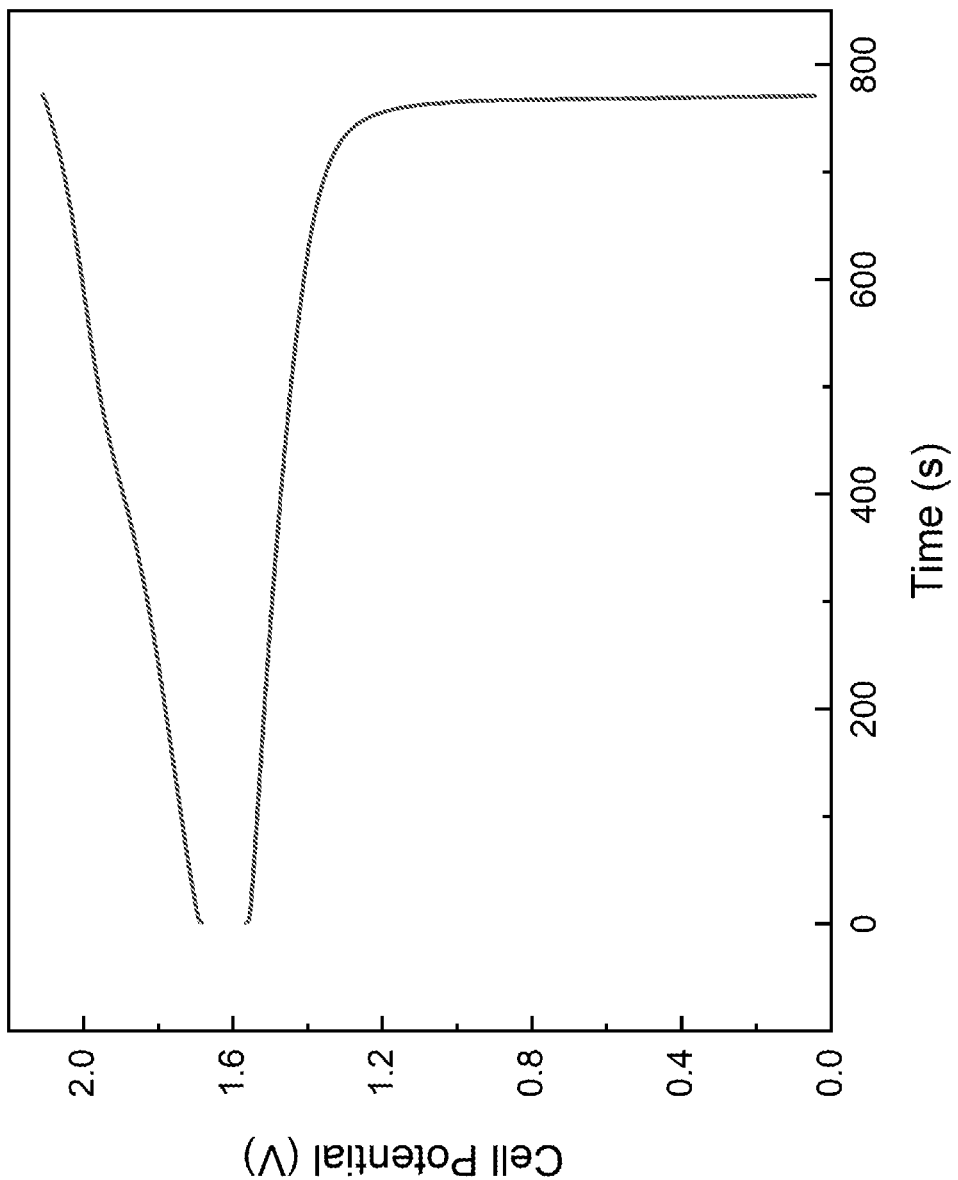
FIG. 28 illustrates a single 0.5 M CrEDTA vs Fe(CN)$_6$ flow battery cycle to 80% SOC in $Na_2B_4O_7$ buffer at ±100 mA/cm$^2$.

A negative electrolyte containing the NaCrEDTA redox system as the active material for the negative electrode was prepared as described in example 6 with the exception of NaOH rather than KOH. Na$_2$B$_4$O$_7$ was added to a concentration of 0.1 M and the concentration of the CrEDTA was 0.5 M. The pH of the solution was adjusted to pH 9.0 with NaOH. A negative electrolyte containing the same system as used in example 10 was prepared. The resulting flow battery, assembled as described in example 9, when operated utilizing 80% of the total electrolyte capacity at a current density of ±100 mA/cm$^2$ had a coulombic efficiency of 99.9% and energy efficiency of 78.3%. FIG. 28 illustrates a single 0.5 M CrEDTA vs Fe(CN)$_6$ flow battery cycle to 80% SOC in Na$_2$B$_4$O$_7$ buffer at ±100 mA/cm$^2$.

Example 23

A saturated solution of KCrPDTA was prepared by dissolving KCrPDTA crystals in minimal DI water at room temperature such that crystals remain undissolved. The solution was agitated for 1 day. The solution was diluted by a factor of 201× into DI water and then analyzed using UV-Vis at 506 nm (116 M$^{-1}$L$^{-1}$=ε). A maximum solubility was found to be 1.32 M. Table 8 illustrates the solubility of metal ligand complexes with different cations. For the Na$^+$ cation with CrEDTA, the solubility was determined from a concentrated impure solution containing 3:1 NaCl. The concentration was limited by increased viscosity. For the K$_2$ with Fe-DTPA, the solubility was determined from a concentrated impure solution containing 3:1 KCl. The concentration was limited by increased viscosity. All values in Table 8 are approximate.

TABLE 8

| Material | Cation | Max Solubility at RT [M] |
| --- | --- | --- |
| CrPDTA | Li | 0.78 |
|  | Na | 0.17 |
|  | K | 1.32 |
|  | NH$_4$ | 0.92 |
| CrEDTA | Na | 1.09 < pH 7.5, 1.32 pH > 7.5 |
|  | K | 0.22 < pH 7.5 |
| FeDTPA | K$_2$ | 1.35 |

Example 24

A mass of 1.078 g (0.0025 mol) NaCrPDTA (max solubility=0.17 M) and 1.038 g (0.0025 mol) KCrEDTA (max solubility=0.22 M). DI H$_2$O was added up to a final volume of 6 mL. The solution was stirred for 1 day at room temperature, at which time no solids remained. The solution contained 0.42 M of each electrolyte with a total chromium concentration of 0.84 M. See Table 8.

Example 25

Figure 29:
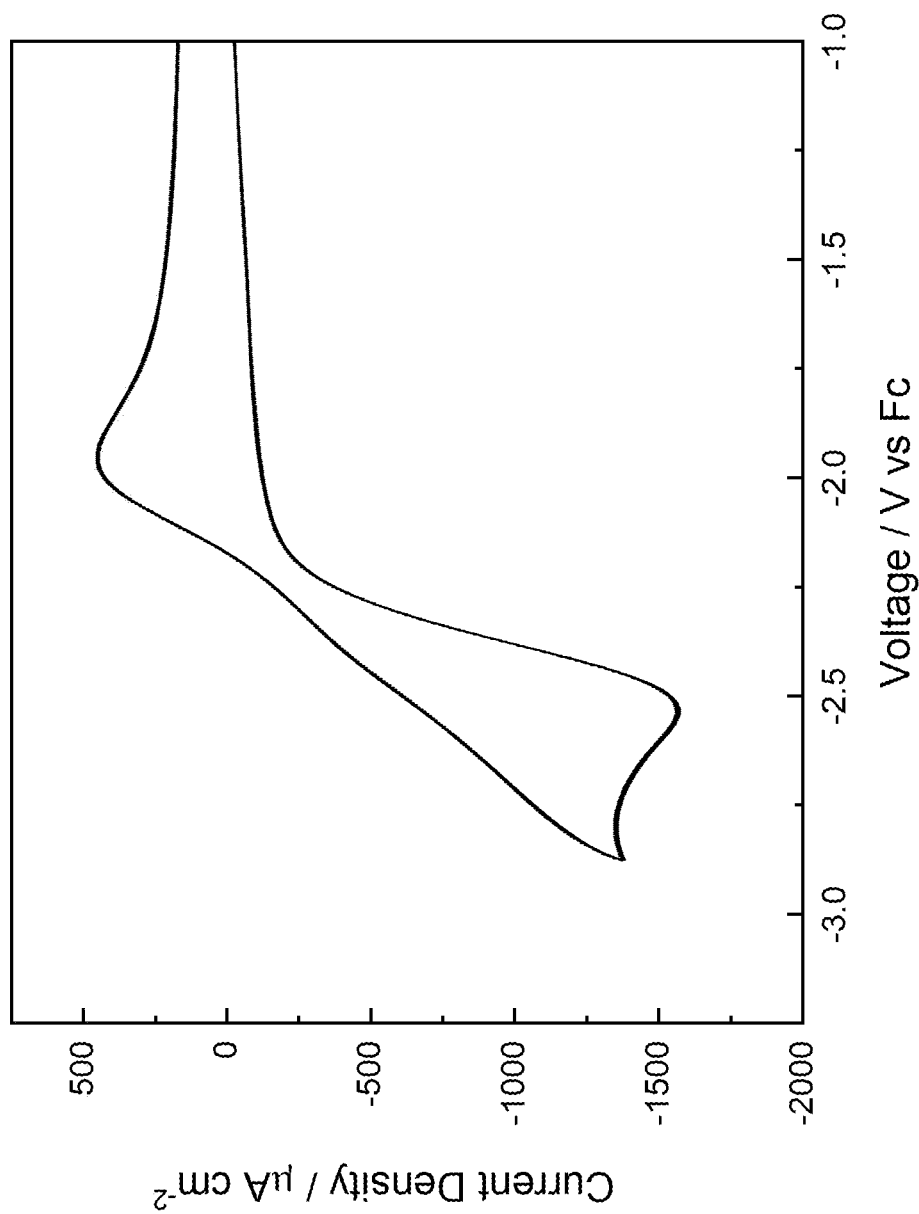
FIG. 29: illustrates cyclic voltammetry taken at 100 mV s$^{-1}$ of 10 mM TBACrPDTA in acetonitrile with 0.1 M TBAPF$_6$ on a glassy carbon working electrode.
Figure 30:
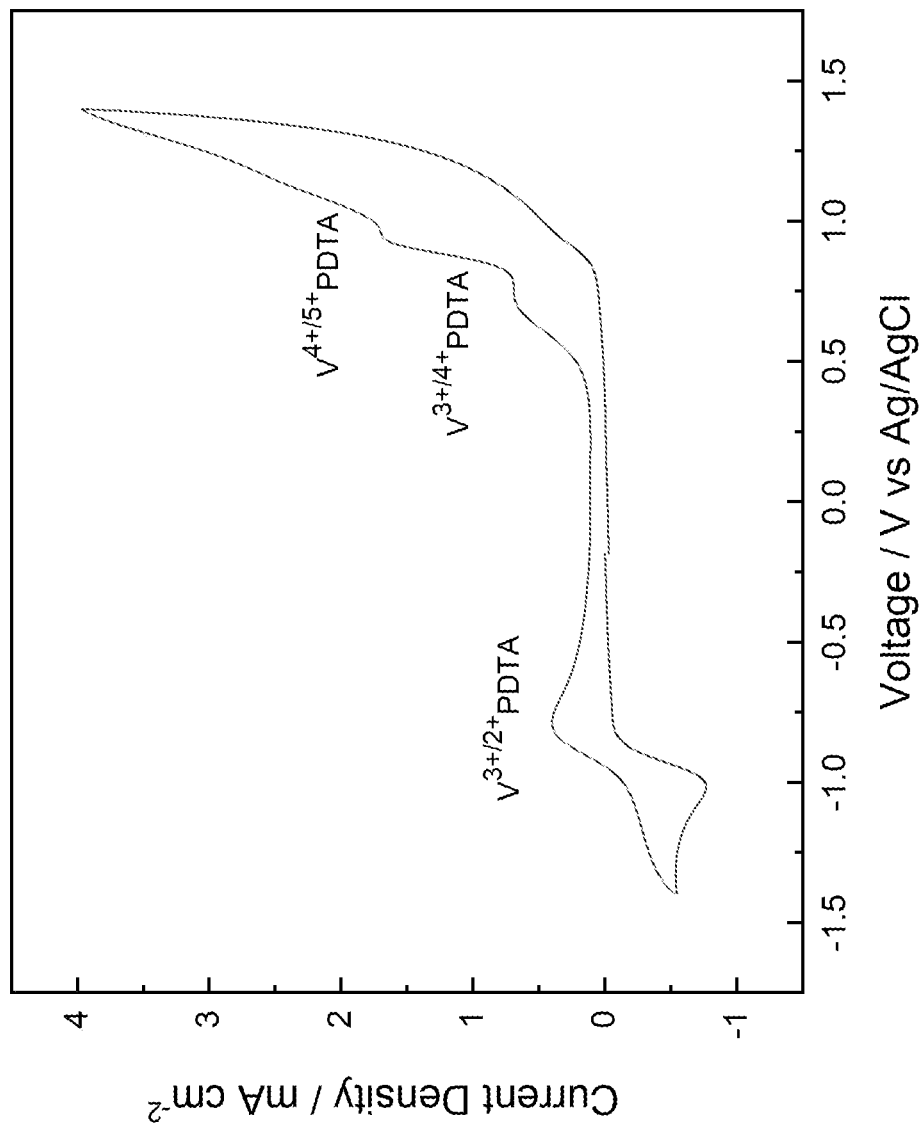
FIG. 30 illustrates cyclic voltammetry taken at 100 mV s$^{-1}$ of K[VPDTA] in 1 M potassium borate at pH 8 on a glassy carbon working electrode.

A 0.010 M solution of tetrabutylammonium (TBA) CrPDTA was prepared in acetonitrile. Tetrabutylammonium hexafluorophosphate (TBAPF$_6$) was added to a concentration of 0.1 M. Cyclic voltammetry was conducted on the solution using a glassy carbon working electrode, Ag/AgCl reference electrode, and platinum wire reference electrode. Scans were performed at 100 mV s$^{-1}$. Ferrocene was added to the solution as an internal reference of ferrocene/ferrocenium. Solutions were prepared similarly in ortho-difluorobenzene as well as tetrahydrofuran. The highly reducing potential is shown to be reversible in non-aqueous environments. See Table 8. FIG. 29 illustrates cyclic voltammetry taken at 100 mV s$^{-1}$ of 10 mM TBACrPDTA in ACN with 0.1 M TBAPF$_6$ on a glassy carbon working electrode.

Example 26

To N$_2$ sparged DI water (20 mL), vanadium sulphate (V$_2$(SO$_4$)$_3$) (1.950 g, 5 mmol) was added and heated at 80° C. in the presence of H$_4$PDTA (1.53 g, 5 mmol). KOH (1.120 g, 20 mmol) was added with a flow of positive nitrogen. The solution was stirred at 80° C. for 16 hours, at which time the solution was a dark red color. The final pH was adjusted to pH 6 with KOH. Cyclic voltammetry was performed at pH 9 in 1 M borate solution on a glassy carbon electrode with a Ag/AgCl reference and platinum wire working electrode. With an oxidation of V$^{4+/5+}$ present around 1 V vs. Ag/AgCl, a flow battery of CrPDTA and VPDTA at pH 9 will yield a cell potential around 2.3 V. FIG.

30 illustrates cyclic voltammetry taken at 100 mV s$^{-1}$ of K[VPDTA] in 1 M potassium borate at pH 8 on a glassy carbon working electrode. Similar vanadium compounds of VDTPA, VEDTA, and VBDTA have shown to be viable positive electrolytes.

Example 27

Figure 31:
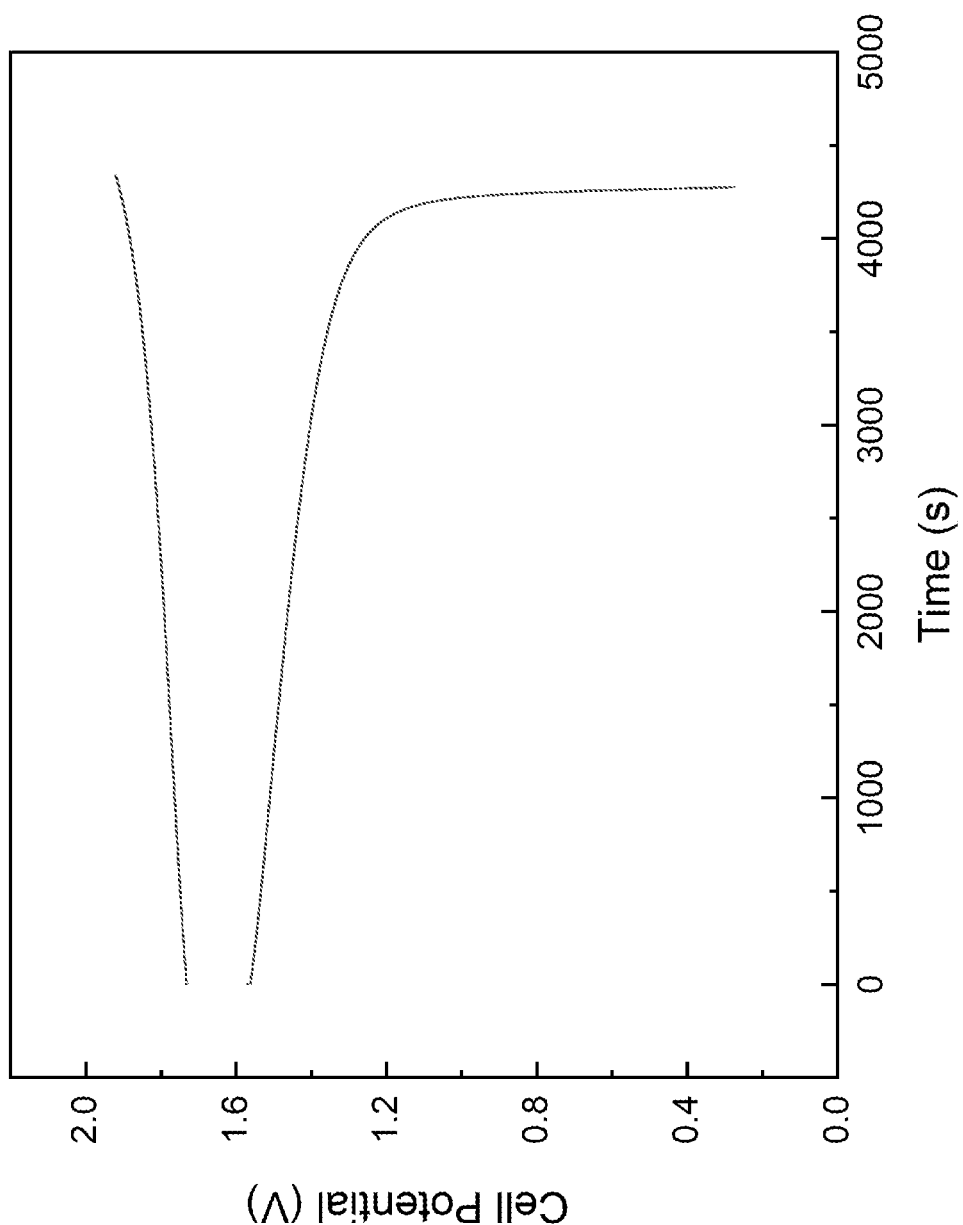
FIG. 31 illustrates a single 1.0 M CrPDTA vs Fe(CN)$_6$ flow battery cycle to 75% SOC in $K_2B_4O_7$ buffer at ±100 mA/cm$^2$.

A negative electrolyte containing CrPDTA as an active material for the negative electrode was prepared as described in example 1 with the exception that a 1:1 ligand to metal ratio was used during synthesis. The concentration of the CrPDTA was 1.0 M. $K_2B_4O_7$ was added to a concentration of 0.1 M and the final pH was 9.5. A positive electrolyte containing a $K_4Fe(CN)_6$ and $K_3Fe(CN)_6$ redox system was prepared in volumetric excess. With the addition of $K_2B_4O_7$, the pH was adjusted to 9.5 with 0.1 M $K_3Fe(CN)_6$, 0.5 M $K_4Fe(CN)_6$, and 0.025 M $K_2B_4O_7$. Both solutions were at ambient temperature. The resulting flow battery, assembled as described in example 9 with the exception of the CrPDTA solution having a volume of 30 mL instead of 10 mL, when operated utilizing 75% of the total electrolyte capacity at a current density of ±100 mA/cm$^2$ had a coulombic efficiency of 98.5% and energy efficiency of 79.8%. FIG. 31 illustrates a single 1.0 M CrPDTA vs $Fe(CN)_6$ flow battery cycle to 75% SOC in $K_2B_4O_7$ buffer at ±100 mA/cm$^2$.

Example 28

The iron-chromium (FeCr) RFB was among the first flow batteries to be investigated due to the low cost of the electrolyte and the 1.2 volt cell potential. The effects of chelation on the solubility and electrochemical properties of the $Fe^{3+/2+}$ redox couple. An Fe electrolyte utilizing DTPA exhibits efficient and high-performance flow battery cycling at a pH of 9 versus a Cr-chelate complex utilizing PDTA. The FeDTPA electrolyte can be cycled at concentrations up to 1.35 M, equating to a storage capacity of 36.2 Ah L$^{-1}$, with near-quantitative efficiency. When paired with a CrPDTA electrolyte, the equilibrium cell potential of the all-chelated FeCr RBF is 1.18 V with a maximum discharge power of 216 mW cm$^{-2}$. Key aspects of the coordination chemistry of FeDTPA are compared with CrPDTA and highlight the importance of molecular-level understanding for driving flow battery system performance.

Chelating agents, such as EDTA, are commonly used to solubilize and stabilize metal ions for a variety of applications including agricultural fertilizer, medicine, and consumer food and health products. The aminopolycarboxylate (APC) class of chelates, including EDTA, typically bind metal ions in 6 locations, with 2 nitrogen atoms and 4 carboxylate arms surrounding the metal ion in a pseudo-octahedral geometry. The strong coordination behavior and improved solubility at neutral pH, coupled with their environmentally benign nature and industrial scale production, make APC chelate complexes attractive electrolytes for flow battery applications.

Chelation influences electrochemical properties of metal ions including the electron transfer kinetics and the redox potential, which can lead to improvements in flow battery performance. The entropic reorganization energy of the solvent associated with a change in metal oxidation state, described by Marcus-Hush theory, is strongly influenced by chelation. The chelated complex creates a pseudo-rigid structure which will not undergo a large change in radius or solvent interaction, thus reducing the activation energy of electron transfer. This effect is observed by comparing the energy of entropic rearrangement for $Fe(OH2)_6^{3+/2+}$ (43 cal K-1mol-1) with $Fe(bpy)_3^{3+/2+}$ (bpy=2,2'-bipyridine) (2 cal K-1mol-1), which corresponds to an increase in the heterogeneous reduction rate constant from 10$^{-3}$ to 10$^{-2}$ cm s$^{-1}$ on a graphite electrode.

Chelates also affect the thermodynamics of the redox reaction, leading to a range of reduction potentials that can be obtained through ligand selection. This allows a metal to be explored as both a positive electrolyte (posolyte) and negative electrolyte (negolyte) for use in RFBs with the added benefit of typically improved redox kinetics. For example, the reduction potential of $Fe^{3+/2+}$ in an aqueous environment $Fe(OH_2)_6^{3+/2+}$ is +0.573 V vs. Ag/AgCl, but the reduction potential of $Fe^{3+/2+}$ has been shown to be as negative as −0.953 V vs. Ag/AgCl when Fe is chelated to triethanolamine ([FeTEA]$^{3+}$), or as positive as +0.903 V vs. Ag/AgCl when Fe is chelated to bpy, [Fe(bpy)$_3$]$^{2+}$.

FeCr RFBs were among the first RFBs investigated due to the low materials cost. Early FeCr RFB systems typically operated at a concentration of 1 M Fe and Cr in HCl at room temperature and provided voltages up to 1.18 V.11 Slow redox kinetics of $Cr^{3+/2+}$ resulted in low current density (21.5 mA cm$^{-2}$) and lowered efficiencies due to H$_2$ generation, leading to poor system performance.

In contrast with the $Fe^{3+/2+}$ posolyte used in the FeCr RFB, Fe chelates are primarily used as negolytes because highly oxidizing Fe complexes tend to be unstable. An example of an Fe complex used as a negolyte is [FeTEA]$^{3+/2+}$ which was paired with a $Br_2/Br^-$ posolyte to yield an RFB with a cell potential of 1.98 V. Other Fe-based complexes utilizing chelates such as EDTA, citrate, and oxalate have also been investigated as negolytes because of their redox potentials around 0 V vs. Ag/AgCl at pH 6. When paired with a $Br_2/Br^-$ posolyte, they yield cell potentials around 1 V. FeDTPA was also considered as a negolyte to be paired with $Br_2/Br^-$ in the above experiment, however, it was not sufficiently soluble in acidic conditions (<0.4 M).

It has been demonstrated that a Cr-complex utilizing PDTA, an APC related to EDTA, was able to stabilize the $Cr^{3+/2+}$ redox couple at near neutral pH of 9 with an E° at −1.392 V vs. Ag/AgCl. CrPDTA, when paired with $Fe(CN)_6^{3-/4-}$ in an RFB, was demonstrated to inhibit the production of H$_2$ at a working pH of 9-10 and exhibit high performance (515 mW cm-1) without an electrocatalyst. However, the low solubility and redox potential of $Fe(CN)_6^{3-/4-}$ at 0.3 V vs Ag/AgCl leaves room for significant improvement of the posolyte. Seeking to pair the chelated chromium with a chelated iron, we report an FeCr battery where both Fe and Cr ions are chelated to APCs.

Figure 41A:
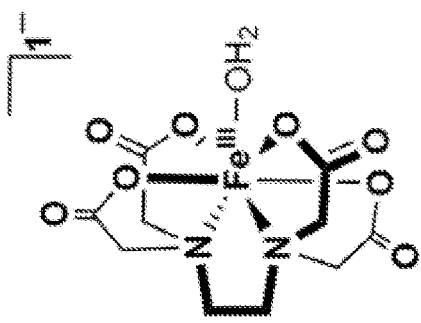
FIG. 41A illustrates a 7-coordinate, pentagonal bipyramidal molecular geometry present in Fe$^{3+}$ APC species [FeEDTA]$^{1-}$ at pH 7 based on crystallographic data.
Figure 41B:
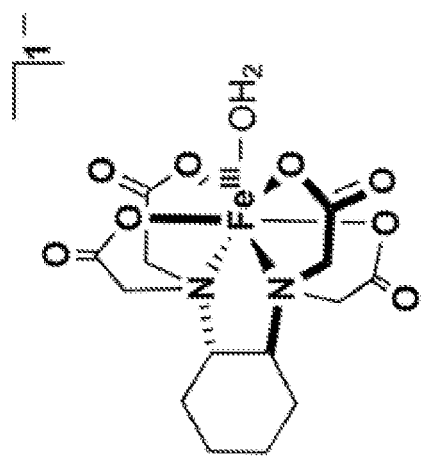
FIG. 41B illustrates a 7-coordinate, pentagonal bipyramidal molecular geometry present in Fe$^{3+}$ APC species [FeCyDTA]$^{1-}$ at pH 7 based on crystallographic data.
Figure 41C:
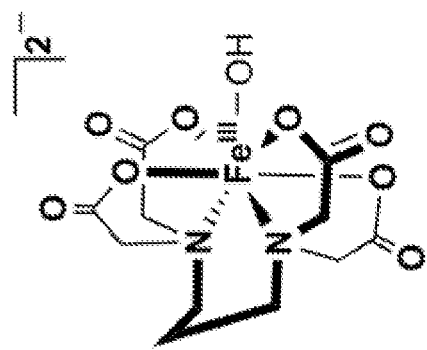
FIG. 41C illustrates a 7-coordinate, pentagonal bipyramidal molecular geometry present in Fe$^{3+}$ APC species [FePDTA]$^{2-}$ at pH 7.5 based on titration data.
Figure 41D:
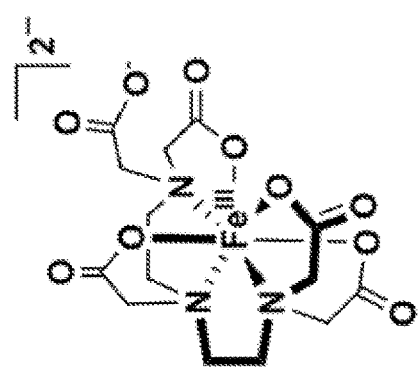
FIG. 41D illustrates a 7-coordinate, pentagonal bipyramidal molecular geometry present in Fe$^{3+}$ APC species [FeDTPA]$^{2-}$ at pH 9 based on crystallographic data.
Figure 42A:
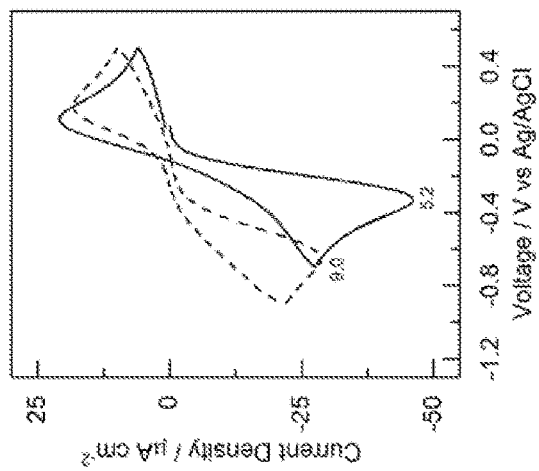
FIG. 42A illustrates the CV of Fe chelate complexes at pH 5.2 and 9.0 for 10 mM NaFeEDTA.
Figure 42B:
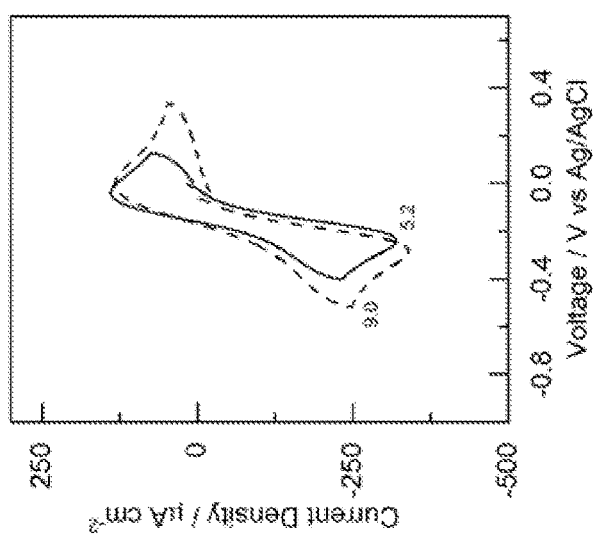
FIG. 42B illustrates the CV of Fe chelate complexes at pH 5.2 and 9.0 for 10 mM $K_2$FeDTPA.

Different APC chelates were explored as possible Fe-based posolytes for their high coordination number, binding strength, environmental benign nature, and low cost. FePDTA was initially considered for its positive reduction potential of +0.070 V vs. Ag/AgCl and its potential use in a same-chelate RFB with CrPDTA. The hexadentate coordination of PDTA excludes water from coordination, however, mildly alkaline conditions result in the coordination of hydroxide in a 7-coordinate geometry, [Fe(PDTA)OH]$^{2-}$, which destabilizes the chelate complex and causes the precipitation of Fe(OH)$_3$. FIG. 41A-D illustrates the 7-coordinate, pentagonal bipyramidal molecular geometry present in Fe$^{3+}$ APC species. The pentagonal plane motif is in bold. FIG. 41A illustrates the [FeEDTA]$^{1-}$ at pH 7 based on crystallographic data. FIG. 41B illustrates the [FeCyDTA]$^{1-}$ at pH 7 based on crystallographic data. FIG. 41C illustrates the [FePDTA]$^{2-}$ at pH 7.5 based on titration data. FIG. 41D illustrates the [FeDTPA]$^{2-}$ at pH 9 based on crystallographic data. The ability of chelates to stabilize the preferred 7-coordinate geometry of Fe can allow for increased solubility above a neutral pH. For example, the FeEDTA complex utilizes the 6-coordinate EDTA ligand, but space remains available in the coordination sphere for an additional water to coordinate to the metal for a total Fe coordination number of 7 with the formula [Fe(H$_2$O)EDTA]. FIG. 41A illustrates the [FeEDTA]$^{1-}$ at pH 7 based on crystallographic data. FeEDTA is not an ideal RFB electrolyte as it has a reduction potential pH dependence and due to the coordinated water, it forms a dimer species in mildly alkaline species which has decreased electrochemical reversibility and a more negative reduction potential (FIGS. 42A-B illustrates the CV of Fe chelate complexes at pH 5.2 and 9.0. FIG. 42A illustrates 10 mM NaFeEDTA). Other APCs such as CyDTA and HEDTA were not further examined for use with iron due to their coordination of water and dimerization in alkaline solutions, similar to that of FeEDTA. FIG. 41B illustrates the [FeCyDTA]$^{1-}$ at pH 7 based on crystallographic data. Similar to that of FePDTA, when complexed with iminodiacetic acid, Fe(IDA)$_2$ formed insoluble precipitates at the required pH of 9. The Fe(bpy)$_3^{2+}$ complex was also examined, however, it was found the complex forms an insoluble precipitate upon oxidation. Table 9 provides for the stability and binding constants of iron-chelate complexes. All values in Table 9 are approximate.

TABLE 9

| Complex | Denticity (total) | Stability at pH 9 | Overall Fe coordination at pH 9 | Binding Constant (Fe$^{+2}$) | Binding Constant (Fe$^{+3}$) |
|---|---|---|---|---|---|
| FeEDTA | 6 | Dimerizes | 7 | 14.33 | 25.10 |
| FeHEDTA | 6 | Dimerizes | 7 | 12.2 | 19.7 |
| FeCyDTA | 6 | Dimerizes | 7 | 16.27 | 28.05 |
| Fe(IDA)$_2$ | 3 | Insoluble | NA | 5.80 | 10.42 |
| FePDTA | 6 | Insoluble | NA | 13.42 | 21.4 |
| Fe(bpy)$_3$ | 2 | Insoluble | NA | 4.2 | 16.29 |
| FeDTPA | 8 | Soluble | 7 | 16.55 | 28.60 |

Figure 43:
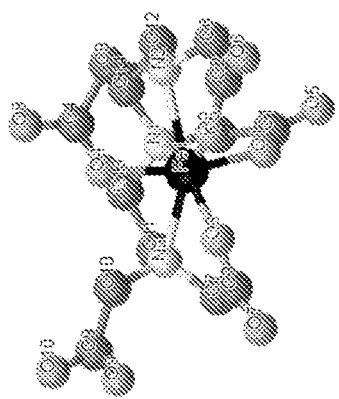
FIG. 43 illustrates a X-ray crystal structure of $K_2$[FeDTPA]·2.5H$_2$O.
Figure 44A:
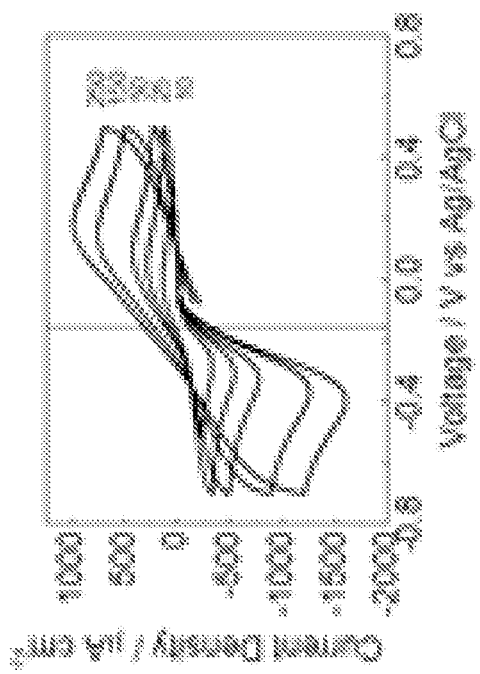
FIG. 44A illustrates a CV recorded at different scan rates of a solution containing 10 mM FeDTPA in 0.25 m KBi at pH 9 on a glassy carbon electrode. AgCl).
Figure 44B:
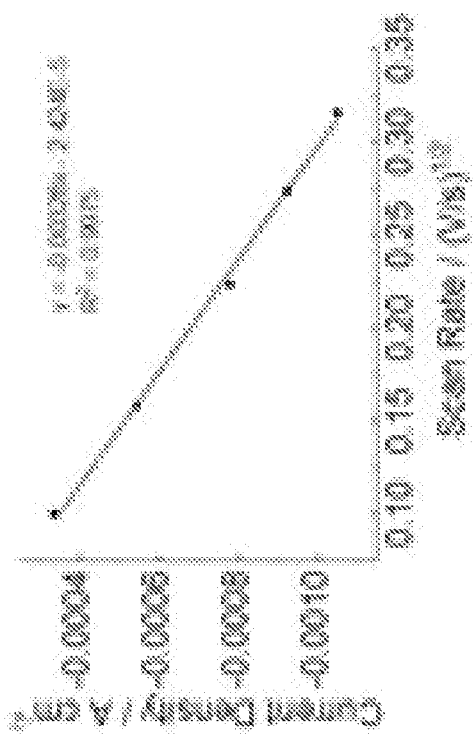
FIG. 44B illustrates the peak reduction current versus scan rate, $v^{1/2}$ for the different scan rates with a linear fit.
Figure 44C:
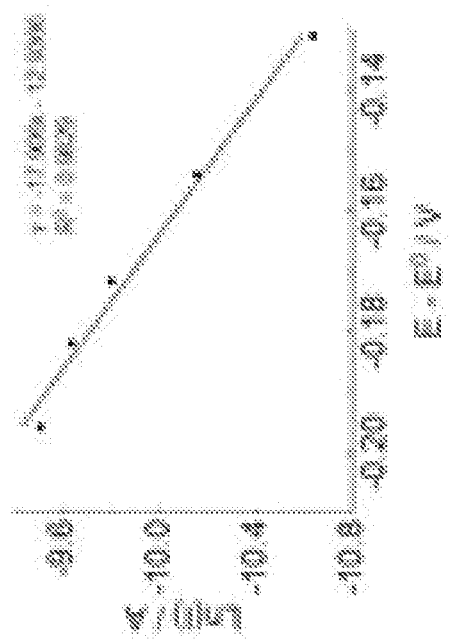
FIG. 44C illustrates the natural log of the peak reduction current ($i_{pc}$) versus the different in potential between the voltage at the peak reduction current ($E_{pc}$) and the calculated $E^0$ of the reduction with linear fit.
Figure 45A:
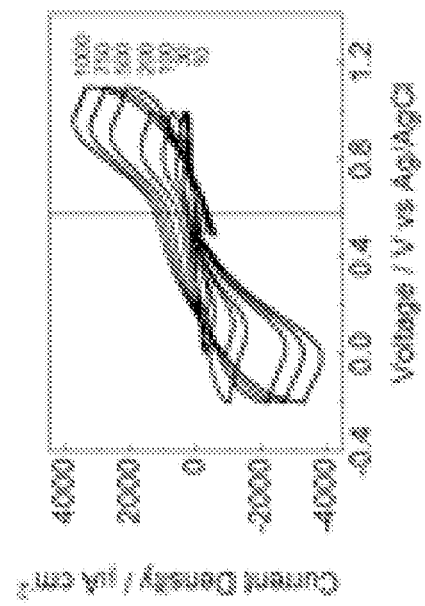
FIG. 45A illustrates a CV at different scan rates of a solution containing 10 mM $FeCl_3$ in 3 M HCl on a glassy carbon electrode. The vertical line represents the literature value of $E^0$ (0.55 V vs Ag/AgCl).
Figure 45B:
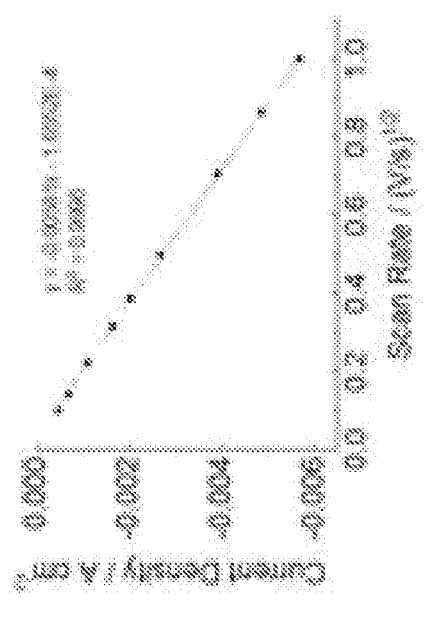
FIG. 45B illustrates the peak reduction current versus scan rate, $v'^{12}$ for the different scan rates with a linear fit.
Figure 45C:
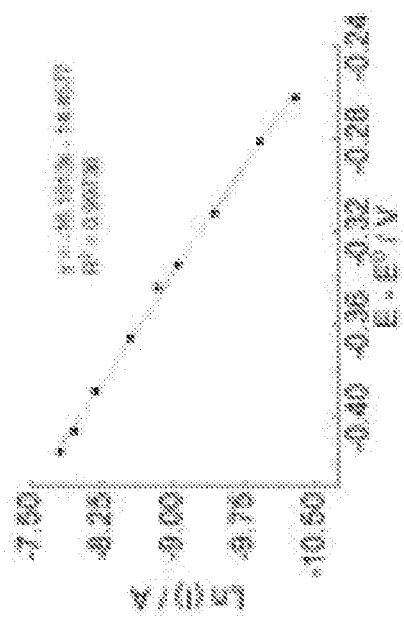
FIG. 45C illustrates the natural log of the peak reduction current ($i_{pc}$) versus the different in potential between the voltage at the peak reduction current ($E_{pc}$) and the literature $E^0$ of the reduction with linear fit.

DTPA is an APC that has been studied as an Fe chelate for various purposes and has shown promising stability from pH 2-10 with high binding constants of 28.60 and 16.55 for Fe$^{3+}$ and Fe$^{2+}$, respectively (Table 9). Unlike previously mentioned APCs, such as EDTA, which can bind metals in 6 locations, DTPA has the ability to bind metals in up to 8 places through the use of 5 carboxylate anions and 3 neutral nitrogens. The final carboxylate arms on FeDTPA are deprotonated at pH 7, so at pH 9 the ligand has a −5 charge, yielding an overall charge for the complex of −2 for Fe$^{3+}$ and −3 for Fe$^{2+}$. K$_2$[Fe(DTPA)].2.5H$_2$O crystals were obtained at pH 9 and X-Ray diffraction (XRD) was performed, showing the ligand to be 7-coordinate in the solid state, binding through 3 N and 4 O in a pentagonal bipyramidal geometry, with a free carboxylate arm (FIG. 41D illustrates the [FeDTPA]$^{2-}$ at pH 9 based on crystallographic data; FIG. 43 illustrates the x-ray crystal structure of K-2[FeDTPA] 2.5H$_2$O. Thermal ellipsoids are displayed at the 50% confidence interval. Hydrogens are omitted for clarity). FeDTPA, in solution, has been seen via IR and Mossbauer spectroscopy to be up to 8-coordinate, binding through all carboxylate arms and nitrogens. Through its coordination and steric bulk, DTPA prevents the binding of both H$_2$O and OH$^-$, which is suspected to inhibit the formation of Fe(OH)$_3$ or an oxo-bridged dimer complex. FeDTPA is thus soluble at high concentration across a range of pH with pseudo-electrochemical reversibility in near neutral and mildly alkaline solutions (FIG. 42B illustrates 10 mM K$_2$FeDTPA. CVs were collected on a glassy carbon electrode at 10 mV/s. Solutions from pH 5.2 were performed in 1 M NaOAc and solutions at pH 9 were performed in 0.25 M KBi).

Figure 32:
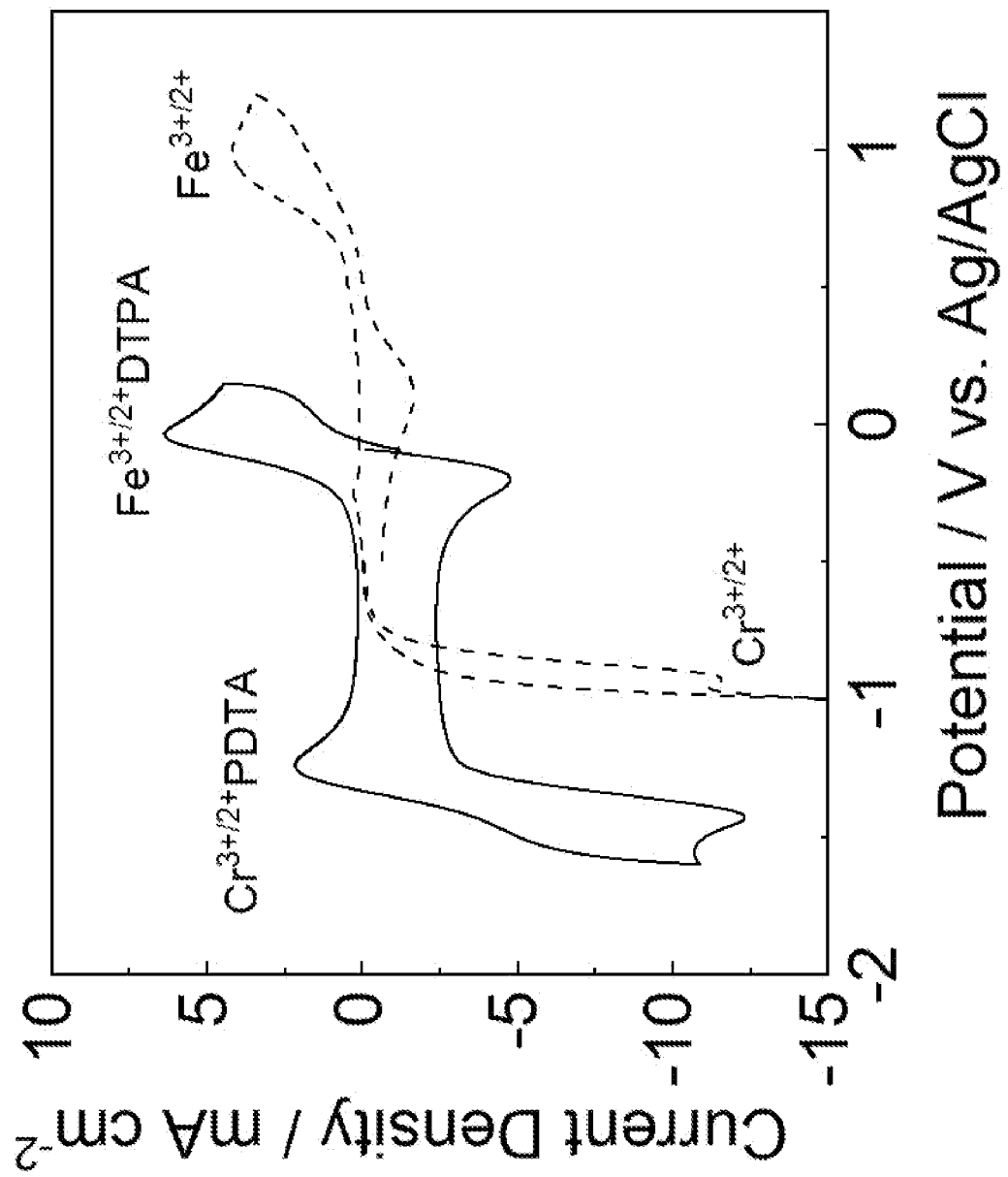
FIG. 32 illustrates the cyclic voltammogram (CV) of 50 mM CrPDTA/FeDTPA with 0.25 m KBi at pH 9.0 and 50 mM CrCl$_3$/FeCl$_2$ in 3 M HCl performed on a glassy carbon electrode at 100 mV s$^{-1}$.
Figure 33A:
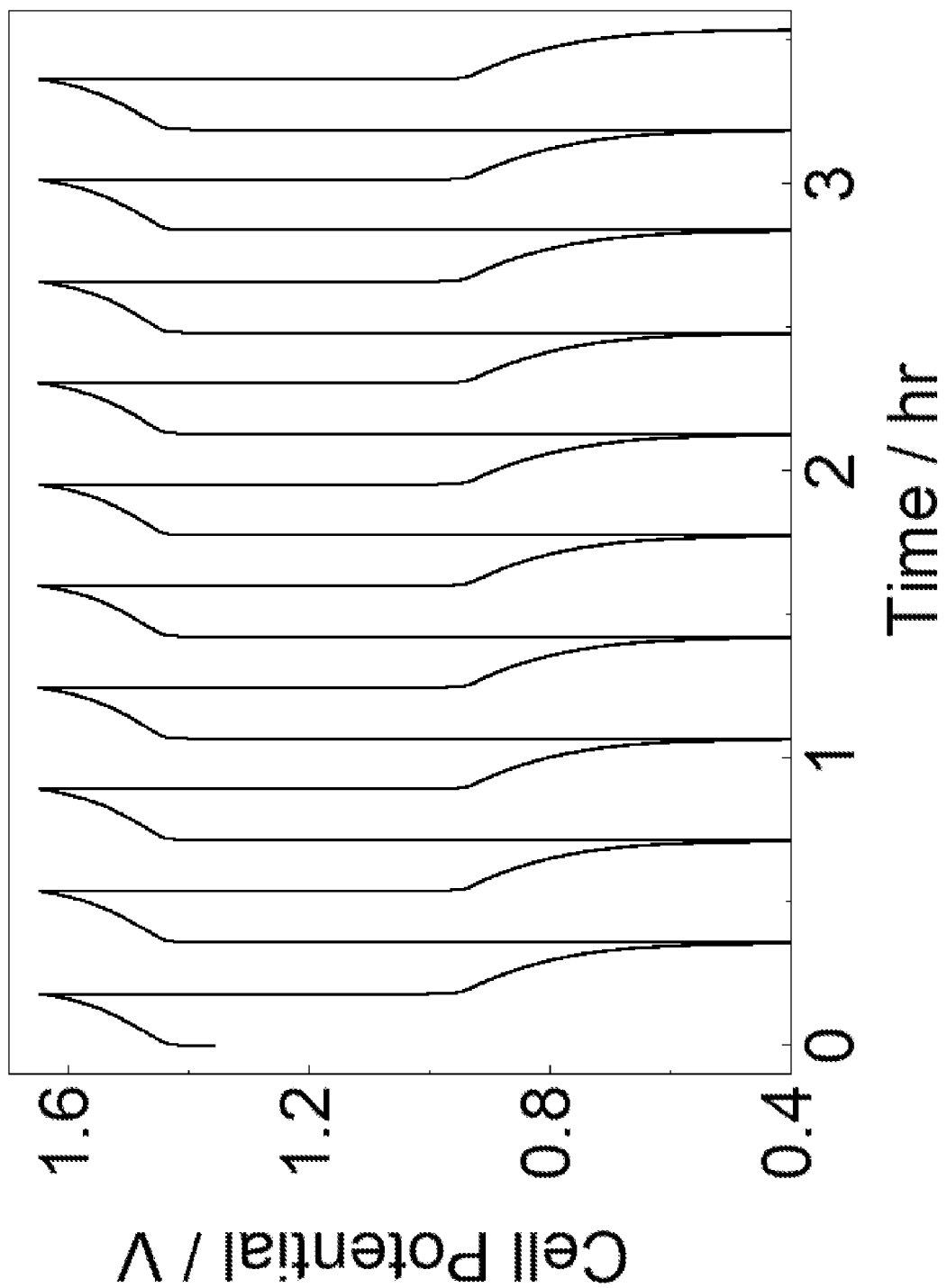
FIG. 33A illustrates a cell cycling data of 0.5 M CrPDTA and 0.5 M FeDTPA with 0.2 m KBi at pH 9 illustrating the cell potential as a function of time for 10 cycles at ±−100 mA cm$^{-2}$.
Figure 33B:
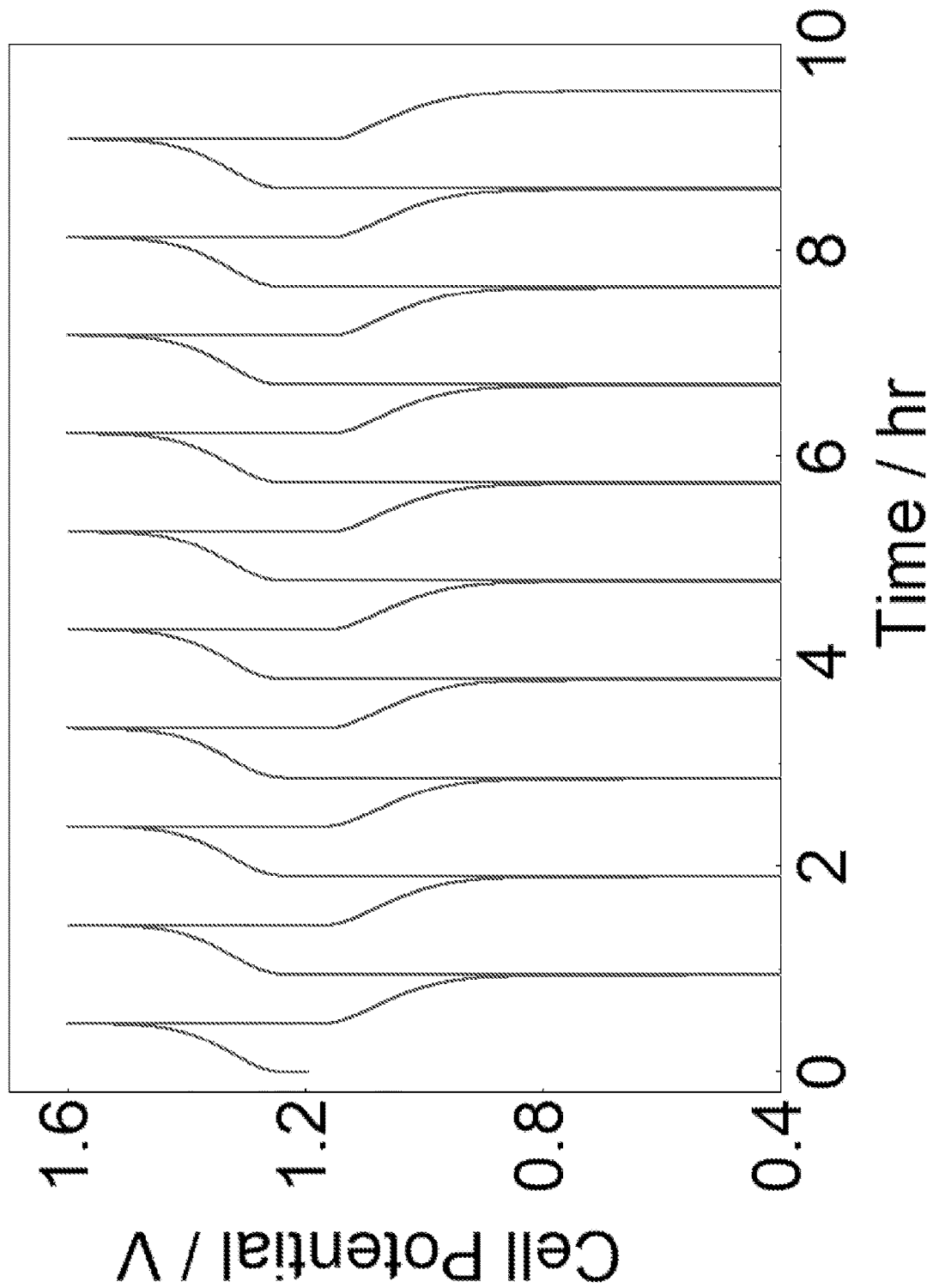
FIG. 33B illustrates a cell cycling data of 0.5 M CrPDTA and 0.5 M FeDTPA with 0.2 m KBi at pH 9 illustrating the cell potential as a function of time for 10 cycles at ±50 mA cm$^{-2}$.
Figure 33C:
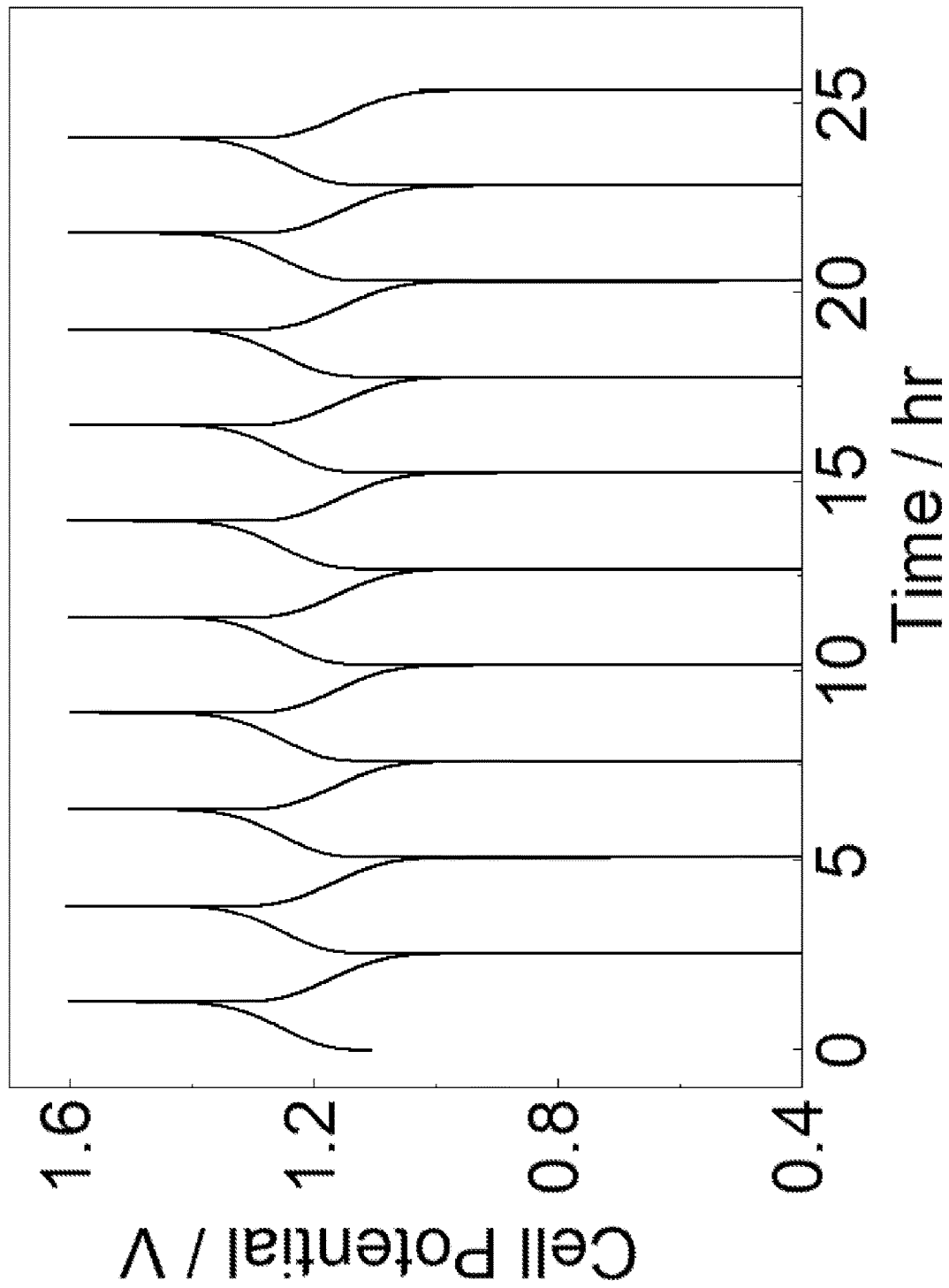
FIG. 33C illustrates a cell cycling data of 0.5 M CrPDTA and 0.5 M FeDTPA with 0.2 m KBi at pH 9 illustrating the cell potential as a function of time for 10 cycles at ±20 mA cm$^{-2}$.
Figure 33D:
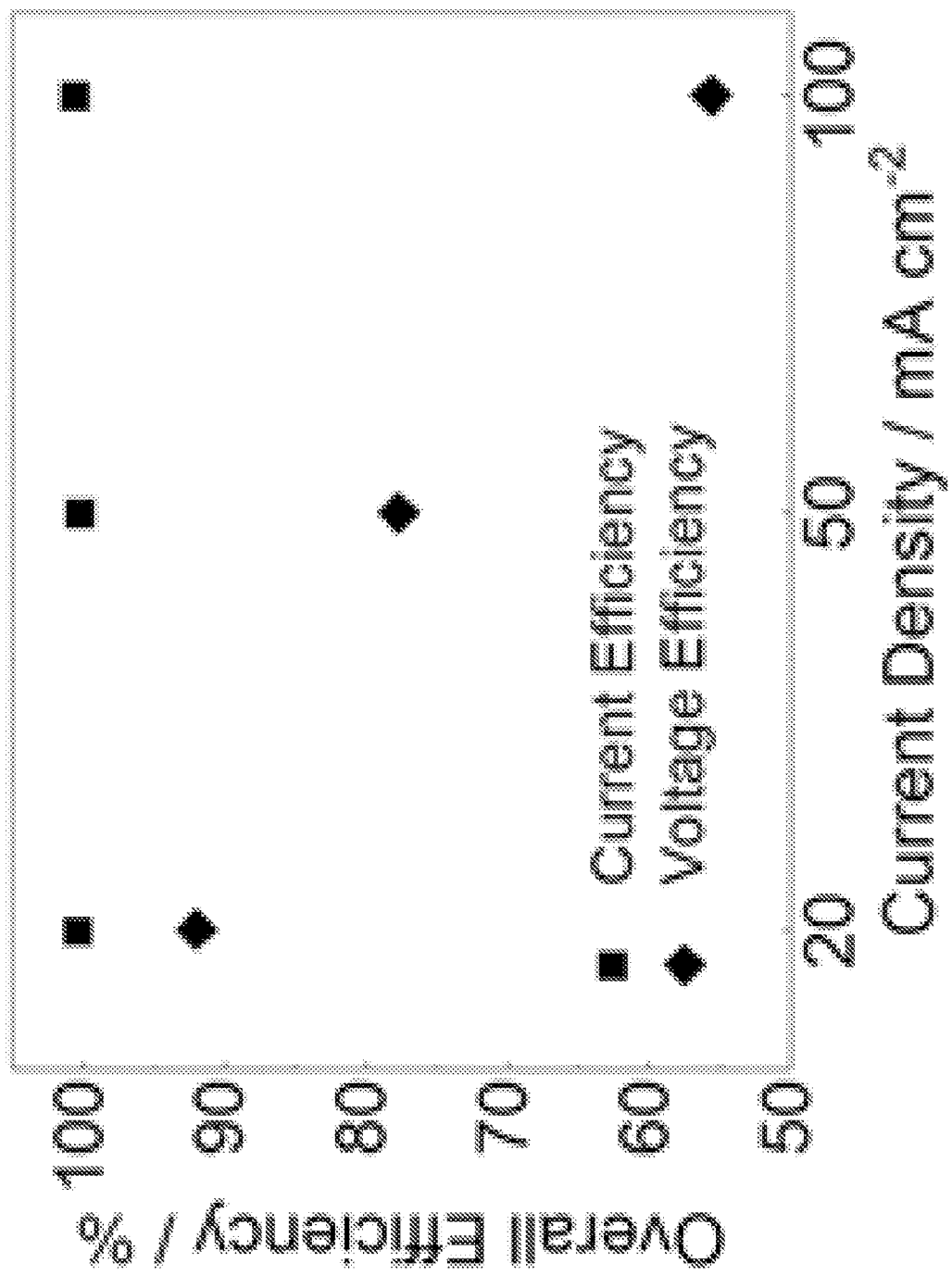
FIG. 33D illustrates a cell cycling data of 0.5 M CrPDTA and 0.5 M FeDTPA with 0.2 m KBi at pH 9 illustrating an average current and voltage efficiencies over 10 cycles at 20, 50, and 100 mA cm$^{-2}$.

Cyclic voltammetry (CV) was performed to compare the electrochemical behavior of FeDTPA and CrPDTA with their respective unchelated metal ions. Kinetic analysis was used to determine the heterogeneous reduction rate constant (k$^0$) and showed on a glassy carbon electrode that k$^0$ increased when Fe was chelated, going from 3.40×10$^{-6}$ cm s$^{-1}$ for FeCl$_3$ in 3 M HCl to 1.55×10$^{-5}$ cm s$^{-1}$ for FeDTPA at pH 9 in a potassium tetraborate (KBi) buffer (Table 10, FIGS. 41A-D, FIGS. 42A-B, FIGS. 44A-C, FIGS. 45A-C). This trend was observed for Cr as well. Compared to their non-chelated counterparts, a greater electrochemical reversibility is observed in the chelated over the non-chelated metals (FIG. 32). In addition to the improved current response, chelation decreases the CV peak separation at 100 mV s$^{-1}$ of both Fe and Cr chelates from 692 mV to 192 mV for Cr$^{3+/2+}$ and 903 mV to 162 mV for Fe$^{3+/2+}$, demonstrating quasi-reversible kinetics on a glassy carbon electrode.

The E$^0$ values of the metal ions both shift negatively by approximately the same value (700-750 mV) upon chelation despite being different ligands; therefore, a battery made of the chelated electrolytes should yield a similar voltage performance as an unchelated system (1.18 V), but with enhanced efficiencies and power output due to the improved kinetics (Table 10). Table 10 provides diffusion rate constant, electron transfer rate constant, and E$^0$ for electrolytes on a glassy carbon electrode unless otherwise noted. All values in Table 10 are approximate.

TABLE 10

| Electrolyte | Diffusion Coefficient (Do) [10$^{-6}$ cm$^2$ s$^{-1}$] | Heterogenous Reduction Rate Constant (k$^0$) [10$^{-6}$ cm s$^{-1}$] | E$^0$ [V vs Ag/AgCl] |
|---|---|---|---|
| FeCl$_3$ | 7.55 | 3.4 | 0.55 |
| K$_2$FeDTPA | 2.41 | 15.5 | −0.15 |
| CrCl$_3$ | NA | 10 | −0.64 |
| KCrPDTA | 6.2 | 170 | −1.39 |

Figure 46:
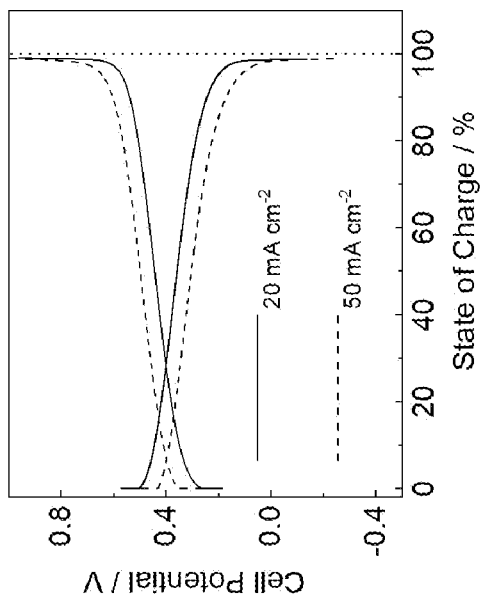
FIG. 46 illustrates a cell composed of 10 mL of 0.5 M FeDTPA and 20 mL 0.5 M $K_4Fe(CN)_6$/0.3 M $K_3Fe(CN)_6$. cell potential as a function of state of charge while cycling at 50 mA $cm^{-2}$ and 20 mA $cm^{-2}$. The example demonstrates the ability of FeDTPA to achieve 99% of available capacity with quantitative current efficiency.

The stability of FeDTPA in its reduced and oxidized states at pH 9 was evaluated by cycling the electrolyte in an RFB against the well-known ferro/ferricyanide (Fe(CN)$_6^{3-/4-}$) redox couple. Solutions were comprised of 10 mL 0.5 M K$_2$FeDTPA as the negolyte against an excess posolyte of 20 mL 0.5 M K$_4$Fe(CN)$_6$/0.3 M K$_3$Fe(CN)$_6$. Both solutions were buffered with 0.2 M KBi at pH 9. The cell was cycled for 10 cycles each at current densities of 50 and 20 mA cm$^{-2}$ to charging and discharging cell potential cutoffs of 0.9 V and 0.0 V, respectively. Although the potential between K$_2$FeDTPA and K$_4$Fe(CN)$_6$ was only 450 mV, current efficiencies of 100.0±0.2% and 99.9±0.1% for 50 and 20 mA cm$^{-2}$ were recorded. FIG. 46 illustrates a cell composed of 10 mL of 0.5 M FeDTPA and 20 mL 0.5 M K$_4$Fe(CN)$_6$/0.3 M K$_3$Fe(CN)$_6$. cell potential as a function of state of charge while cycling at 50 mA cm$^{-2}$ and 20 mA cm$^{-2}$. Table 11 illustrates the current efficiencies and maximum state of charge achieved by FeDTPA. All values in Table 11 are approximate.

TABLE 11

| Current Density [mA cm$^{-2}$] | Current efficiency [%] | Maximum SOC [%] |
|---|---|---|
| 20 | 100.0 ± 0.2 | 99 |
| 50 | 99.9 ± 0.1 | 99 |

The example demonstrates the ability of FeDTPA to achieve 99% of available capacity with quantitative current efficiency). The ability of FeDTPA to be quantitatively cycled between its charged and discharged states indicates that FeDTPA is stable at pH 9 in both the $Fe^{3+}$ and $Fe^{2+}$ charge states.

Figure 47:
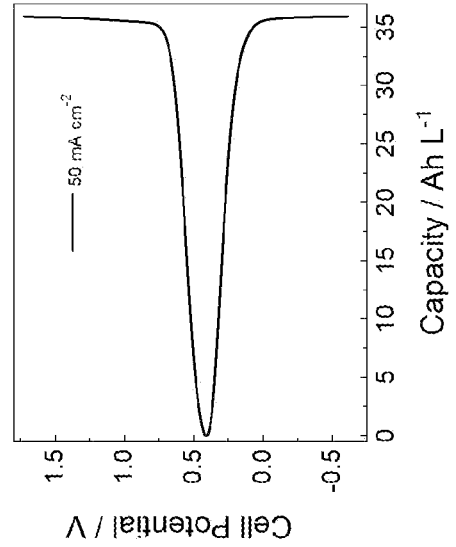
FIG. 47 illustrates a solution of $K_2FeDTPA$ at maximum solubility is bulk electrolyzed against excess $Fe(CN)_6$ at pH 9. The FeDTPA was charged and discharged to 99% SOC at 50 mA $cm^{-2}$ to yield a maximum capacity of 36.2 Ah $L^{-1}$.

To determine the maximum solubility of $K_2$FeDTPA, 10 mL of a 1.35 M $K_2$FeDTPA solution was bulk electrolyzed against an excess of 0.5 M $K_4$Fe(CN)$_6$/0.3 M $K_3$Fe(CN)$_6$ (50 mL) yielding a capacity of up to 36.2 Ah L$^{-1}$. FIG. 47 illustrates a solution of $K_2$FeDTPA at maximum solubility is bulk electrolyzed against excess Fe(CN)$_6$ at pH 9; the FeDTPA was charged and discharged to 99% SOC at 50 mA cm$^{-2}$ to yield a maximum capacity of 36.2 Ah L$^{-1}$. Above this concentration, the FeDTPA does not precipitate, but exhibits a higher viscosity, which makes cell cycling difficult.

Given the stability of FeDTPA at pH 9, FeDTPA was next evaluated as a posolyte against an excess of CrPDTA negolyte. Because the FeDTPA was synthesized as [FeDTPA]$^{2-}$ (charged state), the CrPDTA was pre-charged against a sacrificial Fe(CN)$_6^{4-}$ electrolyte to give 20 mL of 0.5 M $K_2$CrPDTA at 75% SOC. A system of 10 mL of 0.5 M $K_2$FeDTPA was cycled against 20 mL of 0.375 M $K_2$CrPDTA/0.125 M KCrPDTA. An excess of [CrPDTA]$^{2-}$ was used to ensure that the FeDTPA would be the limiting electrolyte in the cell and that at 50% state of charge (SOC) of FeDTPA, CrPDTA would be at 50% SOC as well, such that the equilibrium cell potential was not affected. The cell was cycled 10 times each at current densities of 20, 50, and then 100 mA cm-2 over 38.6 h and the average current efficiency for each current density slightly exceeded 100% with values of 100.3±0.4% (20 mA cm$^{-2}$), 100.1±0.4% (50 mA cm$^{-2}$), and 100.5±0.7% (100 mA cm$^{-2}$) (FIG. 33A-D). Though within error, the observed current efficiencies above 100% are discussed in the supporting information section. The resultant voltage efficiencies were 92±1%, 78±1%, and 56±1% at 20, 50, and 100 mA cm$^{-2}$. Table 12 illustrates cell efficiency data for a cell comprised of 10 mL of 0.5 M $K_2$FeDTPA and 20 mL of 0.375 M $K_2$CrPDTA/0.125 M KCrPDTA (Cell 2). The cell was cycled at current densities of ±20, 50, 100 mA cm$^{-2}$ for 10 cycles each. All values are approximate.

TABLE 12

| Current Density [mA cm$^{-2}$] | Current efficiency [%] | Voltage efficiency [%] | Energy efficiency [%] |
|---|---|---|---|
| 20 | 100.3 ± 0.4 | 92 ± 1 | 92 ± 1 |
| 50 | 100.1 ± 0.3 | 78 ± 1 | 78 ± 1 |
| 100 | 100.5 ± 0.7 | 56 ± 1 | 56 ± 1 |

Figure 34:
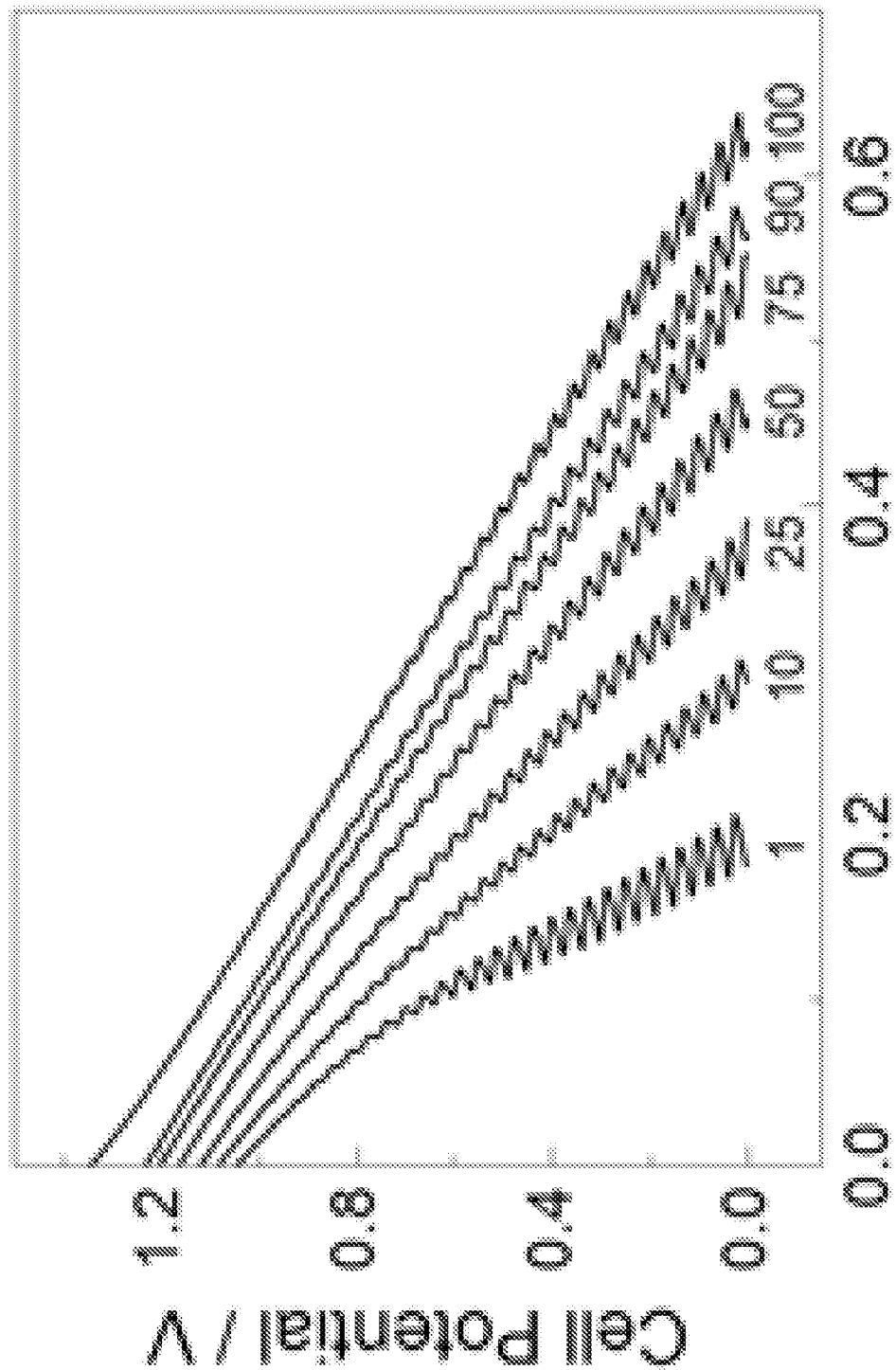
FIG. 34 illustrates polarization curves at varying SOCs of 0.5 M CrPDTA and 0.5 M FeDTPA with 0.2 m KBi at pH 9.
Figure 35:
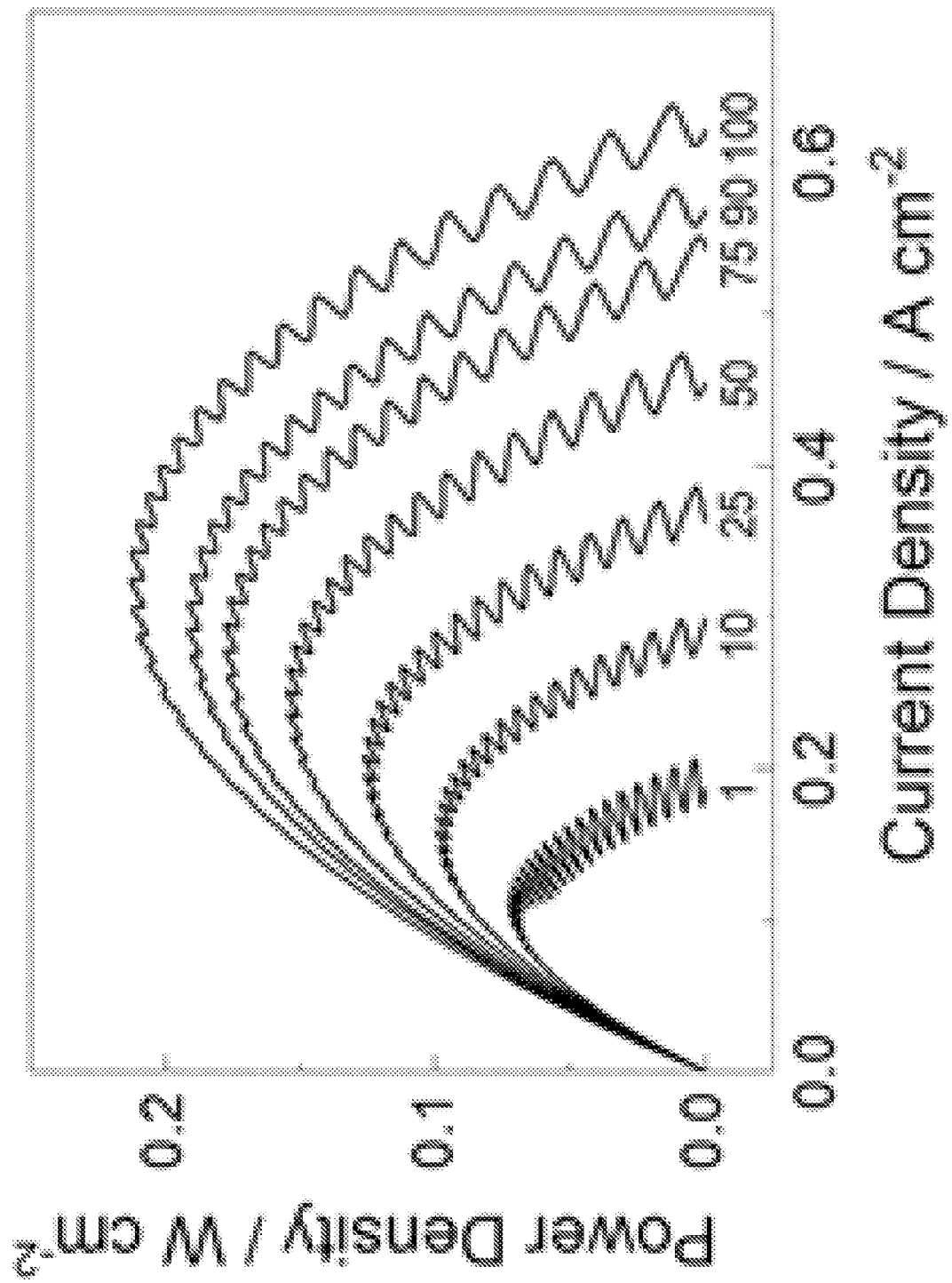
FIG. 35 illustrates the discharge power density vs. current density at varying SOC of a cell comprising 0.5 M CrPDTA and 0.5 M FeDTPA with 0.2 m KBi at pH 9. A maximum power of 216 mW cm$^{-2}$ is achieved.
Figure 36:
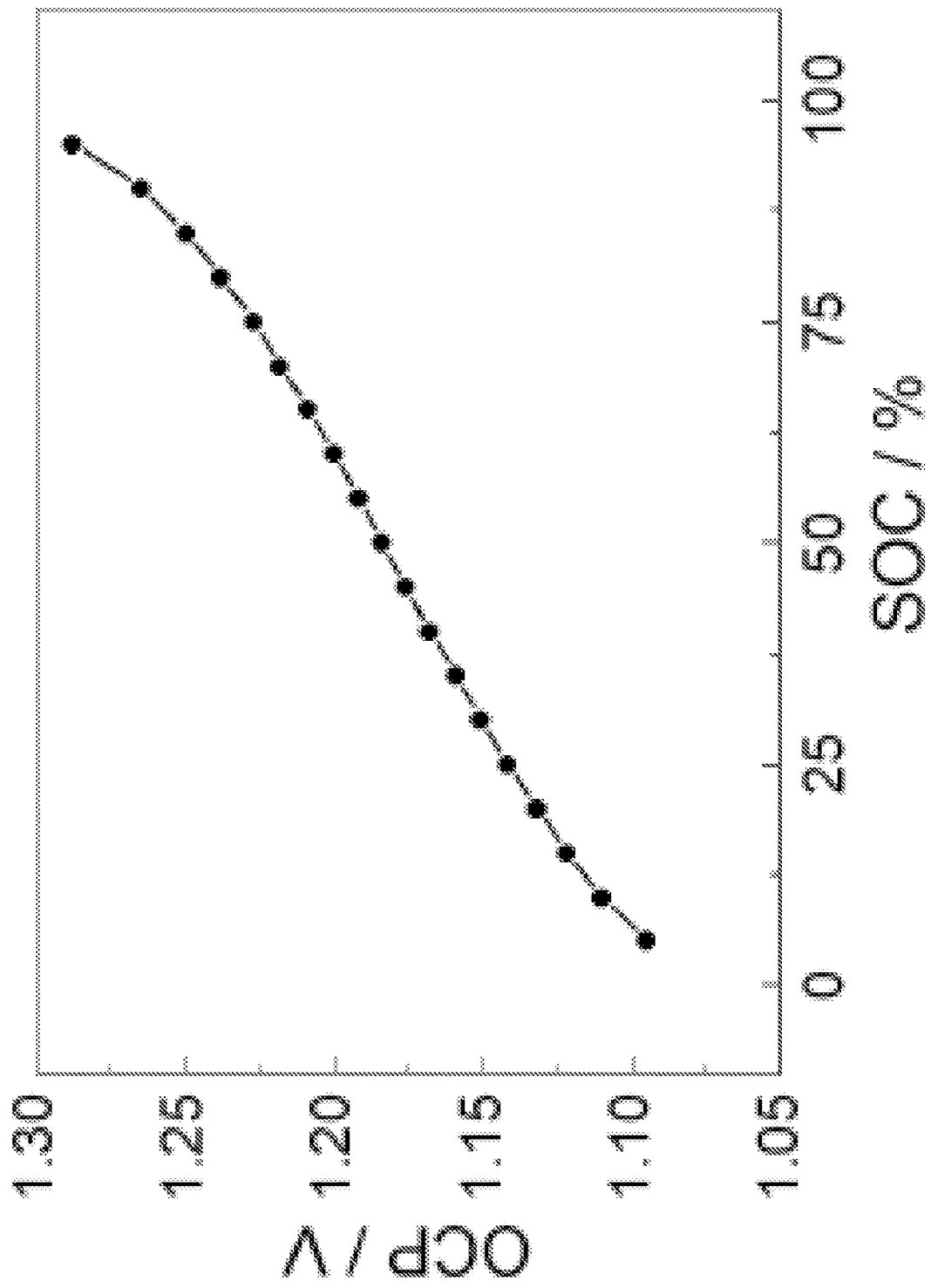
FIG. 36 illustrates the cell open circuit potential v. SOC for a 0.5 M CrPDTA and 0.5 M FeDTPA with 0.2 m KBi at pH 9.
Figure 37:
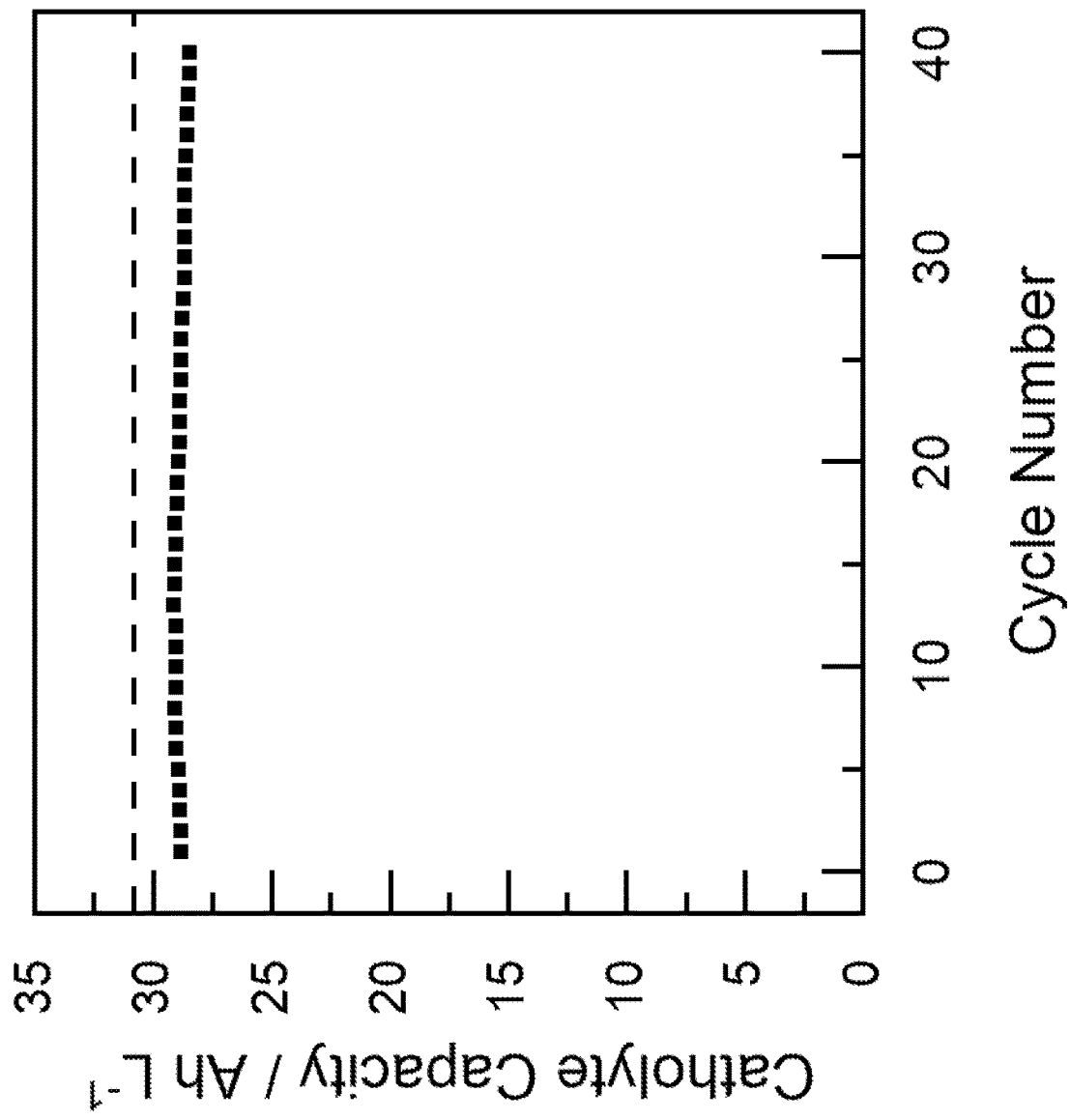
FIG. 37 illustrates the cathode capacity for a cell of 10 mL of 0.5 M $K_2$FeDTPA paired with 20 mL of 0.375 M $K_2$CrPDTA/0.125 M KCrPDTA as a function of cycle number, which is limited by the maximum theoretical FeDTPA capacity of 30.8 AhL$^{-1}$ (dashed line)
Figure 38:
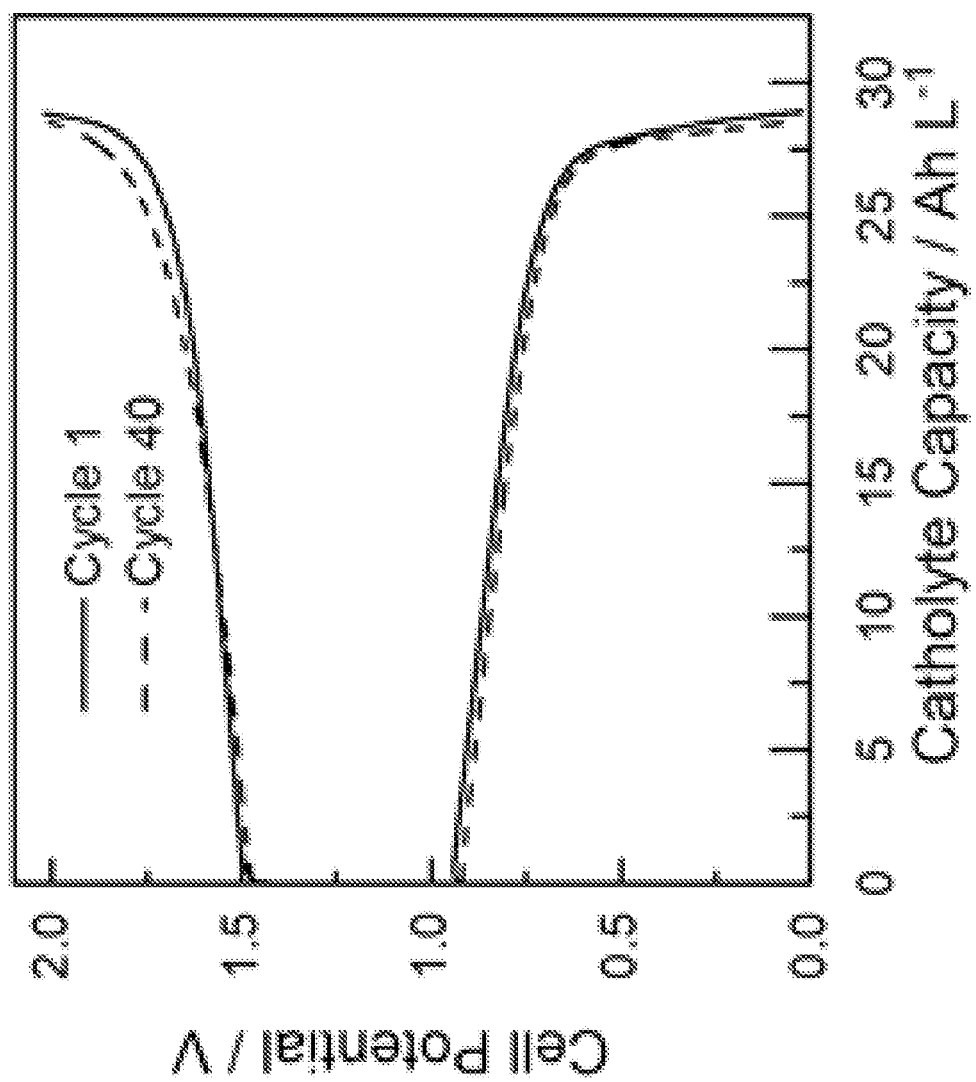
FIG. 38 illustrates the cell potential v. capacity for a cell containing 1.0 M CrPDTA and 1.15 M FeDTPA cell with 0.1 m KBi at pH 9.5 after 1 cycle v. 40 cycles at +/−100 mA cm$^{-2}$.
Figure 39:
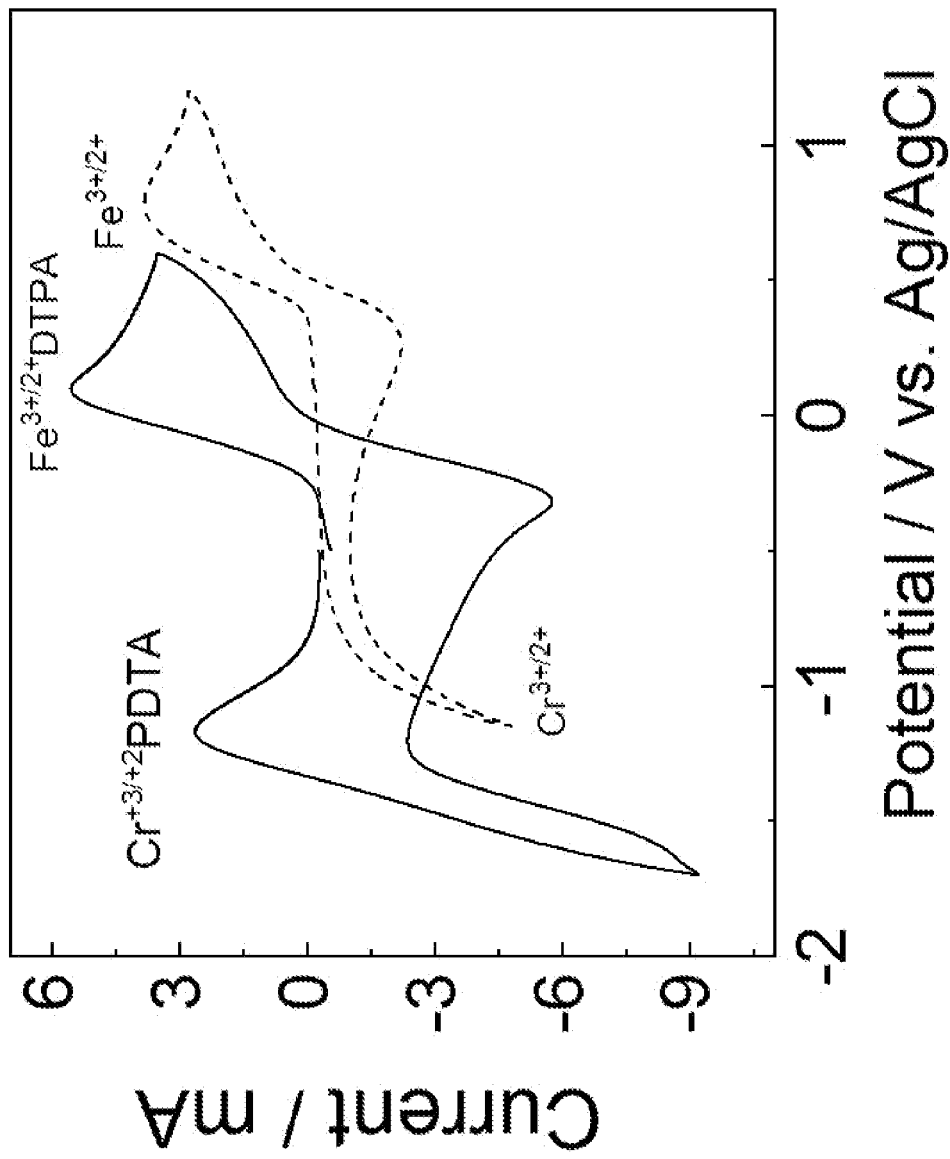
FIG. 39 illustrates a CV of 50 mM CrPDTA/FeDTPA (black) and 0.25 m KBi at pH 9.0 and 50 mM CrCl$_3$/FeCl$_2$ in 3 M HCl systems recorded on carbon paper electrodes at 100 mV s$^{-1}$. The CrCl$_3$ redox potential is unable to be seen within the solvent window.
Figure 40:
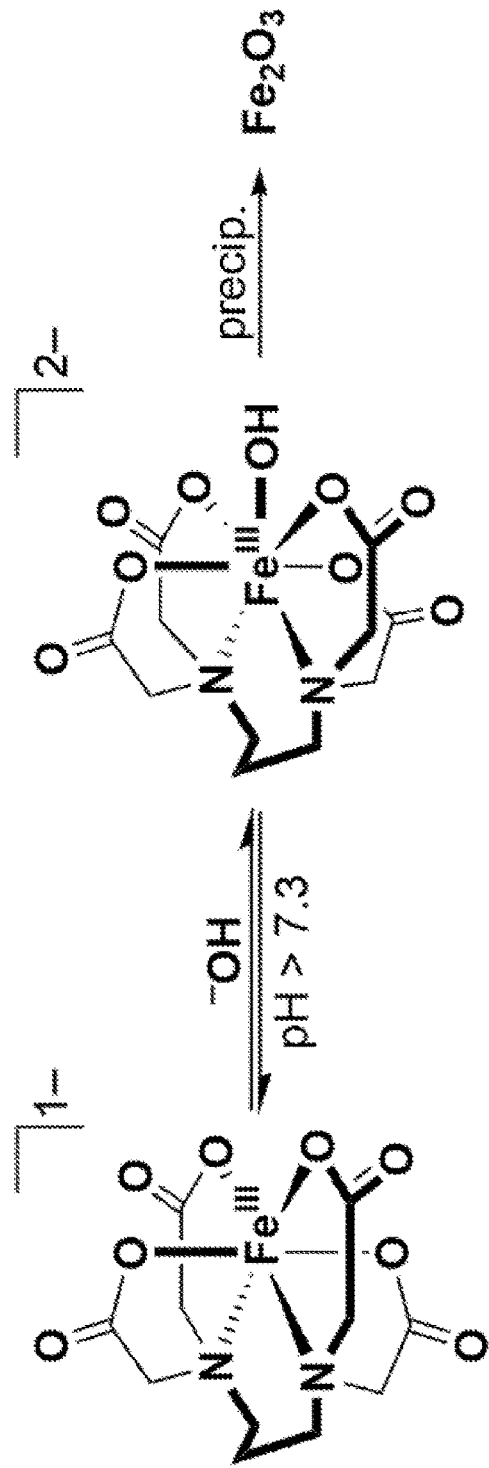
FIG. 40 illustrates a decomposition pathway of [Fe(III) PDTA(OH)]$^{2-}$ in mildly basic conditions.

FIG. 34 illustrates polarization curves at varying SOCs of 0.5 M CrPDTA and 0.5 M FeDTPA with 0.2 M KBi at pH 9. FIG. 35 illustrates the discharge power density vs. current density at varying SOC of a cell comprising 0.5 M CrPDTA and 0.5 M FeDTPA with 0.2 M KBi at pH 9. A maximum power of 216 mW cm-2 is achieved. FIG. 36 illustrates the cell open circuit potential v. SOC for a 0.5 M CrPDTA and 0.5 M FeDTPA with 0.2 M KBi at pH 9. The cell potential was monitored as a function of SOC and the equilibrium potential of the cell was shown to be 1.18 V.

Figure 48:
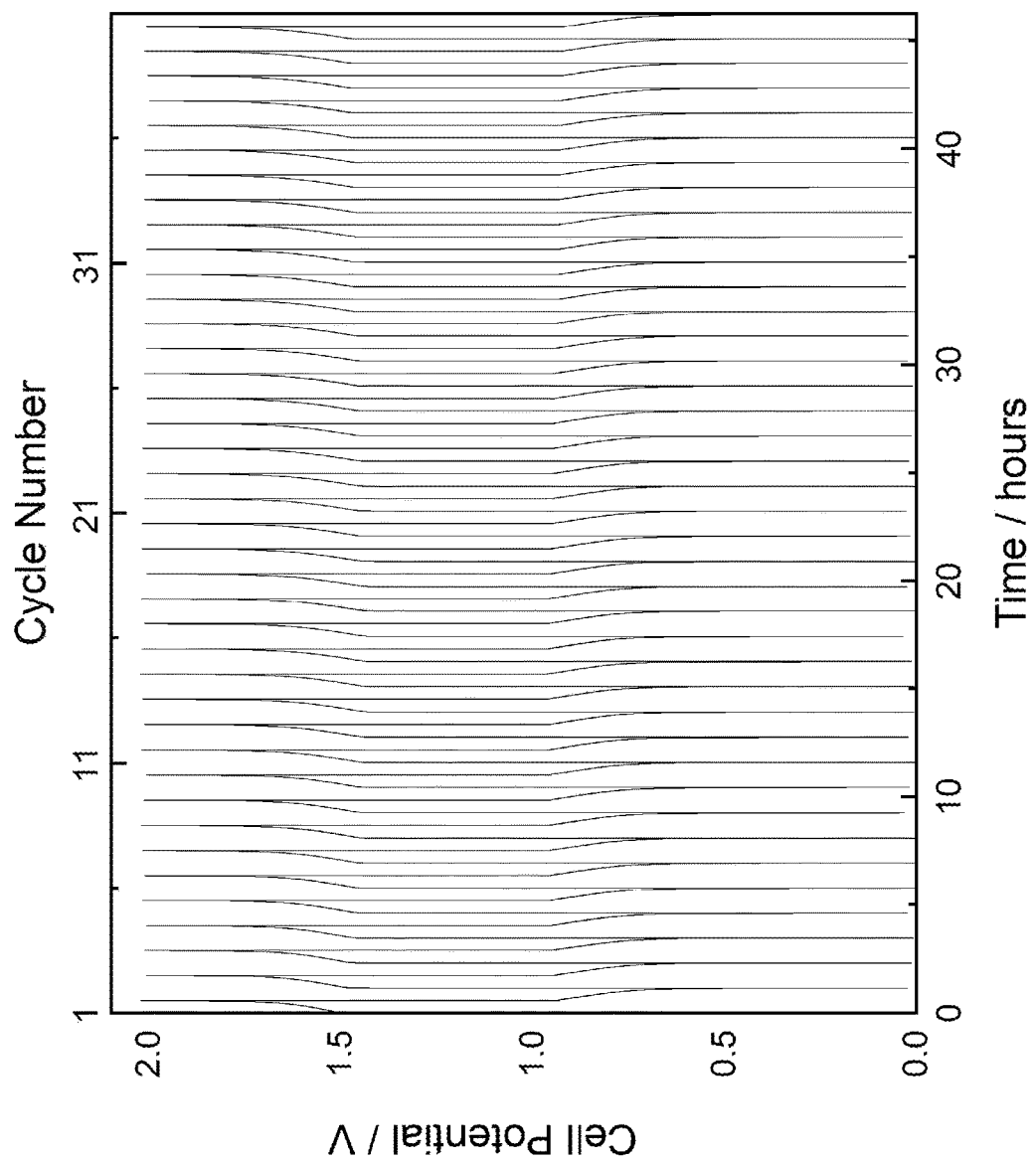
FIG. 48 illustrates cell cycling of 1 M CrPDTA and 1.15 M FeDTPA displaying cell potential over 40 cycles at ±100 mA $cm^{-2}$.

A system of 10 mL of 1.15 M $K_2$FeDTPA was cycled against 30 mL of 0.75 M $K_2$CrPDTA/0.25 M KCrPDTA with 0.1 M KBi at pH 9.5. The cell, 1.0 M CrPDTA and 1.15 M FeDTPA cell with 0.1 M KBi at pH 9.5, was cycled 40 times (46.25 h) to charging and discharging cell potential cutoffs of 2.0 V and 0.0 V, respectively, to demonstrate material stability at high concentration. The cell was able to access 94% of the FeDTPA capacity with an average current efficiency of 100.1±0.1%. The catholyte discharge capacity of the 1st and 40th cycles was 28.82 Ah L$^{-L}$ and 28.49 Ah L$^{-1}$, respectively, corresponding to a loss of 0.33 Ah L$^{-L}$ at a rate of 6.5 mA L$^{-L}$ over 46.25 h (FIG. 48 illustrates the cell cycling of 1 M CrPDTA and 1.15 M FeDTPA displaying cell potential over 40 cycles at ±100 mA cm$^{-2}$). This corresponds to a moderate capacity loss of 0.596% per day (0.029% per cycle), which is typical for posolytes in an RFB with a greater than 1.0 V OCP. After cycling, the cell was bulk electrolyzed to find that 11.5 mmol of FeDTPA remained, indicating that no decomposition or membrane crossover of FeDTPA occurred. Therefore, the capacity loss, as seen by the voltage cutoffs being reached earlier in the 40th cycle compared to the first, is likely due to other factors such as an increase in membrane resistance or in increase in viscosity due to electroosmotic drag.

Through both CV and RFB analysis, the improved electrochemical and physical properties of the reported electrolytes are demonstrated, and therefore highlights the effects of chelation on Fe ions. The exploration of the preferred 7-coordinate geometry of Fe demonstrates the need for tailored chelates to prevent unwanted solvent interactions. The utilization of a high denticity chelate, DTPA, inhibits solvent interactions, therefore increasing the solubility and heterogenous reduction rate constant of Fe ions in mildly basic conditions.

An iron-chromium RFB at near neutral pH has been demonstrated using chelates DTPA and PDTA for Fe and Cr, respectively. FeDTPA exhibits high solubility and can be reversibly cycled at 1.35 M (20° C., pH 9) with suitable kinetics for a next-generation chelated FeCr RFB. In comparison with the highest performing FeCr cell (1.25 M) with catalyst-modified electrodes cycling at 40 mA cm$^{-2}$ at 44° C. in HCl, the fully chelated FeCr RFB can be operated at 50 mA cm$^{-2}$, 20° C., and pH 9 with unmodified carbon electrodes. While both cells have equilibrium potentials of 1.18V, the presented results demonstrate the impact of chelation through improved performance: a maximum discharge power density of 216 mW cm$^{-2}$ compared to 73 mW cm$^{-2}$ (196% increase), a 100% coulombic efficiency compared to 97%, and 78% round trip energy efficiency compared to 73%.

Ranges have been discussed and used within the forgoing description. One skilled in the art would understand that any sub-range within the stated range would be suitable, as would any number within the broad range, without deviating from the invention.

The foregoing description of the present invention, related to a metal chelate, and a battery comprising a metal chelate, as well as a method of making the metal chelate, has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

The invention claimed is:

1. A flow battery electrolyte solution, comprising:
a metal component;
a chelate component;
a buffer; and
a counter ion;
wherein the metal component is a transition metal;
wherein greater than 99 mol % of the metal component in the electrolyte solution is complexed to a chelate component to thereby form a metal chelate;
wherein the electrolyte solution comprises K[Cr(PDTA)];
wherein at least a portion of the chelate component is uncomplexed and serves as a buffer; and
wherein the electrolyte solution has a pH of between 6 and 11.

2. The flow battery electrolyte solution of claim 1, wherein the transition metal comprises chromium.

3. The flow battery electrolyte solution of claim 1, wherein the counter ion comprises potassium.

4. The flow battery electrolyte solution of claim 1, wherein the chelate component comprises uncomplexed PDTA.

5. The flow battery electrolyte solution of claim 1, wherein a solubility of the metal chelate with the counter ion in the electrolyte solution is between about 0.1 M and about 2.0 M.

6. The flow battery electrolyte solution of claim 1, wherein the electrolyte solution is a negative electrolyte solution and further comprises an additive, the additive comprising bismuth, lead, bismuth chelate, lead chelate, or any combination thereof.

7. A flow battery comprising:
the flow battery electrolyte solution of claim 1;
a catholyte comprising $Fe(CN)_6$; and
a membrane comprising a cation exchange membrane.

8. A flow battery electrolyte solution, comprising:
a metal component;
a chelate component;
a buffer; and
a counter ion;
wherein at least a portion of the metal component complexes with at least a portion the chelate component to thereby form a metal chelate;
wherein the metal component is a transition metal;
wherein the chelate component comprises PDTA;
wherein the electrolyte solution comprises K[Cr(PDTA)]; and
wherein the buffer comprises $K_2B_4O_7$, $K_2HPO_4$, $Na_2B_4O_7$, uncomplexed BDTA, uncomplexed CyDTA, uncomplexed EDTA, uncomplexed NTA, uncomplexed PDTA, or any combination thereof.

9. The flow battery electrolyte solution of claim 8, wherein the transition metal comprises chromium.

10. The flow battery electrolyte solution of claim 8, wherein the counter ion comprises potassium.

11. The flow battery electrolyte solution of claim 8, wherein a solubility of the metal chelate with the counter ion in the electrolyte solution is between about 0.1 M and about 2.0 M.

12. The flow battery electrolyte solution of claim 8, wherein the chelate component coordinates with between about 90 mol % and about 100 mol % of the metal component.

13. The flow battery electrolyte solution of claim 8, wherein a pH of the electrolyte solution is between about 6 and about 11.

14. The flow battery electrolyte solution of claim 8, wherein the electrolyte solution is a negative electrolyte solution and further comprises an additive, the additive comprising bismuth, lead, bismuth chelate, lead chelate, or any combination thereof.

15. A flow battery comprising:
the flow battery electrolyte solution of claim 8;
a catholyte comprising $Fe(CN)_6$; and
a membrane comprising a cation exchange membrane.

16. A flow battery electrolyte solution, comprising:
a metal component;
a chelate component;
a buffer; and
a counter ion;
wherein at least a portion of the metal component complexes with at least a portion the chelate component to thereby form a metal chelate;
wherein the metal component is a transition metal;
wherein the chelate component is EDTA; and
wherein the buffer comprises uncomplexed BDTA, uncomplexed CyDTA, uncomplexed EDTA, uncomplexed NTA, uncomplexed PDTA, or any combination thereof.

17. The flow battery electrolyte solution of claim 16, wherein the transition metal is chromium, titanium, manganese, vanadium, cerium, or iron.

18. The flow battery electrolyte solution of claim 16, wherein the counter ion is potassium, sodium, lithium, ammonium, tetraethylammonium, tetrabutylammonium, or a tetraalkylammonium salt.

19. The flow battery electrolyte solution of claim 16, wherein the electrolyte solution comprises Na[Cr(EDTA)].

20. The flow battery electrolyte solution of claim 16, wherein a solubility of the metal chelate with the counter ion in the electrolyte solution is between about 0.1 M and about 2.0 M.

21. The flow battery electrolyte solution of claim 16, wherein the chelate component coordinates with between about 90 mol % and about 100 mol % of the metal component.

22. The flow battery electrolyte solution of claim 16, wherein a pH of the electrolyte solution is between about 6 and about 11.

23. The flow battery electrolyte solution of claim 16, wherein the electrolyte solution is a negative electrolyte solution and further comprises an additive, the additive comprising bismuth, lead, bismuth chelate, lead chelate, or any combination thereof.

24. A flow battery comprising:
the flow battery electrolyte solution of claim 16;
a catholyte comprising $Fe(CN)_6$; and
a membrane comprising a cation exchange membrane.

* * * * *

UNITED STATES PATENT AND TRADEMARK OFFICE
CERTIFICATE OF CORRECTION

| | | |
|---|---|---|
| PATENT NO. | : 12,155,103 B2 | Page 1 of 1 |
| APPLICATION NO. | : 17/440596 | |
| DATED | : November 26, 2024 | |
| INVENTOR(S) | : Scott Waters et al. | |

It is certified that error appears in the above-identified patent and that said Letters Patent is hereby corrected as shown below:

In the Specification

Column 1, Line 10, insert before the heading "TECHNICAL FIELD":
-- STATEMENT REGARDING FEDERALLY SPONSORED RESEARCH OR DEVELOPMENT
This invention was made with government support under grant number NSF DGE1650115 awarded by the National Science Foundation and under grant number P200A180034 awarded by the Department of Education. The Government has certain rights in the invention. --

Signed and Sealed this
Twenty-fourth Day of June, 2025

Coke Morgan Stewart
*Acting Director of the United States Patent and Trademark Office*